United States Patent
Cheung et al.

(10) Patent No.: US 9,453,075 B2
(45) Date of Patent: Sep. 27, 2016

(54) HLA-RESTRICTED, PEPTIDE-SPECIFIC ANTIGEN BINDING PROTEINS

(71) Applicants: Nai-Kong Cheung, Purchase, NY (US); Dimiter Tassev, Chicago, IL (US); Jian Hu, Forest Hills, NY (US)

(72) Inventors: Nai-Kong Cheung, Purchase, NY (US); Dimiter Tassev, Chicago, IL (US); Jian Hu, Forest Hills, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 14/299,509

(22) Filed: Jun. 9, 2014

(65) Prior Publication Data
US 2014/0296492 A1     Oct. 2, 2014

Related U.S. Application Data

(62) Division of application No. 13/984,646, filed as application No. PCT/US2012/024885 on Feb. 13, 2012, now Pat. No. 9,040,669.

(60) Provisional application No. 61/463,082, filed on Feb. 11, 2011.

(51) Int. Cl.
| C07K 16/28 | (2006.01) |
|---|---|
| C07K 16/08 | (2006.01) |
| C07K 16/18 | (2006.01) |
| A61K 39/00 | (2006.01) |

(52) U.S. Cl.
CPC ......... *C07K 16/2833* (2013.01); *C07K 16/085* (2013.01); *C07K 16/18* (2013.01); *A61K 2039/505* (2013.01); *C07K 2317/31* (2013.01); *C07K 2317/32* (2013.01); *C07K 2317/34* (2013.01); *C07K 2317/56* (2013.01); *C07K 2317/565* (2013.01); *C07K 2317/622* (2013.01); *C07K 2317/732* (2013.01); *C07K 2317/92* (2013.01); *C07K 2319/00* (2013.01)

(58) Field of Classification Search
None
See application file for complete search history.

(56) References Cited

FOREIGN PATENT DOCUMENTS

| WO | 03075846 A2 | 9/2003 |
|---|---|---|
| WO | 2008120202 A2 | 10/2008 |
| WO | 2009091826 A2 | 7/2009 |
| WO | 2010106431 A2 | 9/2010 |

OTHER PUBLICATIONS

Domenech N et al., "Antigenicity of HLA-A2 and HLA-B7," Human Immunology, New York, NY, US vol. 30, No. 2, Feb. 1, 1991.
W.R. Burns et al: "A High Molecular Weight Melanoma-Associated Antigen-Specific Chimeric Antigen Receptor Redirects Lymphocytes to Target Human Melanomas," Cancer Research, vol. 70, No. 8, Apr. 15, 2010.
Jensen M C et al: "Antitransgene Rejection Responses Contribute to Attenuated Persistence of Adoptively Transferred CD20/CD19-Specific Chimeric Antigen Receptor Redirected T Cells in Humans," Biology of Blood Marrow Transplantation, Kluge Carden Jennings Publishing, Charlottesville, VA, US. vol. 16, No. 9, Sep. 1, 2010.
L. J. N. Cooper et al: "Enhanced antilymphoma efficacy of CD19-redirected influenza MP1-specific CTLs by cotransfer of T cells modified to present influenza MP1," Blood, vol. 105, No. 4, Feb. 15, 2005.
Sadelain Michel et al: "The promise and potential pitfalls of chimeric antigen receptors," Current Opinion in Immunology, Elsevier, Oxford, GB, vol. 21, No. 2, Jan. 1, 2009.
Xiao-Song Zhong et al: "Chimeric Antigen Receptors Combining 4-1BB and CD28 Signaling Domains Augment PI3kinase/AKT/Bc1-XL Activation and CD8+ T Cell-mediated Tumor Eradication," Molecular Therapy, vol. 18, No. 2, Feb. 1, 2010.
Richard A Morgan et al: "Case Report of a Serious Adverse Event Follwing the Administration of T Cells Transduced With a Chimeric Antigen Receptor Recognizing ERB82." Molecular Therapy, vol. 18, No. 4, Apr. 1, 2010.
Cartellieri Marc et al: "Chimeric Antigen receptor-engineered T cells for immunotherapy of cancer," Journal of Biomedicine & Biotechnology, vol. 2010, 965304, 2010, pp. 1-13.
D V Tassev et al: "Retargeting NK92 cells using an HLA-A2-restricted, EBNA3C-specific chimeric antigen receptor," Cancer Gene Therapy, vol. 19, No. 2, Feb. 1, 2012.

*Primary Examiner* — Brian J Gangle
*Assistant Examiner* — Andrea McCollum
(74) *Attorney, Agent, or Firm* — Heslin Rothenberg Farley & Mesiti P.C.; Kathy Smith Dias

(57) ABSTRACT

Antigen binding proteins with TCR-like paratopes, that is, with an antigen binding region specific for an HLA-A2 restricted peptide are disclosed. The antigen binding proteins encompass antibodies in a variety of forms, including full-length antibodies, substantially intact antibodies, Fab fragments, F(ab')2 fragments, and single chain Fv fragments. Fusion proteins, such as scFv fusions with immunoglobulin or T-cell receptor domains, incorporating the specificity of the antigen binding region for each peptide are also contemplated by the invention. Furthermore, immunoconjugates may include antibodies to which is linked a radioisotope, fluorescent or other detectable marker, cytotoxin, or other molecule are also encompassed by the invention. Among other things, immunoconjugates can be used for delivery of an agent to elicit a therapeutic effect or to facilitate an immune effector function.

16 Claims, 28 Drawing Sheets

HLA-RESTRICTED, PEPTIDE-SPECIFIC ANTIGEN BINDING PROTEINS

CROSS-REFERENCE TO RELATED APPLICATIONS

This application is a divisional of U.S. application Ser. No. 13/984,646 filed on Aug. 9, 2013, now issued as U.S. Pat. No. 9,040,669, which is a national phase filing under 35 U.S.C. §371 of PCT International Application PCT/US2012/024885, filed Feb. 13, 2012, and published under PCT Article 21(2) in English as WO2012/109659 on Aug. 16, 2012. This application also claims priority from U.S. Provisional Application No. 61/463,082, filed Feb. 11, 2011, entitled GENERATION AND USE OF HLA-A2 RESTRICTED, PEPTIDE-SPECIFIC MONOCLONAL ANTIBODIES AND CHIMERIC ANTIGEN RECEPTORS. The contents of each of these applications are hereby incorporated by reference in their entirety into the present disclosure.

SEQUENCE LISTING

The instant application contains a Sequence Listing, created on Jan. 20, 2016; the file, in ASCII format, is designated 3314019BSequenceListing.txt and is 51,295 bytes in size. The file is hereby incorporated by reference in its entirety into the instant application.

BACKGROUND OF THE INVENTION

1. Technical Field

The present invention relates generally to antigen-binding protein molecules involved in immune function. More particularly, the present invention relates to recombinant antibodies, chimeric antigen receptors and fragments thereof with specificity for an HLA-restricted peptide, where the peptide is derived from a cellular or viral protein of interest.

2. Background Information

Advances in adoptive T cell immunotherapy have led to several promising options for cancer patients in the past decade. T-cell based immunotherapy for cancer stemmed from studies which showed a correlation of increased numbers of tumor infiltrating lymphocytes (TILs) in surgical specimens and patient outcome. It is generally believed that this infiltration of TILs represents activation of an anti-tumor mechanism and that the infiltration was mediated through the expression of tumor associated antigens in the context of MHC. These findings eventually led researchers to try and take advantage of antigen-specific T cells for the treatment of cancer.

For induction of cytotoxic T-cell (CTL) responses, intracellular proteins are usually degraded by the proteasome or endo/lysosomes, and the resulting peptide fragments bind to MHC class I or II molecules. These peptide-MHC complexes are displayed at the cell surface where they provide targets for T cell recognition via a peptide-MHC (pMHC)-T cell receptor (TCR) interaction. Vaccinations with peptides derived from cellular and viral protein can induce HLA-A0201-restricted cytotoxic CD8 T cells, which are capable of killing tumor cells or virally-infected cells.

Antibodies are increasingly being used as therapeutic agents to fight cancer, autoimmune disease and infection. Therapeutic antibodies have been exploited based on their multiple mechanisms of action, which include the following: 1) naked antibodies killing tumor cells directly by ADCC or CDC (e.g. trastuzumab), 2) blocking or stimulating a cell membrane molecule to induce cell death (e.g. cetuximab), 3) neutralizing a secreted moiety (e.g. bevacizumab), 4) killing via an attached moiety such as a drug, toxin, radioisotope and 5) modulating the immune system via T cell effector functions.

In almost all cases, to generate a therapeutic benefit, antibodies have to possess critical properties including high affinity for their targeted antigen, minimal acute and long-term side effects, and in specific applications, high affinity for human Fc receptors (4). In addition, the targeted antigen has to be expressed at high levels on tumors but not on normal tissues (specificity or selectivity), consistently expressed in the specific tumor among patients and within patients (low heterogeneity), and should either be essential for the survival of the cancer cell or unlikely to be down regulated.

To achieve these attributes, researchers can now reengineer existing antibodies to make them less immunogenic, modifying both protein and carbohydrate residues in the Fc regions to enhance ADCC and CDC, shrinking their sizes for potentially better tumor penetration, mutating the variable regions to improve affinity, increasing avidity by changing antibody valency, and constructing novel antibody-fusion proteins such as those for multi-step targeting (5) and for redirecting immune cells by way of a chimeric antigen receptor (CAR). Furthermore, researchers continue to define the structural attributes and the host characteristics responsible for success among currently approved antibodies (6).

With the objective of eliminating or neutralizing the pathogenic agent or disease target, including bacterial, viral or tumor targets, antigen-specific, antibody-based treatments are particularly attractive because of the antibody's exquisite specificity.

SUMMARY OF THE INVENTION

The present invention, therefore, is based on the identification of antigen-specific binding sequences from which a variety of antigen-binding proteins can be produced, for example, an antibody specific for an antigen that represents a complex of a protein fragment (peptide) and an HLA molecule similar to that typically recognized by a T-cell receptor following antigen processing and presentation of the protein to the T-cell. Phage display is used to select an initial antigen-binding molecule that can be used to engineer the antigen-binding proteins of the invention, which include antibodies and chimeric antigen receptors (CARs).

In one aspect, therefore, the invention relates to an isolated antigen-binding protein or antigen-binding fragment thereof comprising one of:

(A) an antigen binding region having the amino acid sequence of one of SEQ ID NOS: 2, 5, 8, 10, 13, 14, 17, 20;

(B) an antigen binding region comprising a $V_H$ and $V_L$, respectively, with amino acid sequences selected from SEQ ID NOs: 22 and 23; 24 and 25; 26 and 27; 28 and 29; 30 and 31; 32 and 33; 34 and 35; and 36 and 37; or (C) (i) the following three light chain (LC) complementarity determining regions (CDRs):

(a) a LC CDR1 comprising the amino acid sequence of SEQ ID NO: 56; and (b) a LC CDR2 and CDR3 comprising respectively, the amino acid sequence of SEQ ID NOs: 57 and 64, 58 and 65, 59 and 66, 60 and 67, 61 and 68, 61 and 69, 62 and 70 and 63 and 71; and (ii) the following three heavy chain (HC) CDRs:
(a) a HC CDR1 comprising the amino acid sequence of SEQ ID NO: 38; and
(b) a LC CDR2 and CDR3 comprising respectively the amino acid sequence of one of SEQ ID NOs: 40 and 48, 41 and 49, 42 and 50, 43 and 51, 44 and 52, 45 and 53, 46 and 54 and 47 and 55.

In a related aspect, the invention relates to an isolated antigen-binding protein or antigen-binding fragment thereof, wherein the isolated antigen-binding protein is an antibody or a chimeric antigen receptor. The antibody is a full-length antibody, a substantially intact antibody, a Fab fragment, a F(ab')$_2$ fragment or a single chain variable fragment (scFv).

In the isolated antigen-binding protein, whether an antibody or CAR, the antigen-binding region specifically binds to an epitope of an HLA-peptide complex.

Peptides that are recognized by the antigen-binding proteins of the invention as part of an HLA-peptide complex include, but are not limited to, a peptide with the amino acid sequence RMFPNAPYL (SEQ ID NO:1); a peptide with the amino acid sequence LLDFVRFMGV (SEQ ID NO:4); a peptide with the amino acid sequence RLTRFLSRV (SEQ ID NO: 7); a peptide with the amino acid sequence RIIT-STILV (SEQ ID NO: 12); and a peptide with the amino acid sequence LLEEMFLTV (SEQ ID NO:19). In some embodiments, the peptide is recognized in associate with an HLA-A2 antigen.

In yet another aspect, the isolated antigen-binding protein of the invention is a scFv comprising an amino acid sequence selected from the group consisting of SEQ ID NOS: 2, 5, 8, 10, 13, 14, 17 and 20.

In a related aspect, the isolated antigen-binding protein is a fusion protein comprising an antigen-binding region as disclosed in any of Tables 1-8.

In another aspect, the invention relates to an immunoconjugate comprising a first component which is an antigen-binding protein, or antigen-binding fragment thereof as disclosed herein. The immunoconjugate comprises a second component that is a cytotoxin, a detectable label, a radio-isotope, a therapeutic agent, a binding protein or a molecule having a second amino acid sequence. Where the second component is a binding protein or second antibody, the binding protein or second antibody has binding specificity for a target that is different from the HLA-peptide complex.

In a related aspect, therefore, the present invention relates to bispecific antibody comprising an antigen-binding protein or functional fragment thereof as described herein.

BRIEF DESCRIPTION OF THE DRAWINGS

FIG. 6B shows the digested PCR products as they appeared on a 1% agarose gel following digestion with NheI and ApaI.

μM) or without (0 μM) the LLDFVRFMGV (SEQ ID NO: 4) peptide in serum-free IMDM media at 37° C. for 5 hours. The cells, in addition to beads containing known amounts of anti-human IgG$_1$ antibodies, were stained with the scFv-Fc and the cell's fluorescence intensity was correlated to that of the beads and their number of binding sites. Using these four peptide concentrations and corresponding number of complexes, a standard curve was created with an R$^2$ value of 0.9948. FIG. 10B shows a close-up view of the lower end of the peptide and complex spectrum.

FIG. 11B shows that when purified WT1 Clone 45 scFv-Fc was tested for binding on T2 cells pulsed with the RMFPNAPYL (SEQ ID NO: 1) or RLTRFLSRV (SEQ ID NO: 7) peptide (40 μM), the scFv-Fc (unfilled lines) was only able to recognize RMFPNAPYL (SEQ ID NO: 7)-pulsed T2 cells.

FIG. 15A: Along with sequence validation, plasmids isolated from 8 different bacterial colonies, after ligation, transformation and EcoRI and XhoI digestion, were run on a 1% agarose gel. Based on the lambda HindIII and 100 bp markers, it was determined that the bands were the correct size (~1500 bp and ~6000 bp). FIG. 15B: The structure of the resulting WT1 Clone 45 CAR vector has the same components as the original St. Jude CAR vector with the only difference being the scFv sequence.

FIG. 16A: CAR-equipped NK92MI cells were gated based on GFP fluorescence and analyzed for CD107a expression. NK92MI cells which were cultured without any T2 cells or those which were cocultured with unpulsed and YMFPNAPYL (SEQ ID NO: 76) -pulsed T2 cells were unreactive while NK92MI cells which were cocultured with LLDFVRFMGV (SEQ ID NO: 4)-pulsed T2 cells led to a 27% increase in CD107a expression above background levels. FIG. 16B: T2 cells were pulsed with decreasing concentrations of LLDFVRFMGV (SEQ ID NO: 4) and subsequently cocultured with CAR-equipped NK92MI cells. NK92MI cells presented noticeable amounts of CD107a on their cell surface even when T2 cells were pulsed with only 10 nM of peptide.

FIG. 19A: CAR equipped NK92MI cells were able to specifically differentiate between peptide pulsed DIMT and 6268A BLCL, with a clear difference in cytotoxicity between the two different targets. FIG. 19B: CAR-mediated killing of peptide-pulsed DIMT BLCL could be blocked using the EBNA Clone 315 scFv-Fc fusion protein, but not by an irrelevant, isotype-matched scFv-Fc, at a 20:1 E:T ratio.

FIG. 20A: CAR-equipped NK92MI cells were more reactive towards the HLA-A2$^+$ DIMT and JG19 BLCL versus the HLA-A2$^-$ 6268A and GKO BLCL when cocultured in the absence of any exogenous peptide. FIG. 20B: CAR-mediated killing of unpulsed DIMT BLCL could be blocked using the EBNA Clone 315 scFv-Fc fusion protein but not by an irrelevant, isotype-matched scFv-Fc, at a 10:1 E:T ratio demonstrating that EBNA Clone 315 CAR-expressing NK92MI cells can specifically detect the HLA-A2-EBNA3C complex on HLA-A2+ BLCLs.

FIG. 26A: CAR equipped NK92MI cells were able to specifically differentiate between DIMT and 6268A BLCL, with a clear difference in cytotoxicity between the two different targets. FIG. 26B CAR-mediated killing of DIMT BLCL could be blocked using the WT1 Clone 45 scFv-Fc fusion protein (20 µg/ml), but not by an irrelavent, isotype-matched scFv-Fc, at a 2:1 E:T ratio.

DETAILED DESCRIPTION OF THE INVENTION

Figure 1:
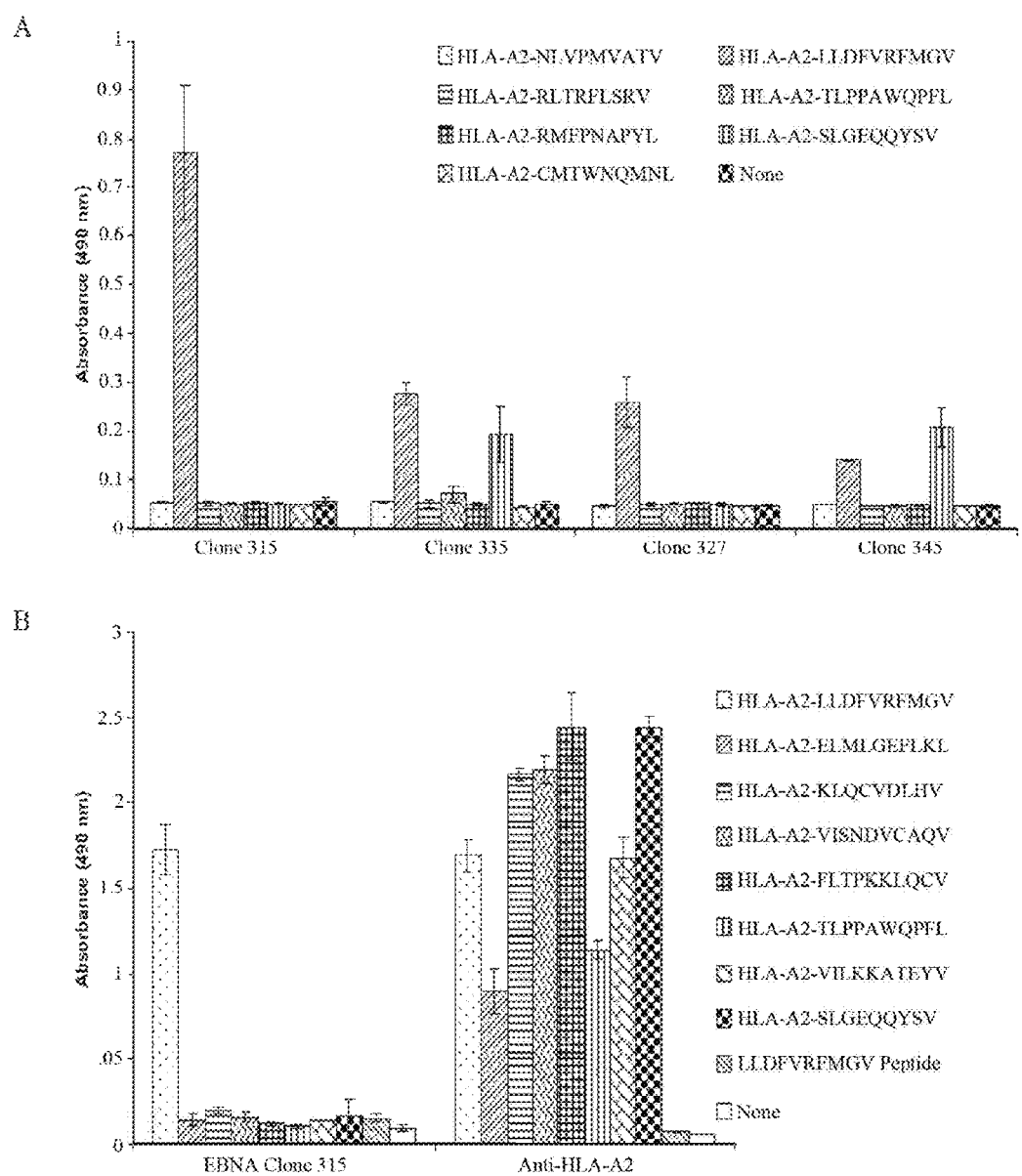
FIG. 1 shows the binding of bacterial supernatant from individual EBNA3C scFv clones 315, 335, 327 and 345 (FIG. 1A) and purified EBNA clone 315 scFv (FIG. 1B) to various HLA-A2-peptide complexes demonstrating that clone 315 is highly specific for the HLA-A2-LLDFVRF-MGV (SEQ ID NO: 4) complex.

All patents, publications, applications and other references cited herein are hereby incorporated in their entirety into the present application.

In practicing the present invention, many conventional techniques in molecular biology, microbiology, cell biology, biochemistry, and immunology are used, which are within the skill of the art. These techniques are described in greater detail in, for example, Molecular Cloning: a Laboratory Manual 3$^{rd}$ edition, J. F. Sambrook and D. W. Russell, ed. Cold Spring Harbor Laboratory Press 2001; Recombinant Antibodies for Immunotherapy, Melvyn Little, ed. Cambridge University Press 2009; "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001). The contents of these references and other references containing standard protocols, widely known to and relied upon by those of skill in the art, including manufacturers' instructions are hereby incorporated by reference as part of the present disclosure.

The following abbreviations are used throughout the application:

ADCC: Antibody-dependent cellular cytotoxicity
ALL: Acute lymphocytic leukemia
AML: Acute myeloid leukemia
APC: Antigen presenting cell
β2M: Beta-2-microglobulin
BiTE: Bi-specific T cell engaging antibody
BLCL: EBV-transformed B-cell lymphoblastic cell line
CAR: Chimeric antigen receptor
CDC: Complement dependent cytotoxicity
CMC: Complement mediated cytotoxicity
CDR: Complementarity determining region (see also HVR below)
$C_L$: Constant domain of the light chain
$CH_1$: 1$^{st}$ constant domain of the heavy chain
$CH_{1, 2, 3}$: 1$^{st}$, 2$^{nd}$ and 3$^{rd}$ constant domains of the heavy chain
$CH_{2, 3}$: 2$^{nd}$ and 3$^{rd}$ constant domains of the heavy chain
CHO: Chinese hamster ovary
CTL: Cytotoxic T cell
EBNA3C: Epstein-Barr nucleur antigen 3C
EBV: Epstein-Barr virus
ECMV: Encephalomyocarditis virus
ER: Endoplasmic reticulum
E:T Ratio: Effector:Target ratio
Fab: Antibody binding fragment
FACS: Flow assisted cytometric cell sorting
FBS: Fetal bovine serum
GFP: Green fluorescence protein
HC: Heavy chain
HEL: Hen egg lysozyme
HLA: Human leukocyte antigen
HVR-H: Hypervariable region-heavy chain (see also CDR)

HVR-L: Hypervariable region-light chain
Ig: Immunoglobulin
IPTG: isopropyl-1-thio-β-D-galactopyranoside
IRES: Internal ribosome entry site
$K_D$: Dissociation constant
$k_{off}$: Dissociation rate
$k_{on}$: Association rate
MHC: Major histocompatibility complex
OPD: O-phenylenediamine
PEG: Polyethylene glycol
scFv: Single-chain variable fragment
SPR: Surface plasmon resonance
TB: Terrific Broth
TCE: T cell epitope
TCR: T cell receptor
TIL: Tumor infiltrating lymphocyte
$V_H$: Variable heavy chain
$V_L$: Variable light chain
WT1: Wilms tumor protein 1

In the description that follows, certain conventions will be followed as regards the usage of terminology. Generally, terms used herein are intended to be interpreted consistently with the meaning of those terms as they are known to those of skill in the art.

An "antigen-binding protein" is a protein or polypeptide that comprises an antigen-binding region or antigen-binding portion, that is, has a strong affinity to another molecule to which it binds. Antigen-binding proteins encompass antibodies, antigen receptors and fusion proteins.

"Antibody" and "antibodies" as those terms are known in the art refer to antigen binding proteins that arise in the context of the immune system. The term "antibody" as referred to herein includes whole, full length antibodies and any fragment thereof in which the "antigen-binding portion" or "antigen-binding region" is retained or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is, composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" or "antigen-binding region" of an antibody (or simply "antigen portion"), as used herein, refers to that region or portion of the antibody that confers antigen specificity; fragments of antigen-binding proteins, for example, antibodies therefore, includes one or more fragments of an antibody that retain the ability to specifically bind to an antigen (e.g., an HLA-peptide complex). It has been shown that the antigen-binding function of an antibody can be performed by fragments of a full-length antibody. Examples of antigen-binding fragments encompassed within the term "antibody fragments" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding portion" of an antibody. These antibody fragments are obtained using conventional techniques known to those of skill in the art, and the fragments are screened for utility in the same manner as are intact antibodies.

An "isolated antibody" or "isolated antigen-binding protein" is one which has been identified and separated and/or recovered from a component of its natural environment.

Traditionally, the MHC-peptide complex could only be recognized by a T-cell receptor (TCR), limiting our ability to detect an epitope of interest to use of T cell-based readout assays. In the present disclosure, antigen binding proteins, including antibodies and chimeric antigen receptors, having an antigen-binding region based on scFvs that are selected from human scFv phage display libraries using recombinant HLA-peptide complexes are described. These molecules demonstrated exquisite specificity, for example as shown with anti-EBNA and anti-WT1 antigen-binding proteins that recognize only the HLA-A2-LLDFVRFMGV (SEQ ID NO: 4) and HLA-A2-RMFPNAPYL (SEQ ID NO: 1) complexes, respectively. In addition, along with their inability to bind to HLA-complexes containing other peptides, the molecules were also unable to bind to the peptides themselves, further demonstrating their TCR-like specificity.

The scFvs of the disclosure selected by phage display were initially tested for their ability to bind to peptide presented on the surface of HLA-positive cells. After T2 cells and BLCLs were incubated in the presence of peptide, the cells could selectively recognize them using flow cytometry. In the case of one peptide, LLDFVRFMGV (SEQ ID NO: 4), the complex which the peptide formed with HLA could be detected on the surface of a BLCL even 24 hours after pulsing, further demonstrating the utility of these antibodies.

In some embodiments, the antigen binding proteins of the invention include antibodies that have the scFv sequence fused to the $2^{nd}$ and 3rd constant domains of the heavy chain (CH$_{2, 3}$), forming the bottom third of the Fc region of a human immunoglobulin to yield a bivalent protein and fragments thereof, increasing the overall avidity and stability of the antibody. In addition, the Fc portion allows the direct conjugation of other molecules, including but not limited to fluorescent dyes, cytotoxins, radioisotopes etc. to the antibody for example, for use in antigen quantitation studies, to immobilize the antibody for affinity measurements using surface plasmon resonance (SPR), for targeted delivery of a therapeutic agent, to test for Fc-mediated cytotoxicity using CD16-expressing immune effector cells and many other applications.

The purified scFv-Fc fusion proteins were tested for binding to their targeted T-cell epitopes (TCEs) by way of ELISA and peptide-pulsed APCs. Once they were validated to maintain their specificity, one molecule, EBNA Clone 315 was used for affinity determination. That this molecule was able to bind bound to its targeted TCE through a 1:1 interaction with 10-100 fold greater affinity compared to a typical TCR-MHC-peptide complex interaction was demonstrated.

Correlation of peptide pulsing of APCs with antigen density was demonstrated. Fluorescently-conjugated scFv-Fc, combined with quantitation beads, allowed the approximation of the number of complexes that are formed when cells are incubated with different concentrations of peptide. Using this information, it was possible to approximate the sensitivity of an scFv and scFv-Fc fusion protein to be around 100 complexes, using flow cytometry.

Lastly, whether the Fc portion of the fusion protein maintained its effector function was tested. Using a scFv embodiment of the invention, CD16(V)-transduced NK92MI cells, and peptide-pulsed target cells, it was demonstrated that the antibody maintained its Fc-mediated effector functions by way of ADCC.

The results presented here highlight the specificity, sensitivity and utility of the antigen binding proteins of the invention in targeting MHC-peptide complexes.

In one embodiment, therefore, the present invention relates to recombinant antigen-binding molecules and portions thereof that recognize a complex of a peptide/protein fragment derived from an intracellular or viral protein, and an MHC class I molecule, for example, as the complex might be appear at the cell surface for recognition by a T-cell.

The molecules of the invention are based on the identification and selection of a single chain variable fragment (scFv) using phage display, the amino acid sequence of which confers the molecules' specificity for the MHC restricted peptide of interest and forms the basis of all antigen binding proteins of the disclosure. The scFv, therefore, can be used to design a diverse array of "antibody" molecules, including, for example, full length antibodies, fragments thereof, such as Fab and F(ab')₂, minibodies, fusion proteins, including scFv-Fc fusions, multivalent antibodies, that is, antibodies that have more than one specificity for the same antigen or different antigens, for example, bispecific T-cell engaging antibodies (BiTe), tribodies, etc. (see Cuesta et al., *Multivalent antibodies: when design surpasses evolution. Trends in Biotechnology* 28:355-362 2010).

In an embodiment in which the antigen-binding protein is a full length antibody, the heavy and light chains of an antibody of the invention may be full-length (e.g., an antibody can include at least one, and preferably two, complete heavy chains, and at least one, and preferably two, complete light chains) or may include an antigen-binding portion (a Fab, F(ab')2, Fv or a single chain Fv fragment ("scFv")). In other embodiments, the antibody heavy chain constant region is chosen from, e.g., IgG1, IgG2, IgG3, IgG4, IgM, IgA1, IgA2, IgD, and IgE. In some embodiments, the immunoglobulin isotype is selected from IgG1, IgG2, IgG3, and IgG4, more particularly, IgG1 (e.g., human IgG1). The choice of antibody type will depend on the immune effector function that the antibody is designed to elicit.

In constructing a recombinant immunoglobulin, appropriate amino acid sequences for constant regions of various immunoglobulin isotypes and methods for the production of a wide array of antibodies are well known to those of skill in the art.

In some embodiments, the constant region of the antibody is altered, e.g., mutated, to modify the properties of the antibody (e.g., to increase or decrease one or more of: Fc receptor binding, antibody carbohydrate, for example glycosylation or fucosylation, the number of cysteine residues, effector cell function, or complement function).

In one embodiment, the antigen binding protein is an anti-WT1/HLA-A2 antibody or fragment thereof having an antigen binding region that comprises the amino acid sequence of SEQ ID NO: 2 and specifically binds to a peptide with the amino acid sequence RMFPNAPYL (SEQ ID NO: 1) in conjunction with HLA-A2. In other embodiments, the anti-WT-1 antibody is a scFv-Fc fusion protein or full length human IgG with VH and VL regions or CDRs selected from Table 1.

TABLE 1

| Antigen<br>Peptide<br>CDRs: | WT1<br>RMFPNAPYL (SEQ ID NO: 1) | | |
|---|---|---|---|
| | 1 | 2 | 3 |
| VH | SYAMS<br>(SEQ ID<br>NO. 38) | QIDPWGQET<br>LYADSVKG<br>(SEQ ID<br>NO. 40) | LTGRFDY<br>(SEQ ID<br>NO. 48) |
| VL | RASQSISSYLN<br>(SEQ ID<br>NO: 56) | SASQLQS<br>(SEQ ID<br>NO: 57) | QQGPGTPNT<br>(SEQ ID<br>NO: 64) |
| Full VH | EVQLLESGGGLVQPGGSLRLSCAASGFTFSSYAMSWVRQAP<br>GKGLEWVSQIDPWGQETLYADSVKGRFTISRDNSKNTLYLQ<br>MNSLRAEDTAVYYCAKLTGRFDYWGQGTLVTVS<br>(SEQ ID NO: 22) | | |
| Full VL | STDIQMTQSPSSLSASVGDRVTITCRASQSISSYLNWYQQK<br>PGKAPKLLIYSASQLQSGVPSRFSGSGSGTDFTLTISSLQP<br>EDFATYYCQQGPGTPNTFGQGTKVEIKRA<br>(SEQ ID NO: 23) | | |
| scFv<br>clone<br>45 | EVQLLESGGGLVQPGGSLRLSCAASGFTFSSYAMSWVRQAP<br>GKGLEWVSQIDPWGQETLYADSVKGRFTISRDNSKNTLYLQ<br>MNSLRAEDTAVYYCAKLTGRFDYWGQGTLVTVSSGGGGSGG<br>GGSGGGGSTDIQMTQSPSSLSASVGDRVTITCRASQSISSY<br>LNWYQQKPGKAPKLLIYSASQLQSGVPSRFSGSGSGTDFTL<br>TISSLQPEDFATYYCQQGPGTPNTFGQGTKVEIKRA<br>(SEQ ID NO: 2) | | |
| DNA<br>(5'-3') | GAGGTGCAGCTGTTGGAGTCTGGGGGAGGCTTGGTACAGCC<br>TGGGGGGTCCCTGAGACTCTCCTGTGCAGCCTCTGGATTCA<br>CCTTTAGCAGCTATGCCATGAGCTGGGTCCGCCAGGCTCCA<br>GGGAAGGGGCTGGAGTGGGTCTCACAGATTGATCCTTGGGG<br>TCAGGAGACATTGTACGCAGACTCCGTGAAGGGCCGGTTCA<br>CCATCTCCAGAGACAATTCCAAGAACACGCTGTATCTGCAA<br>ATGAACAGCCTGAGAGCCGAGGACACGGCCGTATATTACTG<br>TGCGAAACTTACTGGTCGGTTTGACTACTGGGGCCAGGGAA<br>CCCTGGTCACCGTCTCAAGCGGTGGAGGCGGTTCAGGCGGA<br>GGTGGCAGCGGCGGTGGCGGGTCGACGGACATCCAGATGAC<br>CCAGTCTCCATCCTCCCTGTCTGCATCTGTAGGAGACAGAG<br>TCACCATCACTTGCCGGGCAAGTCAGAGCATTAGCAGCTAT<br>TTAAATTGGTATCAGCAGAAACCAGGGAAAGCCCCTAAGCT<br>CCTGATCTATTCGGCATCCCAGTTGCAAAGTGGGGTCCCAT<br>CAAGGTTCAGTGGCAGTGGATCTGGGACAGATTTCACTCTC<br>ACCATCAGCAGTCTGCAACCTGAAGATTTTGCAACTTACTA<br>CTGTCAACAGGGTCCGGGGACTCCTAATACGTTCGGCCAAG<br>GGACCAAGGTGGAAATCAAACGGGCC<br>(SEQ ID NO: 3) | | |

In another embodiment, the antigen binding protein is an anti-EBNA3C antibody or fragment thereof that has an antigen binding region that comprises the amino acid sequence of SEQ ID NO: 5 and specifically binds to a peptide with the amino acid sequence LLDFVRFMGV (SEQ ID NO: 4) in conjunction with HLA-A2. In other embodiments, the anti-EBNA3C antibody is a scFv-Fc fusion protein or full length human IgG with VH and VL regions or CDRs selected from Table 2.

TABLE 2

| Antigen Peptide CDRs | EBNA3C LLDFVRFMGV (SEQ ID NO: 4) | | |
|---|---|---|---|
| | 1 | 2 | 3 |
| VH | GYAMS (SEQ ID NO: 39) | EIAPPGLNT RYADSVKG (SEQ ID NO: 41) | SDTAFDY (SEQ ID NO: 49) |
| VL | RASQSISSYLN (SEQ ID NO: 56) | LASNLQS (SEQ ID NO: 58) | QQAEYMPLT (SEQ ID NO: 65) |
| Full VH | EVQLLESGGGLVQPGGSLRLSCAASGFTFSGYAMSWVRQAPG KGLEWVSEIAPPGLNTRYADSVKGRFTISRDNSKNTLYLQMN SLRAEDTAVYYCAKSDTAFDYWGQGTLVTVS (SEQ ID NO: 24) | | |
| Full VL | STDIQMTQSPSSLSASVGDRVTITCRASQSISSYLNWYQQKP GKAPKLLIYLASNLQSGVPSRFSGSGSGTDFTLTISSLQPED FATYYCQQAEYMPLTFGQGTKVEIKRA (SEQ ID NO: 25) | | |
| scFv clone 315 | EVQLLESGGGLVQPGGSLRLSCAASGFTFSGYAMSWVRQAPG KGLEWVSEIAPPGLNTRYADSVKGRFTISRDNSKNTLYLQMN SLRAEDTAVYYCAKSDTAFDYWGQGTLVTVSSGGGGSGGGGS GGGGSTDIQMTQSPSSLSASVGDRVTITCRASQSISSYLNWY QQKPGKAPKLLIYLASNLQSGVPSRFSGSGSGTDFTLTISSL QPEDFATYYCQQAEYMPLTFGQGTKVEIKRA (SEQ ID NO: 5) | | |
| DNA (5'-3') | GAGGTGCAGCTGTTGGAGTCTGGGGGAGGCTTGGTACAGCCT GGGGGGTCCCTGAGACTCTCCTGTGCAGCCTCTGGATTCACC TTTAGCGGCTATGCCATGAGCTGGGTCCGCCAGGCTCCAGGG AAGGGGCTGGAGTGGGTCTCAGAGATTGCGCCGCCTGGTTTG AATACACGTTACGCAGACTCCGTGAAGGGCCGGTTCACTATC TCCAGAGACAATTCCAAGAACACGCTGTATCTGCAAATGAAC AGCCTGAGAGCCGAGGACACGGCCGTATATTACTGTGCGAAA TCGGATACTGCTTTTGACTACTGGGGCCAGGGAACCCTGGTC ACCGTCTCGAGCGGTGGAGGCGGTTCAGGCGGAGGTGGCAGC GGCGGTGGCGGGTCGACGGACATCCAGATGACCCAGTCTCCA TCCTCCCTGTCTGCATCTGTAGGAGACAGAGTCACCATCACT TGCCGGGCAAGTCAGAGCATTAGCAGCTATTTAAATTGGTAT CAGCAGAAACCAGGGAAAGCCCCTAAGCTCCTGATCTATCTG GCATCCAATTTGCAAAGTGGGGTCCCATCAAGGTTCAGTGGC AGTGGATCTGGGACAGATTTCACTCTCACCATCAGCAGTCTG CAACCTGAAGATTTTGCAACTTACTACTGTCAACAGGCGGAG TATATGCCTCTGACGTTCGGCCAAGGGACCAAGGTGGAAATC AAACGGGCC (SEQ ID NO: 6) | | |

In yet another embodiment, the antigen binding protein is an anti-CCND1 antibody or fragment thereof that comprises the amino acid sequence of one of SEQ ID NOs: 8 or 10 and specifically binds to a peptide with the amino acids sequence RLTRFLSRV (SEQ ID NO: 7) in conjunction with HLA-A2. In other embodiments, the anti-CCND1 antibody is a scFv-Fc fusion or full length human IgG with VH and VL regions or CDRs selected from Tables 3 and 4.

TABLE 3

| Antigen Peptide CDRs | CCND1 RLTRFLSRV (SEQ ID NO: 7) | | |
|---|---|---|---|
| | 1 | 2 | 3 |
| VH | SYAMS (SEQ ID NO: 38) | TISDSDATDY ADSVKG (SEQ ID NO: 42) | TTDYFDY (SEQ ID NO: 50) |
| VL | RASQSIS SYLN (SEQ ID NO: 56) | YASYLQS (SEQ ID NO: 59) | QQSSSSPDT (SEQ ID NO: 66) |
| Full VH | EVQLLESGGGLVQPGGSLRLSCATSGFTFSSYAMSWVRQAPGK GLEWVSTISDSDATDYADSVKGRFTISRDNSKNTLYLQMNSLR AEDTAVYYCAKTTDYFDYWGQGTLVTVS (SEQ ID NO: 26) | | |
| Full VL | STDIQMTQSPSSLSASVGDRVTITCRASQSISSYLNWYQQKPG KAPKLLIYYASYLQSGVPSRFSGSGSGTDFTLTISSLCIPEDF ATYYCQQSSSSPDTFGQGTKVEIKRAA (SEQ ID NO: 27) | | |
| scFv clone 5, 17 | EVQLLESGGGLVQPGGSLRLSCATSGFTFSSYAMSWVRQAPGK GLEWVSTISDSDATDYADSVKGRFTISRDNSKNTLYLQMNSLR AEDTAVYYCAKTTDYFDYWGQGTLVTVSSGGGGSGGGGSGGGG STDIQMTQSPSSLSASVGDRVTITCRASQSISSYLNWYQQKPG KAPKLLIYYASYLQSGVPSRFSGSGSGTDFTLTISSLQPEDFA TYYCQQSSSSPDTFGQGTKVEIKRAA (SEQ ID NO: 8) | | |
| DNA (5'-3') | GAGGTGCAGCTGTTGGAGTCTGGGGGAGGCTTGGTACAGCCTG GGGGGTCCCTGAGACTCTCCTGTGCAACCTCTGGATTCACCTT TAGCAGCTATGCCATGAGCTGGGTCCGCCAGGCTCCAGGGAAG GGGCTGGAGTGGGTCTCAACTATTTCTGATAGTGATGCTACAG ATTACGCAGACTCCGTGAAGGGCAGGTTCACCATCTCCAGAGA CAATTCCAAGAACACGCTGTATCTGCAAATGAACAGCCTGAGA GCCGAGGACACGGCCGTATATTACTGTGCGAAAACTACTGATT ATTTTGACTACTGGGGCCAGGGAACCCTGGTCACCGTCTCGAG CGGTGGAGGCGGTTCAGGCGGAGGTGGCAGCGGCGGTGGCGGG TCGACGGACATCCAGATGACCCAGTCTCCATCCTCCCTGTCTG CATCTGTAGGAGACAGAGTCACCATCACTTGCCGGGCAAGTCA GAGCATTAGCAGCTATTTAAATTGGTATCAGCAGAAACCAGGG AAAGCCCCTAAGCTCCTGATCTATTATGCATCCTATTTGCAAA GTGGGGTCCCATCAAGGTTCAGTGGCAGTGGATCTGGGACAGA TTTCACTCTCACCATCAGCAGTCTGCAACCTGAAGATTTTGCA ACTTACTACTGTCAACAGTCTTCTAGTTCTCCTGATACGTTCG GCCAAGGGACCAAGGTGGAAATCAAACGGGCGGCC (SEQ ID NO: 9) | | |

TABLE 4

| Antigen Peptide CDRs: | CCND1 RLTRFLSRV (SEQ ID NO: 7) | | |
|---|---|---|---|
| | 1 | 2 | 3 |
| VH | SYAMS (SEQ ID NO: 38) | DISDDGDATYY ADSVKG (SEQ ID NO: 43) | SSTTFDY (SEQ ID NO: 51) |
| VL | RASQSISS YLN (SEQ ID NO: 56) | AASALQS (SEQ ID NO: 60) | QQGTDSPAT (SEQ ID NO: 67) |
| Full VH | EVCILLESGGGLVQPGGSLRLSCAASGFTFSSYAMSWVRQAP GKGLEWVSDISDDGDATYYADSVKGRFTISRDNSKNTLYLQM NSLRAEDTAVYYCAKSSTTFDYWGQGTLVTVS (SEQ ID NO: 28) | | |
| Full VL | STDIQMTQSPSSLSASVGDRVTITCRASQSISSYLNWYQQKP GKAPKLLIYAASALQSGVPSRFSGSGSGTDFTLTISSLQPED FATYYCQQGTDSPATFGQGTKVEIKRAA (SEQ ID NO: 29) | | |
| scFv clone 43 | EVCILLESGGGLVQPGGSLRLSCAASGFTFSSYAMSWVRQAP GKGLEWVSDISDDGDATYYADSVKGRFTISRDNSKNTLYLQM NSLRAEDTAVYYCAKSSTTFDYWGQGTLVTVSSGGGGSGGGG SGGGGSTDIQMTQSPSSLSASVGDRVTITCRASQSISSYLNW | | |

TABLE 4-continued

| Antigen Peptide CDRs: | CCND1 RLTRFLSRV (SEQ ID NO: 7) | | |
|---|---|---|---|
| | 1 | 2 | 3 |
| | YQQKPGKAPKLLIYAASALQSGVPSRFSGSGSGTDFTLTISS LQPEDFATYYCQQGTDSPATFGQGTKVEIKRAA (SEQ ID NO: 10) | | |
| DNA (5'-3') | GAGGTGCAGCTGTTGGAGTCTGGGGGAGGCTTGGTACAGCCT GGGGGGTCCCTGAGACTCTCCTGTGCAGCCTCTGGATTCACC TTTAGCAGCTATGCCATGAGCTGGGTCCGCCAGGCTCCAGGG AAGGGGCTGGAGTGGGTCTCAGATATTTCTGATGATGGTGAT GCTACATATTACGCAGACTCCGTGAAGGGCAGGTTCACCATC TCCAGAGACAATTCCAAGAACACGCTGTATCTGCAAATGAAC AGCCTGAGAGCCGAGGACACGGCCGTATATTACTGTGCAAAA TCTTCTACTACTTTTGACTACTGGGGCCAGGGAACCCTGGTC ACCGTCTCGAGCGGTGGAGGCGGTTCAGGCGGAGGTGGCAGC GGCGGTGGCGGGTCGACGGACATCCAGATGACCCAGTCTCCA TCCTCCCTGTCTGCATCTGTAGGAGACAGAGTCACCATCACT TGCCGGGCAAGTCAGAGCATTAGCAGCTATTTAAATTGGTAT CAGCAGAAACCAGGGAAAGCCCCTAAGCTCCTGATCTATGCT GCATCCGCCTTGCAAAGTGGGGTCCCATCAAGGTTCAGTGGC AGTGGATCTGGGACAGATTTCACTCTCACCATCAGCAGTCTG CAACCTGAAGATTTTGCAACTTACTACTGTCAACAGGGTACT GATAGTCCTGCTACGTTCGGCCAAGGGACCAAGGTGGAAATC AAACGGGCGGCC (SEQ ID NO: 11) | | |

In yet another embodiment, the antigen binding protein is an anti-HUD antibody or fragment thereof that comprises the amino acid sequence of one of SEQ ID NOs: 13, 14 and 17 and has an antigen-binding region that specifically binds to a peptide with the amino acid sequence RIITSTILV (SEQ ID NO: 12) in conjunction with HLA-A2. In other embodiments, the anti-HUD antibody is a scFv-Fc fusion protein or full length human IgG with VH and VL regions or CDRs selected from Tables 5-7.

TABLE 5

| Antigen Peptide CDRs: | HUD RIITSTILV (SEQ ID NO: 12) | | |
|---|---|---|---|
| | 1 | 2 | 3 |
| VH | SYAMS (SEQ ID NO: 38) | DIASTGYYTDY ADSVKG (SEQ ID NO: 44) | NNASFDY (SEQ ID NO: 52) |
| VL | RASQSISS YLN (SEQ ID NO: 56) | DASTLQS (SEQ ID NO: 61) | QQTDSYP TT (SEQ ID NO: 68) |
| Full VH | EVQLLESGGGLVQPGGSLRLSCAASGFTFSSYAMSWVRQA PGKGLEWVSDIASTGYYTDYADSVKGRFTISRDNSKNTLY LQMNSLRAEDTAVYYCAKNNASFDYWGQGTLVTVS (SEQ ID NO: 30) | | |
| Full VL | STDIQMTQSPSSLSASVGDRVTITCRASQSISSYLNWYQQ KPGKAPKLLIYDASTLQSGVPSRFSGSGSGTDFTLTISSL QPEDFATYYCQQTDSYPTTFGQGTKVEIKR (SEQ ID NO: 31) | | |
| scFv clone H128 | EVQLLESGGGLVQPGGSLRLSCAASGFTFSSYAMSWVRQA PGKGLEWVSDIASTGYYTDYADSVKGRFTISRDNSKNTLY LQMNSLRAEDTAVYYCAKNNASFDYWGQGTLVTVSSGGGG SGGGGSGGGGSTDIQMTQSPSSLSASVGDRVTITCRASQS ISSYLNWYQQKPGKAPKLLIYDASTLQSGVPSRFSGSGSG TDFTLTISSLQPEDFATYYCQQTDSYPTTFGQGTKVEIKR (SEQ ID NO: 13) | | |
| DNA (5'-3') | GAGGTGCAGCTGTTGGAGTCTGGGGGAGGCTTGGTACAGC CTGGGGGGTCCCTGAGACTCTCCTGTGCAGCCTCTGGATT CACCTTTAGCAGCTATGCCATGAGCTGGGTCCGCCAGGCT CCAGGGAAGGGGCTGGAGTGGGTCTCGGATATTGCTTCTA | | |

TABLE 5-continued

| Antigen Peptide CDRs: | HUD RIITSTILV (SEQ ID NO: 12) | | |
|---|---|---|---|
| | 1 | 2 | 3 |
| | CTGGTTATTATACAGATTACGCAGACTCCGTGAAGGGCCG GTTCACCATCTCCAGAGACAATTCCAAGAACACGCTGTAT CTGCAAATGAACAGCCTGAGAGCCGAGGACACGGCCGTAT ATTACTGTGCGAAAAATAATGCTAGTTTTGACTACTGGGG CCAGGGAACCCTGGTCACCGTCTCGAGCGGTGGAGGCGGT TCAGGCGGAGGTGGCAGCGGCGGTGGCGGGTCGACGGACA TCCAGATGACCCAGTCTCCATCCTCCCTGTCTGCATCTGT AGGAGACAGAGTCACCATCACTTGCCGGGCAAGTCAGAGC ATTAGCAGCTATTTAAATTGGTATCAGCAGAAACCAGGGA AAGCCCCTAAGCTCCTGATCTATGATGCATCCACTTTGCA AAGTGGGGTCCCATCAAGGTTCAGTGGCAGTGGATCTGGG ACAGATTTCACTCTCACCATCAGCAGTCTGCAACCTGAAG ATTTTGCAACTTACTACTGTCAACAGACTGATTCTTATCC TACTACGTTCGGCCAAGGGACCAAGGTGGAAATCAAACGG (SEQ ID NO: 15) | | |

TABLE 6

| Antigen Peptide CDRs: | HUD RIITSTILV (SEQ ID NO: 12) | | |
|---|---|---|---|
| | 1 | 2 | 3 |
| VH | SYAMS (SEQ ID NO: 38) | SISSSGYYTD YADSVKG (SEQ ID NO: 45) | SASSFDY (SEQ ID NO: 53) |
| VL | RASQSIS SYLN (SEQ ID NO: 56) | DASTLQS (SEQ ID NO: 61) | QQDDAYP TT (SEQ ID NO: 69) |
| Full VH | EVQLLESGGGLVQPGGSLRLSCAASGFTFSSYAMSWVRQA PGKGLEWVSSISSSGSYTDYADSVKGRFTISRDNSKNTLY LQMNSLRAEDTAVYYCAKSASSFDYWGQGTLVTVS (SEQ ID NO: 32) | | |
| Full VL | STDIQMTQSPSSLSASVGDRVTITCRASQSISSYLNWYQQ KPGKAPKLLIYDASTLQSGVPSRFSGSGSGTDFTLTISSL QPEDFATYYCQQDDAYPTTFGQGTKVEIKR (SEQ ID NO: 33) | | |
| scFv clone H78 | EVQLLESGGGLVQPGGSLRLSCAASGFTFSSYAMSWVRQA PGKGLEWVSSISSSGSYTDYADSVKGRFTISRDNSKNTLY LQMNSLRAEDTAVYYCAKSASSFDYWGQGTLVTVSSGGGG SGGGGSGGGGSTDIQMTQSPSSLSASVGDRVTITCRASQS ISSYLNWYQQKPGKAPKLLIYDASTLQSGVPSRFSGSGSG TDFTLTISSLQPEDFATYYCQQDDAYPTTFGQGTKVEIKR (SEQ ID NO: 14) | | |
| DNA (5'-3') | GAGGTGCAGCTGTTGGAGTCTGGGGGAGGCTTGGTACAGC CTGGGGGGTCCCTGAGACTCTCCTGTGCAGCCTCTGGATT CACCTTTAGCAGCTATGCCATGAGCTGGGTCCGCCAGGCT CCAGGGAAGGGGCTGGAGTGGGTCTCATCTATTAGTAGTT CTGGTAGTTATACAGATTACGCAGACTCCGTGAAGGGCCG GTTCACCATCTCCAGAGACAATTCCAAGAACACGCTGTAT CTGCAAATGAACAGCCTGAGAGCCGAGGACACGGCCGTAT ATTACTGTGCGAAATCTGCTTCTTTTGACTACTGGGG CCAGGGAACCCTGGTCACCGTCTCGAGCGGTGGAGGCGGT TCAGGCGGAGGTGGCAGCGGCGGTGGCGGGTCGACGGACA TCCAGATGACCCAGTCTCCATCCTCCCTGTCTGCATCTGT AGGAGACAGAGTCACCATCACTTGCCGGGCAAGTCAGAGC ATTAGCAGCTATTTAAATTGGTATCAGCAGAAACCAGGGA AAGCCCCTAAGCTCCTGATCTATGATGCATCCACTTTGCA AAGTGGGGTCCCATCAAGGTTCAGTGGCAGTGGATCTGGG ACAGATTTCACTCTCACCATCAGCAGTCTGCAACCTGAAG ATTTTGCAACTTACTACTGTCAACAGGATGATGCTTATCC TACTACGTTCGGCCAAGGGACCAAGGTGGAAATCAAACGG (SEQ ID NO: 16) | | |

TABLE 7

| Antigen Peptide CDRs: | HUD RIITSTILV (SEQ ID NO: 12) | | |
|---|---|---|---|
| | 1 | 2 | 3 |
| VH | SYAMS (SEQ ID NO: 38) | SISSDGSYTDY ADSVKG (SEQ ID NO: 46) | STDAFDY (SEQ ID NO: 54) |
| VL | RASQSISS YLN (SEQ ID NO: 56) | AASYLQS (SEQ ID NO: 62) | QQDNNY PTT (SEQ ID NO: 70) |
| Full VH | EVQLLESGGGLVQPGGSLRLSCAASGFTFSSYAMSWVRQA PGKGLEWVSSISSDGSYTDYADSVKGRFTISRDNSKNTLY LQMNSLRAEDTAVYYCAKSTDAFDYWGQGTLVTVS (SEQ ID NO: 34) | | |
| Full VL | STDIQMTQSPSSLSASVGDRVTITCRASQSISSYLNWYQQ KPGKAPKLLIYAASYLQSGVPSRFSGSGSGTDFSLTISSL QPEDFATYYCQQDNNYPTTFGQGTKVEIKR (SEQ ID NO: 35) | | |
| scFv clone H110 | EVQLLESGGGLVQPGGSLRLSCAASGFTFSSYAMSWVRQA PGKGLEWVSSISSDGSYTDYADSVKGRFTISRDNSKNTLY LQMNSLRAEDTAVYYCAKSTDAFDYWGQGTLVTVSSGGGG SGGGGSGGGGSTDIQMTQSPSSLSASVGDRVTITCRASQS ISSYLNWYQQKPGKAPKLLIYAASYLQSGVPSRFSGSGSG TDFSLTISSLQPEDFATYYCQQDNNYPTTFGQGTKVEIKR (SEQ ID NO: 17) | | |
| DNA (5'-3') | GAGGTGCAGCTGTTGGAGTCTGGGGGAGGCTTGGTACAGC CTGGGGGGTCCCTGAGACTCTCCTGTGCAGCCTCTGGATT CACCTTTAGCAGCTATGCCATGAGCTGGGTCCGCCAGGCT CCAGGGAAGGGGCTGGAGTGGGTCTCAAGTATTTCTTCTG ATGGTAGTTATACAGATTACGCAGACTCCGTGAAGGGCCG GTTCACCATCTCCAGAGACAATTCCAAGAACACGCTGTAT CTGCAAATGAACAGCCTGAGAGCCGAGGACACGGCCGTAT ATTACTGTGCGAAATCTACTGATGCTTTTGACTACTGGGG CCAGGGAACCCTGGTCACCGTCTCGAGCGGTGGAGGCGGT TCAGGCGGAGGTGGCAGCGGCGGTGGCGGGTCGACGGACA TCCAGATGACCCAGTCTCCATCCTCCCTGTCTGCATCTGT AGGAGACAGAGTCACCATCACTTGCCGGGCAAGTCAGAGC ATTAGCAGCTATTTAAATTGGTATCAGCAGAAACCAGGGA AAGCCCCTAAGCTCCTGATCTATGCTGCATCCTATTTGCA AAGTGGGGTCCCATCAAGGTTCAGTGGCAGTGGATCTGGG ACAGATTTCTCTCTCACCATCAGCAGTCTGCAACCTGAAG ATTTTGCAACTTACTACTGTCAACAGGATAATAATTATCC TACTACGTTCGGCCAAGGGACCAAGGTGGAAATCAAACGG (SEQ ID NO: 18) | | |

In yet another embodiment, the antigen binding protein is an anti-cdr2 antibody or fragment thereof that comprises the amino acid sequence of SEQ ID NO: 20 and specifically binds to a peptide with amino acids LLEEMFLTV (SEQ ID NO: 19) in conjunction with HLA-A2. In other embodiments, the anti-cdr2 antibody is a scFv-Fc fusion protein or full length human IgG with VH and VL regions or CDRs selected from Table 8.

TABLE 8

| Antigen Peptide CDRs: | cdr2 LLEEMFLTV (SEQ ID NO: 19) | | |
|---|---|---|---|
| | 1 | 2 | 3 |
| VH | SYAMS (SEQ ID NO: 38) | TINYSGSGTTY ADSVKG (SEQ ID NO: 47) | NAAYFDY (SEQ ID NO: 55) |
| VL | RASQSIS SYLN (SEQ ID NO: 56) | GASGLQS (SEQ ID NO: 63) | QQSANAP TT (SEQ ID NO: 71) |
| Full VH | EVQLLESGGGLVQPGGSLRLSCAASGFTFSSYAMSWVRQAPG KGLEWVSTINYSGSGTTYADSVKGRFTISRDNSKNTLYLQMN SLRAEDTAVYYCAKNAAYFDYWGQGTLVTVS (SEQ ID NO: 36) | | |
| Full VL | STDIQMTQSPSSLSASVGDRVTITCRASQSISSYLNWYQQKP GKAPKLLIYGASGLQSGVPSRFSGSGSGTDFTLTISSLQPED FATYYCQQSANAPTTFGQGTKVEIKR (SEQ ID NO: 37) | | |
| scFv clone L9 | EVQLLESGGGLVQPGGSLRLSCAASGFTFSSYAMSWVRQAPG KGLEWVSTINYSGSGTTYADSVKGRFTISRDNSKNTLYLQMN SLRAEDTAVYYCAKNAAYFDYWGQGTLVTVSSGGGGSGGGGS GGGGSTDIQMTQSPSSLSASVGDRVTITCRASQSISSYLNWY QQKPGKAPKLLIYGASGLQSGVPSRFSGSGSGTDFTLTISSL QPEDFATYYCQQSANAPTTFGQGTKVEIKR (SEQ ID NO: 20) | | |
| DNA (5'-3') | GAGGTGCAGCTGTTGGAGTCTGGGGGAGGCTTGGTACAGCCT GGGGGGTCCCTGAGACTCTCCTGTGCAGCCTCTGGATTCACC TTTAGCAGCTATGCCATGAGCTGGGTCCGCCAGGCTCCAGGG AAGGGGCTGGAGTGGGTCTCAACTATTAATTATTCTGGTTCT GGTACAACTTACGCAGACTCCGTGAAGGGCAGGTTCACCATC TCCAGAGACAATTCCAAGAACACGCTGTATCTGCAAATGAAC AGCCTGAGAGCCGAGGACACGGCCGTATATTACTGTGCGAAA AATGCTGCTTATTTTGACTACTGGGGCCAGGGAACCCTGGTC ACCGTCTCGAGCGGTGGAGGCGGTTCAGGCGGAGGTGGCAGC GGCGGTGGCGGGTCGACGGACATCCAGATGACCCAGTCTCCA TCCTCCCTGTCTGCATCTGTAGGAGACAGAGTCACCATCACT TGCCGGGCAAGTCAGAGCATTAGCAGCTATTTAAATTGGTAT CAGCAGAAACCAGGGAAAGCCCCTAAGCTCCTGATCTATGGT GCATCCGGTTTGCAAAGTGGGGTCCCATCAAGGTTCAGTGGC AGTGGATCTGGGACAGATTTCACTCTCACCATCAGCAGTCTG CAACCTGAAGATTTTGCAACTTACTACTGTCAACAGTCTGCT AATGCTCCTACTACGTTCGGCCAAGGGACCAAGGTGGAAATC AAACGG (SEQ ID NO: 21) | | |

Embodiments of the antigen-binding proteins of the disclosure in accordance with Tables 1-8 include, but are not limited to the following:

an anti-WT-1 antibody which binds to an HLA-restricted peptide RMFPNAPYL (SEQ ID NO: 1) comprising: (i) an HVR-L1 sequence of RASQSISSYLN (SEQ ID NO: 56) (ii) an HVR-L2 sequence of SASQLQS (SEQ ID NO: 57) (iii) an HVR-L3 sequence of QQGPGTPNT (SEQ ID NO: 64) (iv) an HVR-H1 sequence of SYAMS (SEQ ID NO: 38) (v) an HVR-H2 sequence of QIDPWGQETLYADSVKG (SEQ ID NO: 40), and (vi) an HVR-H3 sequence of LTGRFDY (SEQ ID NO: 48);

an anti-EBNA3C antibody which binds to HLA-A2 restricted peptide LLDFVRFMGV (SEQ ID NO: 4) comprising: (i) an HVR-L1 sequence of RASQSISSYLN (SEQ ID NO: 56) (ii) an HVR-L2 sequence of LASNLQS (SEQ ID NO: 58) (iii) an HVR-L3 sequence of QQAEYMPLT (SEQ ID NO: 65) (iv) an HVR-H1 sequence of GYAMS (SEQ ID NO: 39) (v) an HVR-H2 sequence of EIAPPGLN-TRYADSVKG (SEQ ID NO: 41), and (vi) an HVR-H3 sequence of SDTAFDY (SEQ ID NO: 49);

an anti-CCND1 antibody which binds to HLA-A2 restricted peptide RLTRFLSRV (SEQ ID NO: 7) comprising: (i) an HVR-L1 sequence of RASQSISSYLN (SEQ ID NO: 56) (ii) an HVR-L2 sequence of YASYLQS (SEQ ID NO: 59) (iii) an HVR-L3 sequence of QQSSSSPDT (SEQ ID NO: 66) (iv) an HVR-H1 sequence of SYAMS (SEQ ID NO: 38) (v) an HVR-H2 sequence of TISDSDATDYADS-VKG (SEQ ID NO: 42), and (vi) an HVR-H3 sequence of TTDYFDY (SEQ ID NO: 50);

an anti-CCND1 antibody which binds to HLA-A2 restricted peptide RLTRFLSRV (SEQ ID NO: 7) comprising: (i) an HVR-L1 sequence of RASQSISSYLN (SEQ ID NO: 56) (ii) an HVR-L2 sequence of AASALQS (SEQ ID NO: 60) (iii) an HVR-L3 sequence of QQGTDSPAT (SEQ ID NO: 67) (iv) an HVR-H1 sequence of SYAMS (SEQ ID NO: 38) (v) an HVR-H2 sequence of DISDDGDATYY-ADSVKG (SEQ ID NO: 43), and (vi) an HVR-H3 sequence of SSTTFDY (SEQ ID NO: 51);

an anti-HUD antibody which binds to HLA-A2 restricted peptide RIITSTILV (SEQ ID NO: 12) comprising: (i) an HVR-L1 sequence of RASQSISSYLN (SEQ ID NO: 56) (ii) an HVR-L2 sequence of DASTLQS (SEQ ID NO: 61) (iii) an HVR-L3 sequence of QQTDSYPTT (SEQ ID NO: 68) (iv) an HVR-H1 sequence of SYAMS (SEQ ID NO: 38) (v) an HVR-H2 sequence of DIASTGYYTDYADSVKG (SEQ ID NO: 44), and (vi) an HVR-H3 sequence of NNASFDY (SEQ ID NO: 52);

an anti-HUD antibody which binds to HLA-A2 restricted peptide RIITSTILV (SEQ ID NO: 12) comprising: (i) an HVR-L1 sequence of RASQSISSYLN (SEQ ID NO: 56) (ii) an HVR-L2 sequence of DASTLQS (SEQ ID NO: 61) (iii) an HVR-L3 sequence of QQDDAYPTT (SEQ ID NO: 69) (iv) an HVR-H1 sequence of SYAMS (SEQ ID NO: 38) (v) an HVR-H2 sequence of SISSSGYYTDYADSVKG (SEQ ID NO: 45), and (vi) an HVR-H3 sequence of SASSFDY (SEQ ID NO: 53);

an anti-HUD antibody which binds to HLA-A2 restricted peptide RIITSTILV (SEQ ID NO: 12) comprising: (i) an HVR-L1 sequence of RASQSISSYLN (SEQ ID NO: 56) (ii) an HVR-L2 sequence of AASYLQS (SEQ ID NO: 62) (iii) an HVR-L3 sequence of QQDNNYPTT (SEQ ID NO: 70) (iv) an HVR-H1 sequence of SYAMS (SEQ ID NO: 38) (v) an HVR-H2 sequence of SISSDGSYTDYADSVKG (SEQ ID NO: 46), and (vi) an HVR-H3 sequence of STDAFDY (SEQ ID NO: 54); and an anti-cdr2 antibody which binds to HLA-A2 restricted peptide LLEEMFLTV (SEQ ID NO: 19) comprising: (i) an HVR-L1 sequence of RASQSISSYLN (SEQ ID NO: 56) (ii) an HVR-L2 sequence of GASGLQS (SEQ ID NO: 63) (iii) an HVR-L3 sequence of QQSANAPTT (SEQ ID NO: 71) (iv) an HVR-H1 sequence of SYAMS (SEQ ID NO: 38) (v) an HVR-H2 sequence of TINYSGSGTTYADSVKG (SEQ ID NO: 47), and (vi) an HVR-H3 sequence of NAAYFDY (SEQ ID NO: 55).

EXAMPLES

General Procedures

Example 1

Production of Biotinylated MHC-Peptide Complexes

Soluble MHC class I/peptide complexes were generated by overexpression of the HLA-A2 heavy chain (HC) and $\beta2$ microglobulin ($\beta_2$M) as recombinant proteins in *E. coli* and subsequent in vitro refolding and assembly in the presence of high concentrations of specific peptide (35, 36). To obtain soluble MHC/peptide complexes the HC sequence was mutagenized to remove the cytosolic and transmembrane regions. In order to specifically biotinylate refolded, monomeric MHC/peptide complexes, the HC was expressed as a fusion protein containing a specific biotinylation site at the C-terminus (37, 38). These short sequences are sufficient for enzymatic in vitro biotinylation of a single lysine residue within this sequence using the biotin protein ligase BirA (39). This procedure was carried out by the MSKCC Tetramer Core Facility.

Example 2

Selection of Phage on Biotinylated MHC-Peptide Complexes

Ex. 2.1

Selection of Phage on HLA-A2/EBNA3C (EBNA) Complex

The Tomlinson I+J human scFv phage display libraries (40), containing approximately $2.85 \times 10^8$ independent scFv clones, were used for selection according to previously published methods (22) with modifications. $7.5 \times 10^{12}$ Phage, from the combination of both libraries, were first preincubated with streptavidin paramagnetic DYNABEADS (30 µl; Dynal, Oslo, Norway) and 150 µg unbiotinylated HLA-A2-YVDPVITSI (SEQ ID NO: 75) (irrelevant complex) in 1 ml of PBS to remove any phage which expressed an antibody that binds to streptavidin or the general framework of HLA-A2.

The DYNABEADS were subsequently captured using a magnet and the supernatant (phage and irrelevant complex mixture) transferred to a separate tube containing 7.5 µg of biotinylated HLA-A2-LLDFVRFMGV (SEQ ID NO: 4) (Epstein-Barr virus EBNA3C-derived) and 7.5 µg of biotinylated HLA-A2-NLVPMVATV (SEQ ID NO: 73) (Cytomedullovirus pp65-derived) and incubated at RT for 1 hour. The final mixture (1 ml) was then added to 200 µl of DYNABEADS (preincubated with 2% Milk and washed with PBS) and the contents were mixed for 15 min. at RT with continuous rotation. The beads were then washed 10 times with PBS/0.1% TWEEN and 3 times with PBS and the bound phage were eluted from the DYNABEADS using 1 mg/ml trypsin in PBS (0.5 ml) for 15 min. at RT.

The phage were then used to infect TG1 *E. coli* (growing in log phase) at 37° C. in 20 ml of LB for 1 hour. $10^{12}$ KM13 helper phage was subsequently added to the mixture, further incubated for an additional 30 minutes, and the cells pelleted using centrifugation (3000 rpm for 10 min.). The resulting cell pellet was resuspended in 200 ml LB+Ampicillin (100 µg/ml)+Kanamycin (50 µg/ml) and incubated overnight at 30° C.

The following morning, the overnight cultures were centrifuged at 3000 rpm for 15 min. and the supernatant (180 ml) was mixed with polyethylene glycol (PEG) on ice for 1 hour so as to precipitate the amplified phage from the previous round of selection. The PEG/phage mixture was then centrifuged at 3000 rpm for 20 min., and some of the resulting phage pellet used for subsequent rounds of panning while the rest was frozen down in 15% glycerol at −80° C. Subsequent rounds of panning were done using the same protocol as above with an increase in DYNABEADS washing steps and a decrease in the amount of biotinylated complexes used for selection.

After the final round of antibody selection ($3^{rd}$ or 4th round), the eluted phage were used to infect both TG1 and HB2151 *E. coli*; TG1 cells were cultured overnight as mentioned above while the HB2151 cells were plated on TYE+Ampicillin (100 µg/ml) agar plates. The next morning, individual colonies from the agar plate were picked and used to inoculate individual wells of a 48-well plate containing 400 µl LB+Ampicillin (100 µg/ml)/well. After incubation for 3-6 hours at 37° C., 200 µl of 50% glycerol solution was added to each well and the plates stored at −80° C. as monoclonal stock cultures.

Ex. 2.2

Selection of Phage on HLA-A2-RMFPNAPYL (SEQ ID NO: 1) (WT-1) Complex

Selection was done similarly to the method above with slight modifications. $3.7 \times 10^{12}$ Phage from the combination of both libraries, were first preincubated with streptavidin paramagnetic DYNABEADS (50 µl; Dynal, Oslo, Norway) and 20 µg unbiotinylated HLA-A2-NLVPMVATV (SEQ ID NO: 73) (irrelevant complex) in 1 ml of PBS to deplete the streptavidin and HLA-A2 binders. The DYNABEADS were subsequently captured using a magnet and the supernatant (phage and irrelevant complex mixture) transferred to a separate tube containing 5 µg of biotinylated HLA-A2-RMFPNAPYL (SEQ ID NO: 1) (WT1-derived) and incubated at RT for 1 hour. The final mixture (1 ml) was then added to 100 µl of DYNABEADS (preincubated with 2% Milk and washed with PBS) and the contents were mixed for 30 min. at RT with continuous rotation. The beads were then washed 10 times with PBS/0.1% TWEEN and 3 times with PBS and the bound phage were eluted from the DYNABEADS using 1 mg/ml trypsin in PBS (0.5 ml) for 20 min. at RT. All subsequent steps were performed as above.

Example 3

Expression and Purification of Soluble scFv from HB2151

Using the monoclonal glycerol stocks containing individual HB2151 clones, separate 48-well plates containing 400 µl LB+Ampicillin (100 µg/ml)/well were inoculated in a replica-plate type format using sterile pipette tips. The 48-well culture plates were subsequently incubated at 37° C. until the majority of the wells reached an OD600 of 0.4. 200 µl LB+Ampicillin (100 µg/ml)+isopropyl-1-thio-β-D-galactopyranoside (IPTG; 1 mM final concentration) was subsequently added to each well to induce scFv production and the plates were further incubated overnight at 28° C. The next morning, the plates were centrifuged at 3000 rpm for 15 min. and the supernatant used for scFv screening.

For large scale expression and purification, monoclonal glycerol stocks were used to inoculate 3 ml of Terrific Broth (TB) and incubated at 37° C. until an OD600 of 0.8 was reached. Each 3 ml culture was subsequently divided amongst four flasks, each containing 250 ml TB+Ampicillin (100 µg/ml). The cultures were then incubated at 37° C. until an OD600 of 0.4-0.5 was reach, after which IPTG was added to a final concentration of 0.5 mM and the cultures incubated overnight at 30° C. The next morning, the overnight cultures were centrifuged at 4000 rpm for 25 min. The supernatant was discarded and the pellets dissolved in 50 ml PBS+10 mM imidazole. The cell suspensions were passed through a cell homogenizer (5000 pounds per square inch) and the resulting cell lysates were centrifuged at 12,000 rpm for 15 min. The supernatants were then passed over a 0.22 µm filter pre-layered with diatomaceous earth and the resulting filtrates loaded over VIVAPURE maxiprepMC Nickel affinity columns (Sartorius Stedim Biotech, Aubagne, France) using centrifugation (100 rpm for 5 min.). The columns were then washed 4 times using 10 ml PBS+30 mM imidazole (500 rpm for 3 min.) and the scFvs eluted using 20 ml PBS+300 mM imidazole (500 rpm for 3 min.). The eluted scFvs were concentrated using 10,000 molecular weight cut-off membrane VIVASPIN centrifuge tubes at 3000 rpm for 30 min. (Sartorius Stedim Biotech) and dialyzed back into regular PBS. The final scFv products were subsequently stored at −80° C.

Example 4

Construction of scFv-Fc Fusion Protein and Expression in DG44 CHO Cells

Using a proprietary antibody expression vector (referred to herein as IgG Vector), similar to that of pFUSE-hIgG1-Fc1 (InvivoGen; San Diego, Calif.), the construct was first modified to contain the $CH_2$, and $CH_3$ domains of a human $IgG_1$ (scFv-Fc Vector). Subsequently, the EBNA Clone 315 and WT1 Clone 45 scFv sequences were PCR amplified to contain the required NheI and ApaI restriction sites which would be compatible with the scFv-Fc vector. The resulting scFv PCR products and antibody expression plasmid were digested using the above enzymes (NheI at 37° C. for 2 hours and ApaI at 25° C. for 2 hours) and then ligated together. The ligation products were then transformed into E. coli, plated on TYE+Amplicilin (100 µg/ml), colonies were picked and their plasmids sequenced at the MSKCC Sequencing Core Facility. Once the sequences were validated to have the correct scFv sequences upstream of the human $IgG_1$ $CH_2$ and $CH_3$ domains, the DNA (5-6 µg was electroporated (Amaxa NUCLEOFACTOR; Lonza, Switzerland) into $5 \times 10^6$ DG44 Chinese Hamster Ovary (CHO) Cells (Invitrogen) using Program U-030 and 100 µl Solution V. The cells were then cultured in OPTICHO media (Invitrogen) containing G418 (500 µg/ml; added 7 days post-electroporation) at a cell density of $1-5 \times 10^6$ DG44 per ml of media. The cells were then expanded to approximately 700 ml of culture media, which was centrifuged to remove the cells and supernatant used for antibody purification.

Example 5

Expression and Purification of Soluble scFv-Fc Fusion Protein

DG44 supernatant containing the soluble scFv-Fc fusion protein was purified using the KAPPASELECT affinity chromatograph medium (GE Healthcare). First, 1.5 ml of KAPPASELECT resin was loaded onto a column and activated with 20 ml of PBS. The supernatant was loaded onto the column using a peristaltic pump at a flow rate of approximately 1 ml/min. The column was subsequently washed using 40 ml of PBS until the flow-thru registered an OD280 of less than 0.05. The scFv-Fc fusion protein was then eluted from the resin using 10 ml citrate buffer (pH 2.0) and directly into 10 ml of 1 M Tris for neutralization. The eluted scFv-Fc was subsequently concentrated using a 50,000 MWCO VIVASPIN centrifuge tube (Sartorius Stedim) and tested for its ability to bind to recombinant antigen using ELISA and the BIACORE T100 (GE Healthcare) as well as natively presented peptide on the surface of T2 cells using flow cytometry.

Example 6

Monoclonal ELISA with Bacterial Phage Clones and Purified scFv and scFv-Fc

Vinyl flat bottom microtiter plates (Thermo Fisher) were used for ELISA assays. Plates were initially coated overnight at 4° C. with BSA-biotin (10 µg/ml; 50 µl/well). The next morning, the contents were discarded and the plates incubated at RT with streptavidin (10 µg/ml; 50 µl/well) for 1 hour. The contents were discarded and the plates incubated with recombinant biotinylated HLA-A2-peptide complexes (5 µg/ml; 50 µl/well) at RT for 1 hour. The plates were then incubated with 2% Milk (150 µl/well) at RT for 1 hour. After blocking, the plates were washed 2 times with PBS and then incubated with bacterial supernatant from their respective HB2151 culture plate wells, purified scFv, or purified scFv-Fc at RT for 1 hour. The contents were discarded, the plates washed 5 times with PBS, and then incubated at RT for 1 hour with either a mouse-anti-myc tag antibody (Clone 9E10; Sigma Aldrich. 0.5 µg/ml; 100 µl/well in 0.5% Milk) to detect the scFv or a goat-anti-human-HRP (Jackson Immunoresearch Laboratories. 0.5 µg/ml; 100 µl/well in 0.5% Milk) to detect the scFv-Fc. The contents were discarded, the plates washed 5 times with PBS, and those receiving the scFv were further incubated with a goat-anti-mouse-HRP (Jackson Immunoresearch Laboratories. 0.5 µg/ml; 100 µl/well in 0.5% Milk) at RT for 1 hour while the plates receiving the scFv-Fc were developed using o-phenylenediamine (OPD) buffer (150 µl/well), which was made by combining 20 mg of OPD tablets in 40 ml of citrate phosphate buffer with 40 µl 30% hydrogen peroxide. The color reaction was stopped by adding 30 µl of 5N sulfuric acid to each well and the plates read using the Dynex MRX ELISA plate reader at 490 nm. Lastly, the contents of the scFv plates were discarded, the plates washed 5 times with PBS, and developed according to the method above.

Example 7

Cell Lines and Peptides

Tap-deficient HLA-A2$^+$ T2 cells, 6268A, GKO (both HLA-A2$^-$), DIMT and JG19 (both HLA-A2$^+$) B-cell lymphoblastic cell lines (BLCLs) were used for antigen presentation studies. Cells were normally cultured in RPMI 1640+ 10% Fetal Bovine Serum (FBS). For antigen presentation, T2 cells were harvested and transferred to serum-free IMDM+10 µg/ml β2-microglobulin (β2M). The T2 cells would then be incubated with 20 µM or less of either LLDFVRFMGV SEQ ID NO: 4) -peptide (derived from EBNA3C) or any number of irrelavent peptides at 37° C. for 5 hours. Studies with BLCLs were done in the same manner as with T2 cells with the occlusion of β$_2$M in the media. Pulse-Chase experiments with DIMT BLCLs were done by first pulsing the BLCLs in serum-free IMDM with 20 µM LLDFVRFMGV SEQ ID NO: 4) for 5 hours at 37° C. The cells were then washed with fresh RPMI 1640+10% FBS, transferred back into this culture medium and cultured further at 37° C. for 5 and 24 hours, followed by flow cytometric analysis at each time point using EBNA Clone 315 scFv.

Example 8

Binding Kinetics Analysis

Kinetic measurements were performed by surface plasmon resonance using the BIACORE T100 (GE Biosciences). Briefly, the first two flow cells of a CM5 chip (GE Biosciences) were activated using the standard amine coupling reagents in HBS-EP running buffer (0.01 M HEPES, 0.15 M NaCl, 3 mM EDTA, 0.005% TWEEN 20) with flow cell 2 immobilized with the purified EBNA Clone 315 scFv-Fc fusion protein using 10 mM Acetate (pH 5). Subsequently, the target HLA-A2-peptide monomer (222 nM-13.875 nM) was injected over both the 1st (reference) and 2nd flow cells at 20 µl/min. for 120 sec., followed by the addition of running buffer for an extra 180 sec. Kinetics values were determined using the BIACORE T100 Evaluation Software 2.0 and 1:1 binding model (local Rmax).

Example 9

Flow Cytometry

Peptide-pulsed T2 cells and BLCLs were transferred to plastic polystyrene round-bottom tubes (Becton Dickinson Labware) and washed with PBS. The cells were subsequently incubated with 5 µg of either targeted or non-specific purified scFv or scFv-Fc on ice for 40 min. The cells were washed with PBS and then incubated with 1 µg of biotinylated mouse-anti-myc antibody (Clone 9E10; Sigma Aldrich) or biotinylated mouse-anti-human IgG Fc-specific (Jackson Immunoresearch Laboratories) on ice for 30 min. The cells were washed with PBS and then incubated with streptavidin-PE (BD Biosciences). Lastly, the cells were washed once more with PBS and analyzed on the BD FACS Calibur.

For CD107a cytotoxicity assays, transduced-NK92MI cells and target T2 cells were cocultured in a 1:1 effector:target (E:T) ratio (2.5-5.0×10$^5$ cells each) in 200 µl complete Alpha Essential medium (12.5% horse serum and 12.5% FBS) (Invitrogen)+10-15 µl anti-CD107a-PE at 37° C. for 5 Hours. The cell mixture was then washed with PBS and analyzed on the BD FACS Caliber.

For FACS sorting experiments, retrovirally transduced NK92MI cells were sorted based on GFP intensity using the BD Aria Flow Cytometer under the guidence of the MSKCC Flow Cytometry facility.

Example 10

Quantitation of HLA-A2-LLDFVRFMGV SEQ ID NO: 4) Complexes on Peptide-Pulsed T2 Cells For MHC-peptide complex quantitation, the EBNA Clone 315 scFv-Fc was first directly conjugated to ALEXA FLUOR 647 using the APEX ALEXA FLUOR 647 Antibody Labeling Kit (Invitrogen). The kit yields about 10-20 µg of labeled antibody.

For quantitation, the QUANTUM SIMPLY CELLULAR anti-Human IgG kit was used (Bangs Laboratories) along with the technical assistance of Hong-fen Guo in our laboratory. Briefly, the kit is comprised of five microsphere populations; one blank and four labeled with increasing amounts of anti-human IgG. The beads and the peptide pulsed T2 cells (37° C. for 5 hours) were then labeled with the same fluorescently conjugated EBNA Clone 315 scFv-Fc on ice for 30 minutes. The cells were then washed with PBS and analyzed on the BD FACS Calibur along with the labeled beads. The Excel-based QuickCal analysis template that's provided with each kit aids in correlating fluorescence intensity with antigen density on the T2 cells. Each of the 4 data points are the average of duplicates.

Example 11

Construction of the WT-1 Clone 45 Chimeric Antigen Receptor

The original chimeric antigen receptor was obtained from Dr. Dario Campana from St. Jude Children's Hospital and previously described (41). For future compatibility purposes, a scFv-CD3ζ-4-1 BB DNA construct (similar to that seen in the original chimeric immune receptor, with EcoRI and XhoI flanking the 5' and 3' ends) was purchased (pUC57 vector from Genescript; Piscataway, N.J.) and contained an irrelevant scFv flanked by SfiI and NotI. The plasmid containing the EBNA Clone 315 scFv sequence (pIT2 vector from the Tomlinson library) was purified (Qiagen miniprep DNA isolation kit) from overnight culture of the bacterial stock in LB+Amplicilin (100 μg/ml). The scFv sequence was excised from the pIT2 vector using SfiI (50° C. for 2 hours) and NotI (37° C. for 2 hours) inserted into the purchased and predigested (SfiI and NotI) pUC57 vector. After ligation, the product was transformed into NEB 5-alpha competent E. coli (New England Biolabs), the cells plated on TYE+Amplicilin (100 μg/ml), colonies were picked and cultured in LB+Amplicilin (100 μg/ml), their plasmids purified and the product sizes were verified by gel electrophoresis. Plasmids which were found to have the correct ligation products were subsequently excised from the pUC57 vector using EcoRI (37° C. for 2 hours) and XhoI (37° C. for 2 hours) and used for insertion into the vector provided to us by the Campana laboratory. The ligation products were then transformed into E. coli as above, plated on TYE+Amplicilin (100 μg/ml), colonies were picked and their plasmids sequenced using the reverse primer 788A (5'-CCCTTGAACCTCCTCGTTCGACC-3') (SEQ ID NO: 72) at the MSKCC Sequencing Core Facility. Once the sequences were validated, the DNA was packaged into retrovirus and used to infect NK92MI cells.

Example 12

Construction of the EBNA Clone 315 Chimeric Antigen Receptor

Due to compatibility issues, the pUC57 scFv-CD3ζ-4-1 BB DNA construct purchased from Genescript and mentioned above was used to replace the WT1 Clone 45 scFv with the EBNA Clone 315 scFv. First, the plasmid containing the EBNA Clone 315 scFv sequence (pIT2 vector from the Tomlinson library) was purified (Qiagen miniprep DNA isolation kit) from overnight culture of the bacterial stock in LB+Amplicilin (100 μg/ml). The scFv sequence was excised from the pIT2 vector using SfiI (50° C. for 2 hours) and NotI (37° C. for 2 hours) and ligated to the predigested (SfiI and NotI) pUC57 vector. After ligation, the product was transformed into E. coli, colonies were picked, cultured overnight, their plasmids purified and the product sizes verified by gel electrophoresis. Plasmids which were found to have the correct ligation products were subsequently excised from the pUC57 vector using EcoRI (37° C. for 2 hours) and XhoI (37° C. for 1 minute). Due to the presence of a XhoI site inside of the EBNA Clone 315 scFv sequence, the DNA was partially digested with XhoI and then completely digested using EcoRI. This allowed for the isolation of the correct DNA fragment which kept the integrity of the scFv sequence while removing the entire CAR sequence from the pUC57 vector. After insertion into the vector provided to us by the Campana laboratory, the ligation products were then transformed into E. coli as above, plated on TYE+Amplicilin (100 μg/ml), colonies were picked and their plasmids sequenced using the reverse primer 788A (5'-CCCTTGAACCTCCTCGTTCGACC-3') (SEQ ID NO: 72) at the MSKCC Sequencing Core Facility. Once the sequences were validated, the DNA was packaged into retrovirus and used to infect NK92MI cells.

Example 13

Retroviral Production, DNA Packaging, and Infection of NK92MI Cells

To produce CAR-containing retrovirus, the following procedure was employed which used a 293T-based retroviral production cell line (GP2). Briefly, 7 μg of CAR DNA was combined with 3.5 μg of PCLAmpho helper construct and 3.5 μg pVSVg in 1 ml of serum-free DMEM. This mixture was then combined with 1 ml serum-free DMEM containing 36 μl of LIPOFECTAMINE 2000 (Invitrogen) and incubated at RT for 20 min. Afterwards, the DNA-LIPOFECTAMINE complex (2 ml) was mixed with GP2 cells ($3-5 \times 10^6$) in 10 ml of DMEM+10% FBS and cultured at 37° C. for 72 hours. Subsequently, the supernatant (12 ml) was depleted of GP2 cells during recovery and incubated with 3 ml LENTI-X Concentrator solution (Clontech) at 4° C. for 12-16 hours. Afterwards, the solution was centrifuged at 3000 rpm for 15 min., the supernatant discarded, and the pellet dissolved in 1 ml complete Alpha Essential medium containing $5 \times 10^5$ NK92MI cells. The cells were then incubated for 72 hours and checked by flow cytometry for CAR expression via GFP (the CAR gene is expressed under a CMV promoter which is followed by IRES-GFP).

Example 14

Construction of scFv-Fc Fusion Protein and Expression in DG44 CHO Cells

Using a proprietary antibody expression vector similar to that of pFUSE-hIgG1-Fc1 (Invivogen; San Diego, Calif.), the Clone 315 scFv sequence was first PCR amplified to contain the required NheI and ApaI restriction sites. The resulting PCR product and expression plasmid were digested using the above enzymes (NheI at 37° C. for 2 hours and ApaI at 25° C. for 2 hours) and ligated together. The ligation products were then transformed into E. coli, plated on TYE+Amplicilin (100 μg/ml), colonies were picked and their plasmids sequenced at the MSKCC Sequencing Core Facility. Once the sequences were validated to have the Clone 315 scFv sequence upstream of the human IgG$_1$ CH2 and CH3 domains, the DNA was electroporated (Amaxa NUCLEAOFACTOR; Lonza, Switzerland) into $5 \times 10^6$ DG44 Chinese Hamster Ovary (CHO) Cells (Invitrogen) using Program U-030 and 100 μl Solution V. The cells were then cultured in OPTICHO media (Invitrogen) containing G418 (500 μg/ml; added 7 days post-electroporation) at a cell density of $1-5 \times 10^6$ DG44 per ml of media.

Example 15

Retroviral Production, DNA Packaging, and Infection of NK92MI Cells

To produce CAR-containing retrovirus, the following procedure was employed which used a 293T-based retroviral production cell line (GP2). Briefly, 7 μg of CAR DNA was combined with 3.5 μg of PCLAmpho helper construct and 3.5 μg pVSVg in 1 ml of serum-free DMEM. This mixture was then combined with 1 ml serum-free DMEM containing 36 μl of LIPOFECTAMINE 2000 (Invitrogen) and incubated at RT for 20 min. Afterwards, the DNA-LIPO-FECTAMINE complex (2 ml) was mixed with GP2 cells ($3\text{-}5\times10^6$) in 10 ml of DMEM+10% FBS and cultured at 37° C. for 72 hours. Subsequently, the supernatant (12 ml) was depleted of GP2 cells during recovery and incubated with 3 ml LENTI-X Concentrator solution (Clontech) at 4° C. for 12-16 hours. Afterwards, the solution was centrifuged at 3000 rpm for 15 min., the supernatant discarded, and the pellet dissolved in 1 ml complete Alpha Essential medium containing $5\times10^5$ NK92MI cells. The cells were then incubated for 72 hours and checked by flow cytometry for CAR expression via GFP (the CAR gene is expressed under a CMV promoter which is followed by IRES-GFP).

Example 16

$^{51}$Cr Release Cytotoxicity Assay

The capacity of CAR equipped NK92MI cells to lyse BLCLs was evaluated using a $^{51}$Chromium release assay. Briefly, peptide pulsed or unpulsed $^{51}$Cr-labeled BLCLs were plated in round-bottom 96-well plates ($5\times10^3$ cells/well) in RPMI 1640 with 10% FBS. Subsequently, CAR equipped NK92MI cells were added to the BLCL containing wells at different effector (E)/target (T) ratios and incubated for 4 hours at 37° C., after which the cultures were depleted of cells and $^{51}$Cr-release was measured in the supernatants. All E:T ratios were done in triplicate, with the average plotted on the graphs. % $^{51}$Cr Release was determined using the following formula: ((Sample Release−Spontaneous Release)/(Total Release−Spontaneous Release))×100.

Example 17

Affinity Selection of Phage on Virally-Derived Recombinant HLA-A2-Peptide Complexes Biotinylated and non-biotinylated recombinant HLA-A2-peptide complexes presenting various different peptides previously shown to bind to HLA-A2 were obtained from the MSKCC Tetramer Core Facility. For selection purposes, the Tomlinson I and J phage display libraries were combined and first preincubated with non-biotinylated, irrelevant HLA-A2-YVDPVITSI (SEQ ID NO: 75) complex along with streptavidin paramagnetic beads so that any phage which expresses an antibody that may bind to the general framework of HLA-A2, or the streptavidin beads themselves, are eventually discarded during the washing steps. Subsequently, the contents (phage and irrelevant complex) were incubated with biotinylated HLA-A2-LLDFVRFMGV (SEQ ID NO: 4) (EBNA3C) and biotinylated HLA-A2-NLVPMVATV (SEQ ID NO: 73) (pp65) simultaneously in equimolar ratios and captured using streptavidin paramagnetic beads. Once the beads were bound to the biotinylated complexes, the beads were washed with PBS containing TWEEN 20 and the bound phage were eluted from the beads using trypsin. After two additional rounds of selection, the recovered phage were used to infect HB2151 E. coli and plated on ampicillin-containing agar. The next morning, individual colonies were picked, cultured overnight in 48-well culture plates, and their supernatants tested for the presence of scFv on 96-well ELISA plates pre-coated with recombinant HLA-A2-peptide complexes.

The first three rounds of selection resulted in a 55-fold increase in phage recovery, based on output/input ratio, and scFvs which only bound to the HLA-A2-EBNA3C complex. Phage display selection results on recombinant HLA-A2-LLDFVRFMGV (SEQ ID NO: 4) and HLA-A2-NLVPM-VATV (SEQ ID NO: 73) complexes are shown in Table 9.

TABLE 9

|  | Round 1* | Round 2* | Round 3* | Round 4** |
|---|---|---|---|---|
| Input | $7.5 \times 10^{12}$ | $4.9 \times 10^{12}$ | $2.4 \times 10^{12}$ | $1.8 \times 10^{12}$ |
| Output | $4.7 \times 10^{6}$ | $6 \times 10^{6}$ | $8.4 \times 10^{7}$ | $1.25 \times 10^{8}$ |
| Output/Input | $6.3 \times 10^{-7}$ | $1.22 \times 10^{-6}$ | $3.5 \times 10^{-6}$ | $6.9 \times 10^{-5}$ |
| Fold Enrichment (From Rd 1) | — | 2 | 55.5 | 109.5 |
| HLA-A2-EBNA3C Peptide-Specific Clones*** | — | — | 40/48 (83%) | 37/48 (77%) |
| HLA-A2-pp65 Peptide-Specific Clones*** | — | — | 0/48 (0%) | 0/48 (0%) |

*Rd 1-3: Panning against Biotinylated-HLA-A2-pp65 Peptide + Biotinylated-HLA-A2-EBNA Peptide
**Rd 4: Panning against Biotinylated HLA-A2-EBNA3C Peptide Only
***Relative signal at least 2-fold greater than background.

These results were somewhat surprising since both of the peptides on HLA-A2 were derived from viral-related proteins, which are not seen in the human protein repertoire. To confirm these findings, an additional round of selection was undertaken on just the HLA-A2-EBNA3C complex alone which resulted in a further amplification of recovered phage (109-fold) and a similar percentage of clones which bound to the HLA-A2-EBNA3C complex (83% positive after Round 3 and 77% after Round 4).

Bacterial supernatant from individual clones after 3 rounds of phage selection were tested for binding to recombinant, biotinylated-HLA-A2-peptide complexes on vinyl microtiter plates. While several clones resulted in cross-reactivity to more than just the targeted HLA-A2-LLD-FVRFMGV (SEQ ID NO: 4) complex (Clones 335 and 345), Clones 315 and 327 were found to have the desired specificity.

Purified EBNA Clone 315 scFv was retested against a similar panel of recombinant, biotinylated HLA-A2-peptide complexes. Purified EBNA Clone 315 scFv maintained its specificity over a panel of HLA-A2-peptide complex in addition to its inability to bind to the native peptide by itself. The anti-HLA-A2 antibody BB7.2 was included to demonstrate that all HLA-A2-peptide complexes are adherent and presented properly on the plate.

During the screening processes, therefore, several different scFv were found to bind to the targeted HLA-A2-EBNA3C complex, however only a few scFv sequences resulted in absolute specificity and did not bind to HLA-A2-peptide complexes of different origins (FIG. 1A). Of those clones which were tested, EBNA Clones 315 and 327 had the same peptide sequence and were further characterized. After scFv purification, a subsequent validation ELISA demonstrates that EBNA Clone 315 maintained its specificity towards the targeted HLA-A2-EBNA complex, in addition to failing to bind to the LLDFVRFMGV (SEQ ID NO: 4) peptide by itself (FIG. 1B). These initial binding assays demonstrate the TCR-like binding ability of this antibody.

Example 18

Affinity Selection of Phage on WT1-Derived Recombinant HLA-A2-Peptide Complex

Antibody selection using phage against biotinylated HLA-A2-RMFPNAPYL (SEQ ID NO: 1) (WT1-derived)

was done in a similar manner to that which was described above. Briefly, the Tomlinson I and J phage display libraries were first combined and preincubated with non-biotinylated, irrelevant HLA-A2-NLVPMVATV (SEQ ID NO: 73) complex and streptavidin paramagnetic beads. Subsequently, the contents (phage and irrelevant complex) were incubated with biotinylated HLA-A2-RMFPNAPYL (SEQ ID NO: 1) and captured using fresh streptavidin paramagnetic beads. Once bound to the biotinylated complex, the beads were washed with PBS containing TWEEN 20 and the bound phage were eluted from the beads using trypsin. After two additional rounds of selection, the recovered phage were used to infect HB2151 *E. coli* and plated on ampicillin-containing agar. The next morning, individual colonies were picked, cultured overnight in 48-well culture plates, and their supernatants tested for the presence of scFv on 96-well ELISA plates pre-coated with recombinant HLA-A2-peptide complexes.

The first three rounds of selection resulted in a 90-fold enrichment in phage when comparing the output/input ratios. Phage display selection results on recombinant HLA-A2-RMFPNAPYL (SEQ ID NO: 1) complex are shown in Table 10.

TABLE 10

|  | Round 1* | Round 2** | Round 3** |
|---|---|---|---|
| Input | $3.7 \times 10^{12}$ | $5.6 \times 10^{11}$ | $1.55 \times 10^{11}$ |
| Output | $4.0 \times 10^{6}$ | $3.2 \times 10^{6}$ | $1.52 \times 10^{7}$ |
| Output/Input | $1.08 \times 10^{-6}$ | $5.7 \times 10^{-6}$ | $9.8 \times 10^{-5}$ |
| Fold Enrichment (From Rd 1) | — | 5.3 | 90.7 |
| HLA-A2-RMFPNAPYL-Specific Clones*** | — | — | 3/48 |

*Rd 1: Panning against 5 μg Complex.
**Rd 2-3: Panning against 2.5 μg Complex.
***Relative signal at least 3-fold greater than background (Irrelevant HLA-A2-Complex).

Bacterial supernatant from three individual clones after three rounds of phage selection were tested for binding to recombinant, biotinylated-HLA-A2-peptide complexes on vinyl microtiter plates. All three clones which were tested had the necessary specificity to only recognize the HLA-A2-RMFPNAPYL (SEQ ID NO: 1) complex. It was discovered that all three clones had the same DNA sequence. Purified WT1 Clone 45 scFv was retested against a similar panel of recombinant, biotinylated HLA-A2-peptide complexes. Purified WT1 Clone 45 scFv maintained its specificity over a panel of HLA-A2-peptide complex in addition to its inability to bind to the native peptide outside of the context of MHC. The anti-HLA-A2 antibody BB7.2 was included to demonstrate that all HLA-A2-peptide complexes are adherent and presented properly on the plate.

Figure 2:
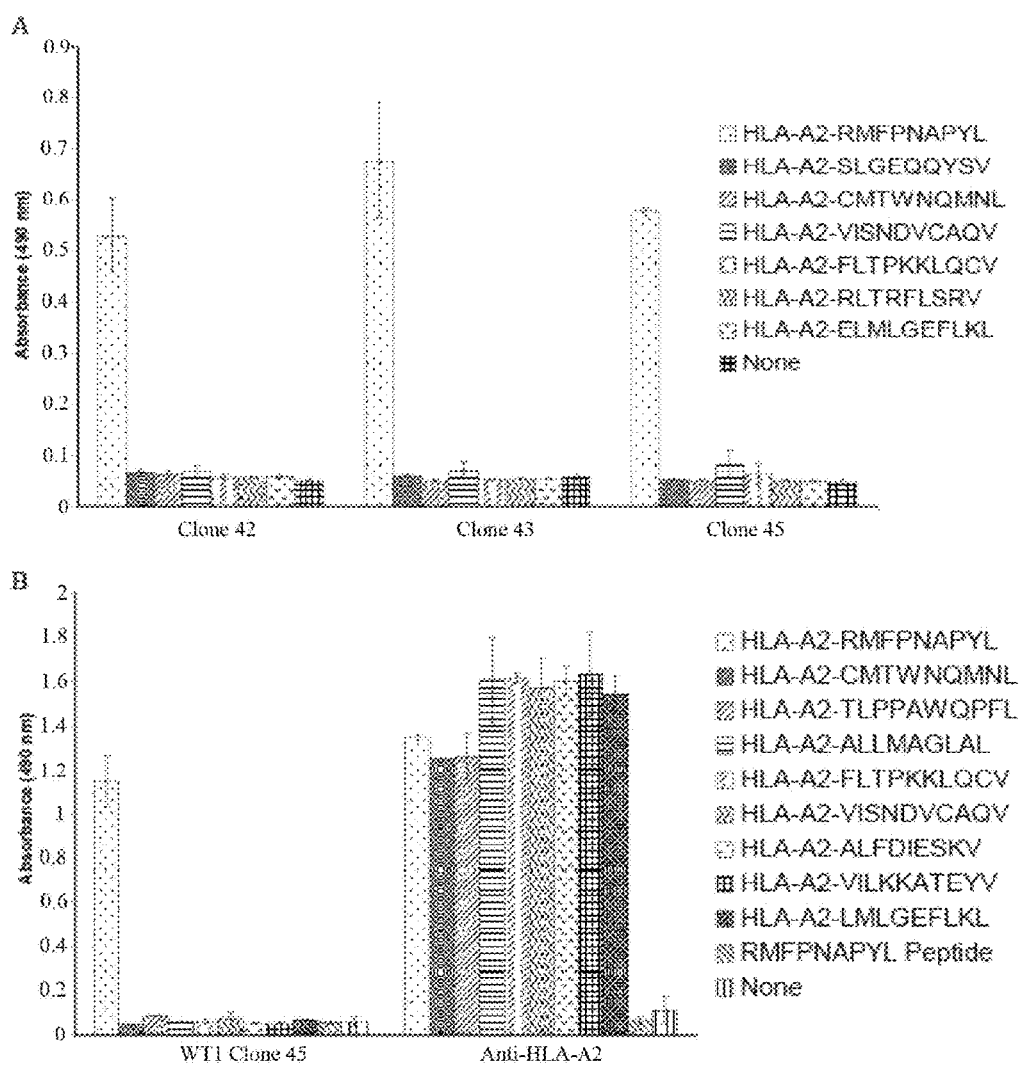
FIG. 2 shows the binding of bacterial supernatant from individual WT-1 scFv clones 42, 43 and 45 (FIG. 2A) and purified WT-1 clone 45 scFv (FIG. 2B) to various HLA-A2-peptide complexes demonstrating that WT-1 clones 42, 43 and 45 are highly specific for the recombinant HLA-A2-RMFPNAPYL (SEQ ID NO: 1) complex.

After screening 48 clones for binding to the specific HLA-A2-RMFPNAPYL complex, therefore, three clones were found to bind specifically to their targeted complex but failed to bind to complexes which displayed an irrelevant peptide (FIG. 2A). Of the clones which were tested, all of them were found to have the same peptide sequence and WT1 Clone 45 was chosen for further characterization. After scFv purification, a subsequent validation ELISA demonstrates that WT1 Clone 45 maintained its specificity towards the targeted HLA-A2-WT1 complex, in addition to failing to bind to the RMFPNAPYL (SEQ ID NO: 1) peptide by itself (FIG. 2B). These initial binding assays demonstrate the TCR-like binding ability of this antibody.

Example 19

Figure 3:
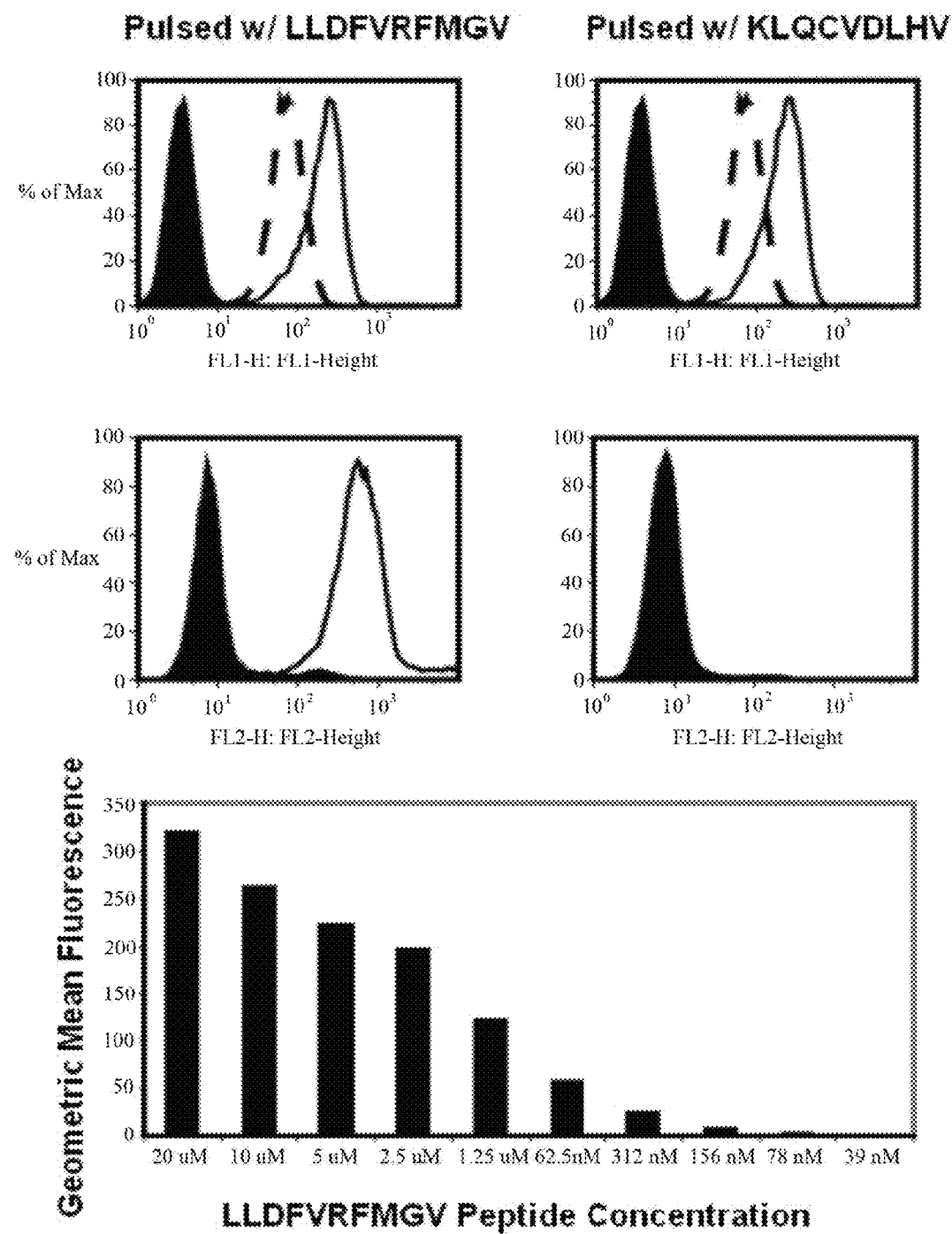
FIG. 3 shows that HLA-A2 can be detected on TAP-deficient (TAP⁻) T2 cells that were either pulsed or unpulsed with LLDFVRFMGV (SEQ ID NO: 4) or another (irrelevant) peptide (FIG. 3A) but that EBNA clone 315 scFv recognizes T2 cells that have been pulsed with LLDFVRF-MGV (SEQ ID NO: 4) but not unpulsed cells or cells pulsed with irrelevant peptide (FIG. 3B) with a lower limit of detection at about 78 nM (FIG. 3C).

Binding and Specificity Studies with Purified EBNA Clone 315 and WT1 Clone 45 scFvs on Peptide-Pulsed T2 Cells To demonstrate that the isolated EBNA Clone 315 and WT1 Clone 45 scFvs are able to recognize and bind to their native complexes on the surface of peptide-pulsed antigen presenting cells (APCs), the TAP-deficient T2 cell line was used. T2 cells were first incubated for 5 hours at 37° C. with either LLDFVRFMGV (SEQ ID NO: 4) (EBNA3C-derived), RMFPNAPYL (SEQ ID NO: 1) (WT1-derived) or irrelevant peptide KLQCVDLHV (SEQ ID NO: 74) in serum-free medium containing $\beta_2M$. The cells were subsequently washed and stained with the purified WT1 Clone 45, EBNA Clone 315 or an irrelevant scFv. In addition, peptide pulsed and unpulsed T2 cells were also incubated with an anti-HLA-A2-FITC (BB7.2) antibody. This BB7.2 staining control was included due to previous studies which demonstrate that if a peptide is able to bind HLA-A2 on the T2 cell surface, the HLA-A2 molecule is stabilized, and the stabilization can be visualized by an increase in fluorescence intensity (81). As shown in FIG. 3A, T2 cells which have been pulsed with either the LLDFVRFMGV (SEQ ID NO: 4) or KLQCVDLHV (SEQ ID NO: 74) peptides resulted in a fluorescence shift, consistent with their binding to the HLA-A2 pocket. However, EBNA Clone 315 was only able to stain T2 cells pulsed with its specific target peptide LLDFVRFMGV (SEQ ID NO: 4) and not an irrelevant peptide (FIG. 3B). Similar results were obtained when T2 cells were pulsed with either the RMFPNAPYL (SEQ ID NO: 1) or LLDFVRFMGV (SEQ ID NO: 4) peptides and stained with WT1 Clone 45 scFv. While both peptides were able to stabilize the HLA-A2 molecule (FIG. 4A), WT1 Clone 45 scFv was only able to detect the T2 cells pulsed with the RMFPNAPYL (SEQ ID NO: 1) peptide (FIG. 4B). This further validates their utility in detecting the native complex on the surface of cells.

Next, the detection sensitivity of the EBNA Clone 315 scFv using flow cytometry was evaluated in order to correlate sensitivity with antigen density using flow cytometric quantitative beads. Briefly, TAP-deficient T2 cells were pulsed with (solid, unfilled lines) or without (dashed, unfilled lines) LLDFVRFMGV (SEQ ID NO: 4) (FIG. 3A, top, left panel) or KLQCVDLHV (SEQ ID NO: 74) peptides (FIG. 3A top, right panel) at 20 μM in serum-free IMDM media at 37° C. for 5 hours. The cells were then stained with a mouse-anti-human HLA-A2-FITC conjugated antibody (unfilled lines) or a control mouse $IgG_1$-FITC conjugated antibody (filled lines) and analyzed on the FACS machine. Peptide-pulsed T2 cells from A were stained with EBNA Clone 315 scFv (unfilled lines) or a control scFv (filled lines) (FIG. 3B). Only T2 cells which had been pulsed with the LLDFVRFMGV (SEQ ID NO: 4) peptide (left panel), but not ones which had been pulsed with KLQCVDLHV (SEQ ID NO: 74) (right panel), could be stained by the EBNA Clone 315 scFv (FIG. 3B). T2 cells were incubated with decreasing concentrations of the LLDFVRFMGV (SEQ ID NO: 4) peptide and subsequently stained with EBNA Clone 315 scFv as above (FIG. 3C). Based on geometric mean fluorescence (control scFv background subtracted), the lower limit of detection corresponds with 78 nM of peptide used for pulsing.

By titrating down the amount of peptide used for incubation with the T2 cells, it was determined that concentrations as low as 78 nM were still able to produce a fluorescence signal above background when stained with EBNA Clone 315 scFv (FIG. 3C). With decreasing concentrations of peptide used for loading, there was a corresponding reduction in overall HLA-A2 intensity (data not shown) as one would expect.

Figure 4:
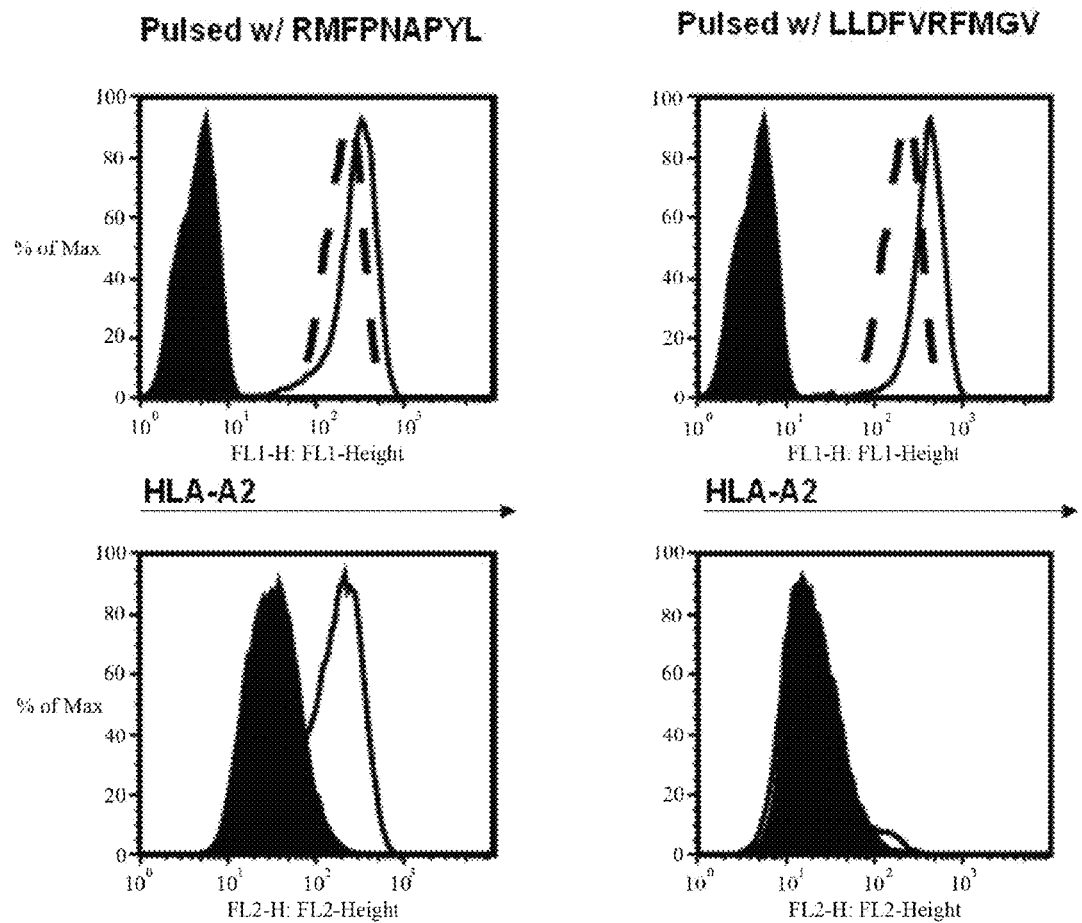
FIG. 4 shows that HLA-A2 can be detected on TAP-deficient (TAP⁻) T2 cells that were either pulsed or unpulsed with RMFPNAPYL (SEQ ID NO: 1) or LLDFVRFMGV (SEQ ID NO: 4) (FIG. 4A) but that WT-1 clone 45 scFv recognizes T2 cells that have been pulsed with RMFP-NAPYL (SEQ ID NO: 1) but not unpulsed cells or cells pulsed with LLDFVRFMGV (SEQ ID NO: 4) (FIG. 4B)

Similarly, FIG. 4 shows that WT1 Clone 45 can recognize HLA-A2-RMFPNAPYL (SEQ ID NO: 1) on peptide-pulsed T2 cells. TAP-deficient T2 cells were pulsed with (solid, unfilled lines) or without (dashed, unfilled lines) RMFP-NAPYL (SEQ ID NO: 1) (left panel) or LLDFVRFMGV (SEQ ID NO: 4) peptides (right panel) at 40 µM in serum-free IMDM media at 37° C. for 5 hours. The cells were then stained with a mouse-anti-human HLA-A2-FITC conjugated antibody (unfilled lines) or a control mouse IgG1-FITC conjugated antibody (filled lines) and analyzed on the FACS machine (FIG. 4A). Peptide-pulsed T2 cells from A were stained with WT1 Clone 45 (unfilled lines) or a control scFv (filled lines). Only T2 cells which had been pulsed with the RMFPNAPYL (SEQ ID NO: 1) peptide (left panel), but not ones which had been pulsed with LLDFVRFMGV (SEQ ID NO: 4) (right panel), could be stained by the WT1 Clone 45 (FIG. 4B).

Example 20

Figure 5:
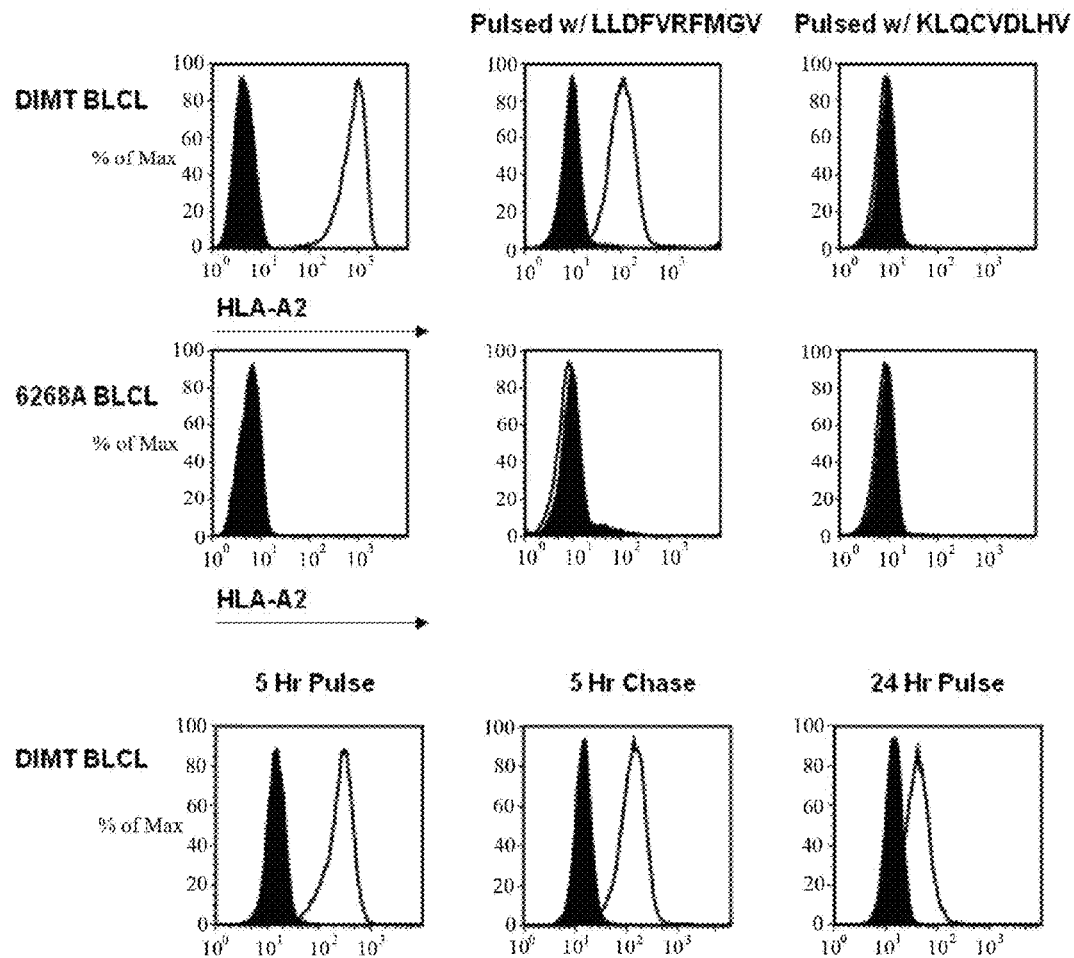
FIG. 5 shows that when DIMT (FIG. 5A) and 6268A (FIG. 5B) BLCLs are incubated with LLDFVRFMGV (SEQ ID NO: 4) (middle panel) or KLQCVDLHV (SEQ ID NO: 74) peptides (right panel) and stained with EBNA clone 315 scFv, only HLA-A2+DIMT peptide-pulsed with LLDFVRF-MGV (SEQ ID NO: 4) could be stained, showing that EBNA clone 315 and LLDFVRFMGV (SEQ ID NO: 4) are HLA-A2 restricted; a time course (FIG. 5C) shows that the HLA-A2-LLDFVRFMGV (SEQ ID NO: 4) complex is stable on the cell surface.

Demonstrating HLA Restriction of the LLDFVRFMGV (SEQ ID NO: 4) Peptide and EBNA Clone 315 Using Peptide-Pulsed BLCLs The expression of these peptides on BLCLs, especially since BLCLs are used routinely as APCs (82), was examined. Two BLCL lines were used, one HLA-A2$^+$ (DIMT) and one HLA-A2$^-$ (6268A) (FIG. 5A). The BLCLs were incubated in serum-free IMDM media for 5 hours at 37° C. with either the specific LLDFVRFMGV (SEQ ID NO: 4) or irrelevant KLQCVDLHV (SEQ ID NO: 74) peptides. When incubated with the specific peptide, only the HLA-A2$^+$ DIMT BLCL could be stained by EBNA Clone 315 (FIG. 5B). Similarly to results seen with T2 cells, DIMT cells loaded with the irrelevant peptide, or 6268A loaded with the specific/irrelevant peptide, could not be stained with EBNA Clone 315. It is interesting to note that without peptide pulsing we were unsuccessful at staining DIMT. While our staining approach has been optimized to detect low levels of antigen through signal amplification involving secondary and tertiary reagents to detect the scFv, the amount of peptide that the cell naturally presents seems to be below our level of detection.

Subsequently, in an attempt to study the duration of peptide presentation on HLA-A2, a pulse-chase experiment was set up to monitor the levels of the HLA-A2-EBNA3C complex on DIMT cells over time. Initially, DIMT cells were incubated in serum-free IMDM media for 5 hours at 37° C. with the LLDFVRFMGV (SEQ ID NO: 4) peptide. Afterwards, the cells were washed twice with RPMI+10% FBS and further cultured in this media for an additional 5 hours and 24 hours. At each of these three time points, cells were harvested and stained with either the purified EBNA Clone 315 scFv or an irrelevant scFv. The results show that after pulsing the HLA-A2-EBNA3C complex could easily be detected on the cell surface (FIG. 5C). Interestingly, even after the cells were transferred to fresh media and cultured for an additional 5 and 24 hours, the MHC-peptide complex could still be detected, signifying that peptide-pulsed BLCLs are able to hold onto and present antigen for at least a day after the peptide had been removed from the media. This data further supports the use of autologous BLCLs in the generation of antigen specific T cells and the utility of TCE-specific antibodies like EBNA Clone 315 in precise visualization of TCE expression on APCs or target cells.

Example 21

Construction of EBNA Clone 315 and WT1 Clone 45 scFv-Fc Fusion Proteins

Figure 6:
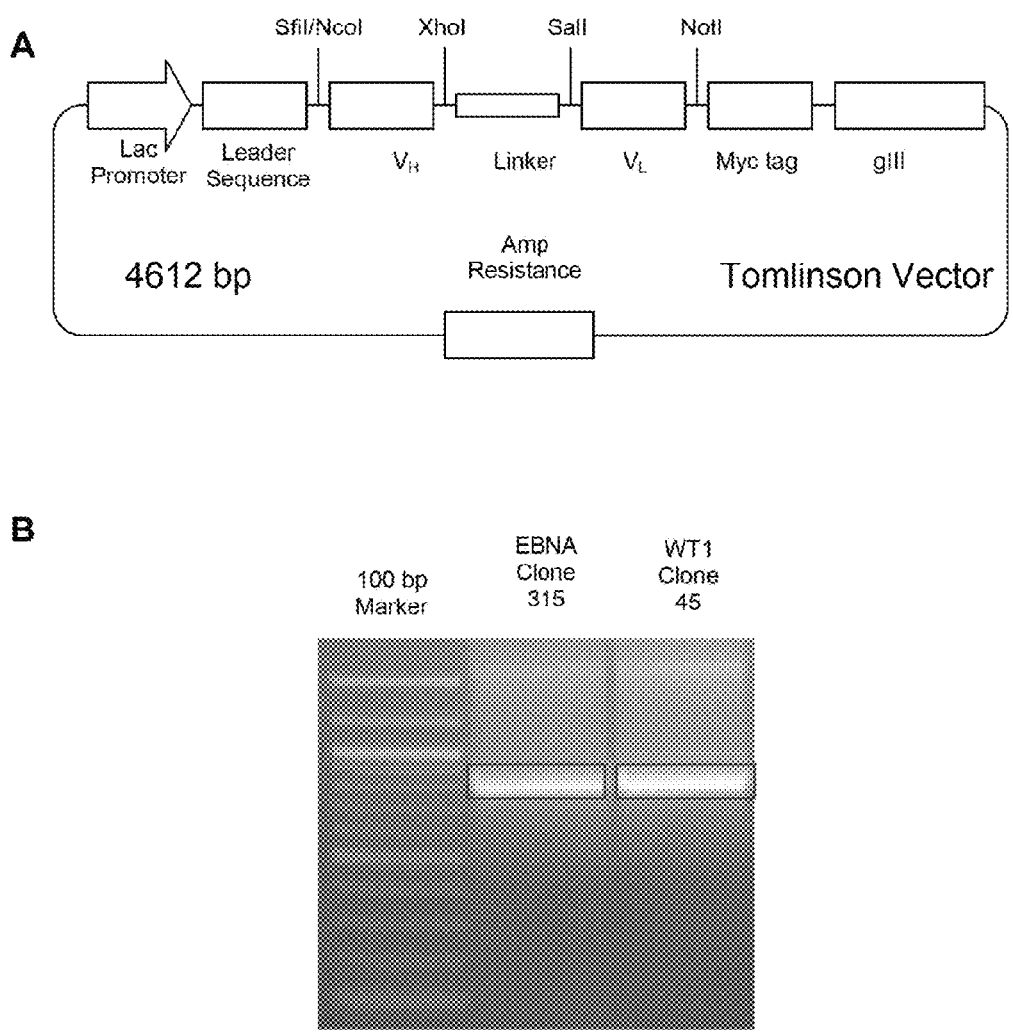
FIG. 6 shows the Tomlinson library vector used in PCR to add appropriate restriction enzyme sites to either side of the WT1 Clone 45 and EBNA Clone 315 scFv sequences (FIG. 6A).
Figure 7:
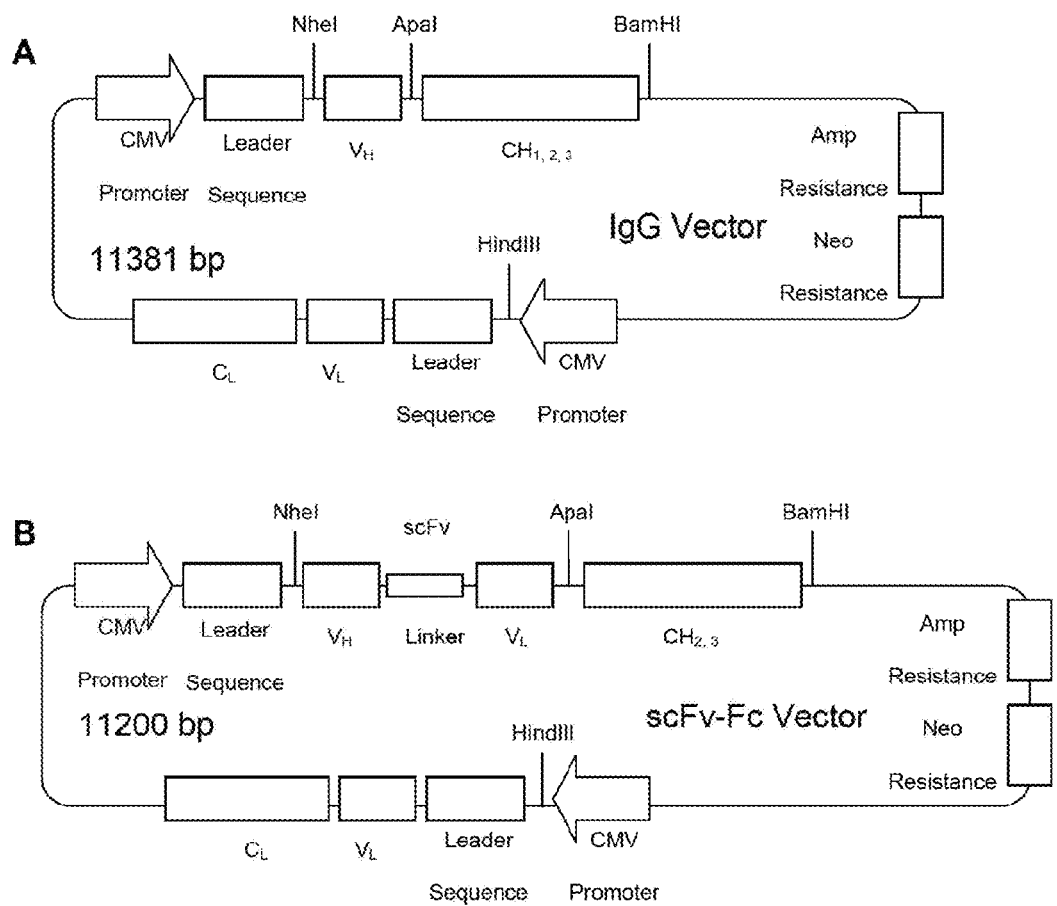
FIG. 7 shows the full IgG expression vector (FIG. 7A) that was used to generate an expression vector for scFv-Fc fusion proteins (FIG. 7B). A. The structure of the proprietary IgG expression vector (11381 bp). The vector expresses the heavy and light chains under two separate CMV promoters. The variable heavy chain (V$_H$) is fused to the first, second and third constant heavy chains (CH$_{1, 2, 3}$) and expressed under one promoter while the variable light chain (V$_L$) is fused to the constant light chain (C$_L$) and expressed under a different promoter. This vector was further modified to lack the first constant region of the heavy chain (CH$_1$), and this vector was used for the construction of scFv-Fc fusion proteins. B. After excision of the V$_H$ from the IgG vector using NheI and ApaI, the pre-digested, purified scFv PCR products were ligated to the IgG vector to allow for the expression of the scFv fused to the CH$_{2, 3}$ domains (Fc).

Initially, the scFv sequences were made compatible for cloning into a scFv-Fc expression vector by using PCR to add the desired restriction enzyme sites (NheI and ApaI) to either side of the EBNA Clone 315 and WT1 Clone 45 scFv sequences. The PCR reaction was done on the Tomlinson library vector which contained the WT1 Clone 45 and EBNA Clone 315 scFv sequences (FIG. 7A). After subsequent digestion using NheI and ApaI, the digested PCR products were removed from a 1% agarose gel and purified (FIG. 6B).

With regards to cloning and expression of the scFv-Fc fusion proteins, a proprietary vector obtained from Eureka therapeutics (IgG Vector) was used. The first constant heavy chain ($CH_1$) was removed from this vector, something which is typically done when generating Fc fusion proteins (83). Once generated, the vector was digested with NheI and ApaI and then ligated to the predigested PCR products from FIG. 7B. The ligated products yielded a vector which expressed the EBNA Clone 315 or WT1 Clone 45 scFv genes in tandem to the $CH_{2, 3}$ domains of a human IgG1 under a single CMV promoter (scFv-Fc Vector; FIG. 7B). After further validation using DNA sequencing, the two fusion constructs were linearized using HindIII and ran on a 1% agarose gel. Digestion with HindIII also allowed us to block the expression of the light chain that is still present in the vector, which for all intensive purposes was undesired. As expected, both digested plasmids ran at the anticipated size (~11,000 bp) based on their location relative to the lambda HindIII marker. Each linearized plasmid was subsequently introduced into DG44 cells and cultured in OPTICHO media as described in Example 10 above.

Example 22

Figure 8:
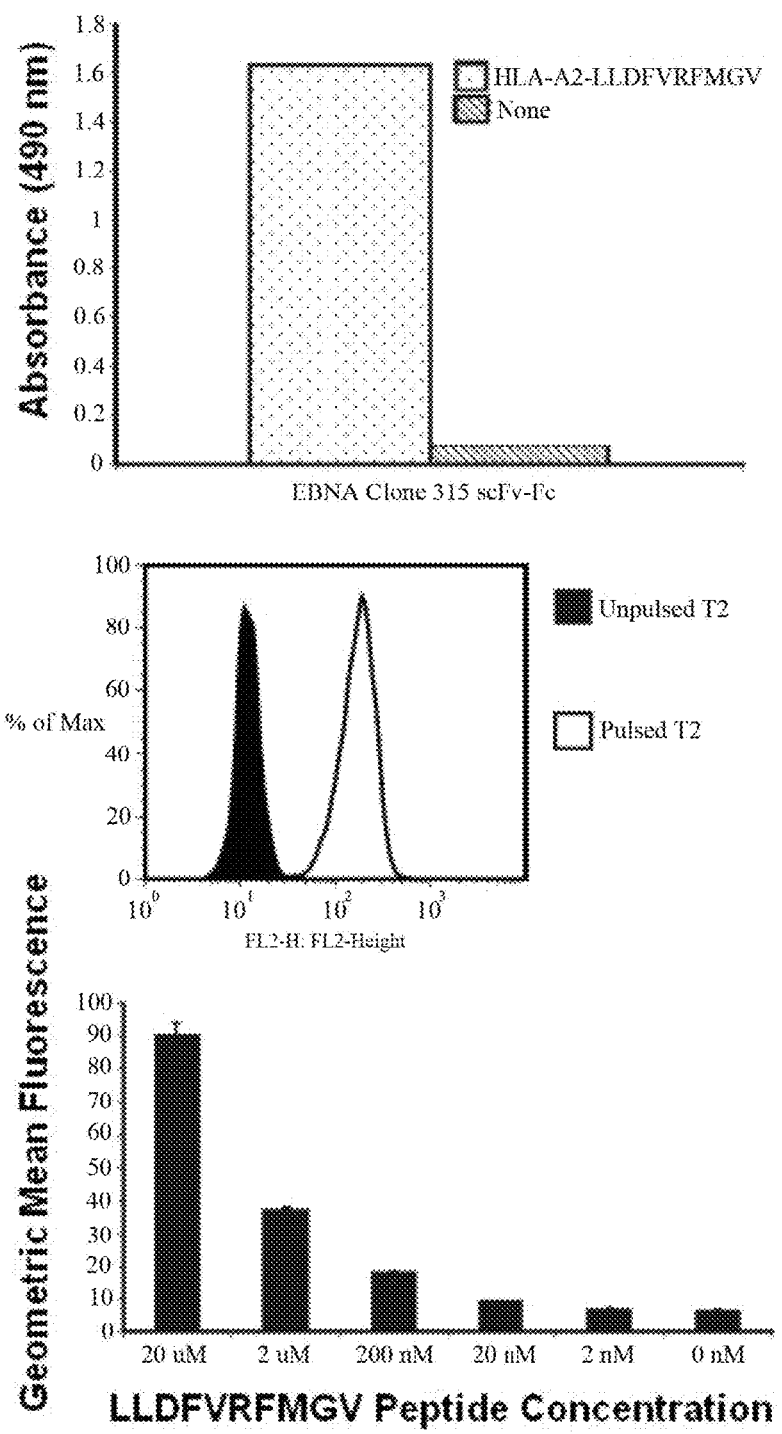
FIG. 8 shows the results of binding studies using EBNA Clone 315 scFv-Fc in which purified EBNA Clone 315 scFv-Fc was shown to maintain its binding ability towards the recombinant complex when tested for binding on an ELISA plate coated with or without HLA-A2-LLDFVRF-MGV (SEQ ID NO: 4) (FIG. 8A) and when tested for binding on T2 cells pulsed with or without the LLDFVRF-MGV (SEQ ID NO: 4) peptide (FIG. 8B). When T2 cells were incubated with decreasing concentrations of the LLD-FVRFMGV (SEQ ID NO: 4) peptide and subsequently stained with EBNA Clone 315 scFv-Fc, a lower limit of detection was demonstrated to be in the same range as the scFv (200 nM-20 nM) (FIG. 8C).

Binding Kinetics and Sensitivity of EBNA Clone 315 scFv-Fc on Recombinant HLA-A2-Peptide Complex and Peptide-Pulsed T2 Cells To further understand the affinity of the interaction between EBNA Clone 315 and the HLA-A2-EBNA3C complex, surface plasmon resonance was used to determine the binding kinetics between these two proteins. First, the EBNA Clone 315 scFv-Fc was purified and its binding ability was tested using ELISA (FIG. 8A) along with flow cytometry via peptide-pulsed T2 cells at varying concentrations (FIGS. 8B and C). These initial studies demonstrate that the antibody maintains its binding characteristics when expressed as a fusion protein In addition, it is important to note that the flow cytometric sensitivity of the scFv and scFv-Fc were very comparable (200 nM-20 nM), further highlighting the utility of the scFv as a monomeric binding fragment.

Next, using the BIACORE T100 (GE Healthcare), a CM5 chip (flow cells 1 and 2) was initially activated for amine coupling based on manufacturer recommendation. The purified EBNA Clone 315 scFv-Fc was subsequently immobilized onto the second flow cell and the purified HLA-A2-

Figure 9:
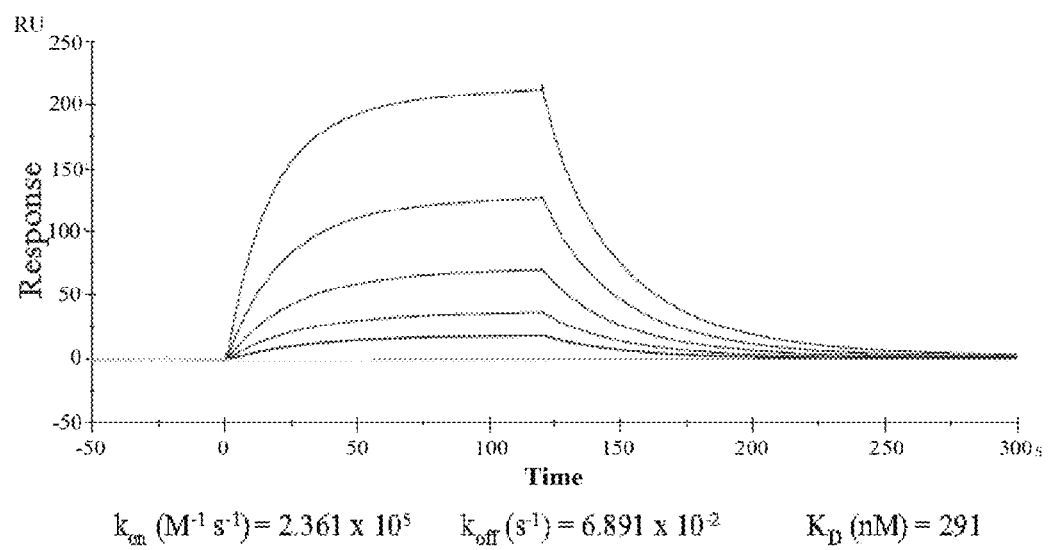
FIG. 9 shows the results of kinetics determination of EBNA Clone 315 to HLA-A2-LLDFVRFMGV (SEQ ID NO: 4) using surface plasmon resonance.

EBNA3C complex passed over both flow cells as part of the soluble phase. After background subtraction (signal from flow cell 2 minus that of flow cell 1), the association rate ($k_{on}$) and dissociation rate ($k_{off}$) were determined ($2.361 \times 10^5$ $M^{-1}s^{-1}$ and $6.891 \times 10^{-2} s^{-1}$, respectively), resulting in an overall $K_D$ ($k_{off}/k_{on}$) of 291 nM using a 1:1 binding model (FIG. 9); these kinetic rates were very similar to previously isolated Fabs against different MHC-peptide complexes (22, 31). Relative to published TCR:MHC Class I-peptide $K_D$ measurements, which typically range in the neighborhood of 2-50 µM (84), our scFv:MHC Class I-peptide interaction seems to be at best 150-fold stronger, with the most significant improvement attributed to a slower $k_{off}$. Previous studies which support an affinity-based T cell activation model argue that a greater overall affinity or slower dissociation rate leads to higher interferon-gamma release and target cell lysis (85, 86).

Figure 10:
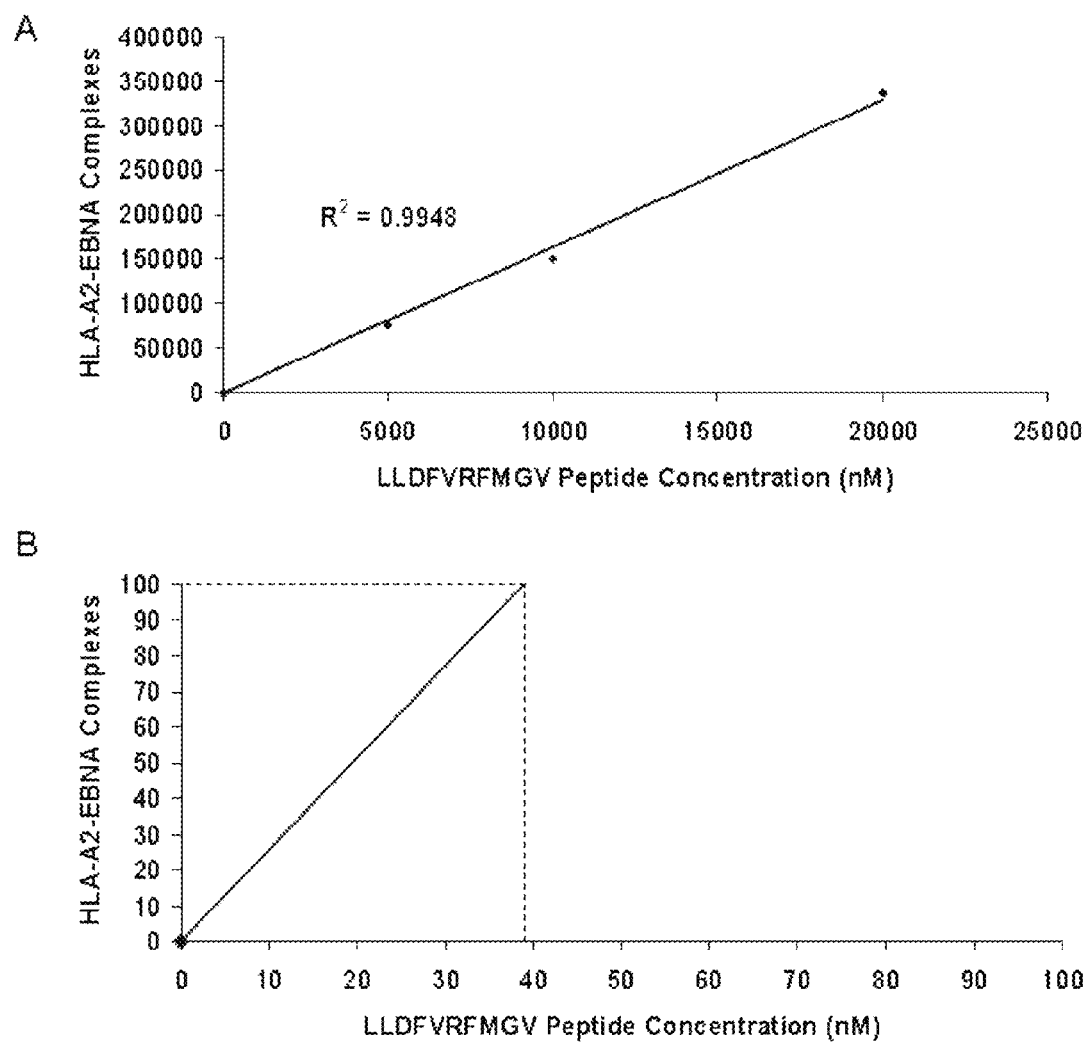
FIG. 10 shows the results of HLA-A2-LLDFVRFMGV (SEQ ID NO: 4) complex quantitation on T2 cells using fluorescently-conjugated EBNA Clone 315 scFv-Fc (FIG. 10A). Fluorescently-conjugated EBNA Clone 315 scFv-Fc was tested for binding on T2 cells pulsed with (20, 10, or 5

Lastly, in an attempt to quantify the amount of HLA-A2-LLDFVRFMGV (SEQ ID NO: 4) complex on the surface of peptide-pulsed T2 cells, we decided to use flow cytometric quantitation beads. This data will also be useful in determining the detection threshold of EBNA Clone 315 scFv and scFv-Fc. First, purified EBNA Clone 315 scFv-Fc was conjugated to a fluorescent label, ALEXA FLUOR 647 using a commercially available kit. Subsequently, T2 cells were pulsed with 20, 10, 5, or 0 µM of LLDFVRFMGV (SEQ ID NO: 4) peptide at 37° C. for 5 hours. After pulsing, the peptide-pulsed T2 cells, along with beads containing known quantities of anti-human $IgG_1$ antibodies, were incubated with the fluorescently-labeled EBNA Clone 315 scFv-Fc. Once the cells and beads were analyzed on the FACS machine, the fluorescence intensities were correlated to each other, resulting in an estimation of the number of complexes on the surface of the T2 cells relative to the quantity of peptide used for pulsing. These four values (337,091 sites with 20 µM, 149,688 sites with 10 µM, 76,040 sites with 5 µM, and no sites with 0 µM) were plotted on a graph and a trendline was used to create a standard curve ($R^2=0.9948$) (FIG. 10A). Furthermore, when looking at the lower end of the spectrum, we have determined that an amount less than 40 nM of peptide will correspond to less than 100 complexes on the surface of the cell (FIG. 10B), placing the detection level of the EBNA Clone 315 scFv-Fc fusion within that range.

Example 23

Figure 11:
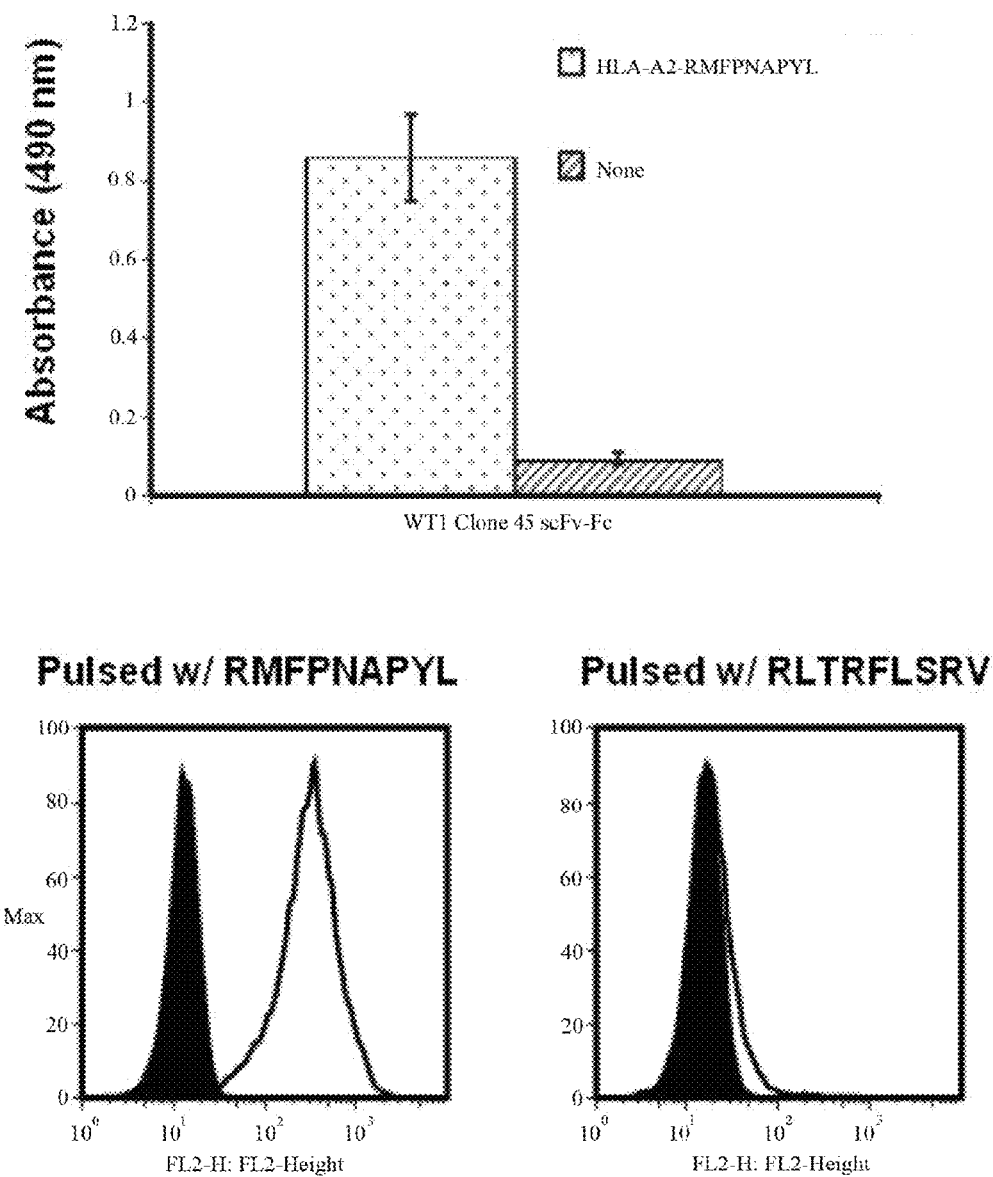
FIG. 11 shows the results of binding and specificity studies when purified WT1 Clone 45 scFv-Fc was tested for binding on an ELISA plate coated with or without HLA-A2-RMFPNAPYL (SEQ ID NO: 1) (FIG. 11A).

Binding and Specificity Studies of WT1 Clone 45 scFv-Fc on Recombinant HLA-A2-Peptide Complex and Peptide-Pulsed Cells In order to do further studies regarding the presentation of the RMFPNAPYL (SEQ ID NO: 1) peptide on the surface of APCs, the WT1 Clone 45 scFv-Fc fusion protein was first purified and validated for binding to its targeted recombinant HLA-A2-peptide complex (FIG. 11A). As was shown with the scFv, the fusion protein maintained its binding ability on the ELISA plate. Next, we decided to check and see if the scFv-Fc maintained its binding ability and specificity on peptide-pulsed T2 cells. T2 cells were pulsed with the RMFPNAPYL (SEQ ID NO: 1) peptide or an irrelevant peptide in serum-free media with $\beta_2M$ at 37° C. for 5 hours. Using flow cytometry, the scFv-Fc was able to detect T2 cells which had been pulsed with the RMFPNAPYL (SEQ ID NO: 1) peptide, but failed to recognize the cells pulsed with an irrelevant peptide (FIG. 11B). These two assays further validated that the fusion protein acts in the same way as the original scFv.

Figure 12:
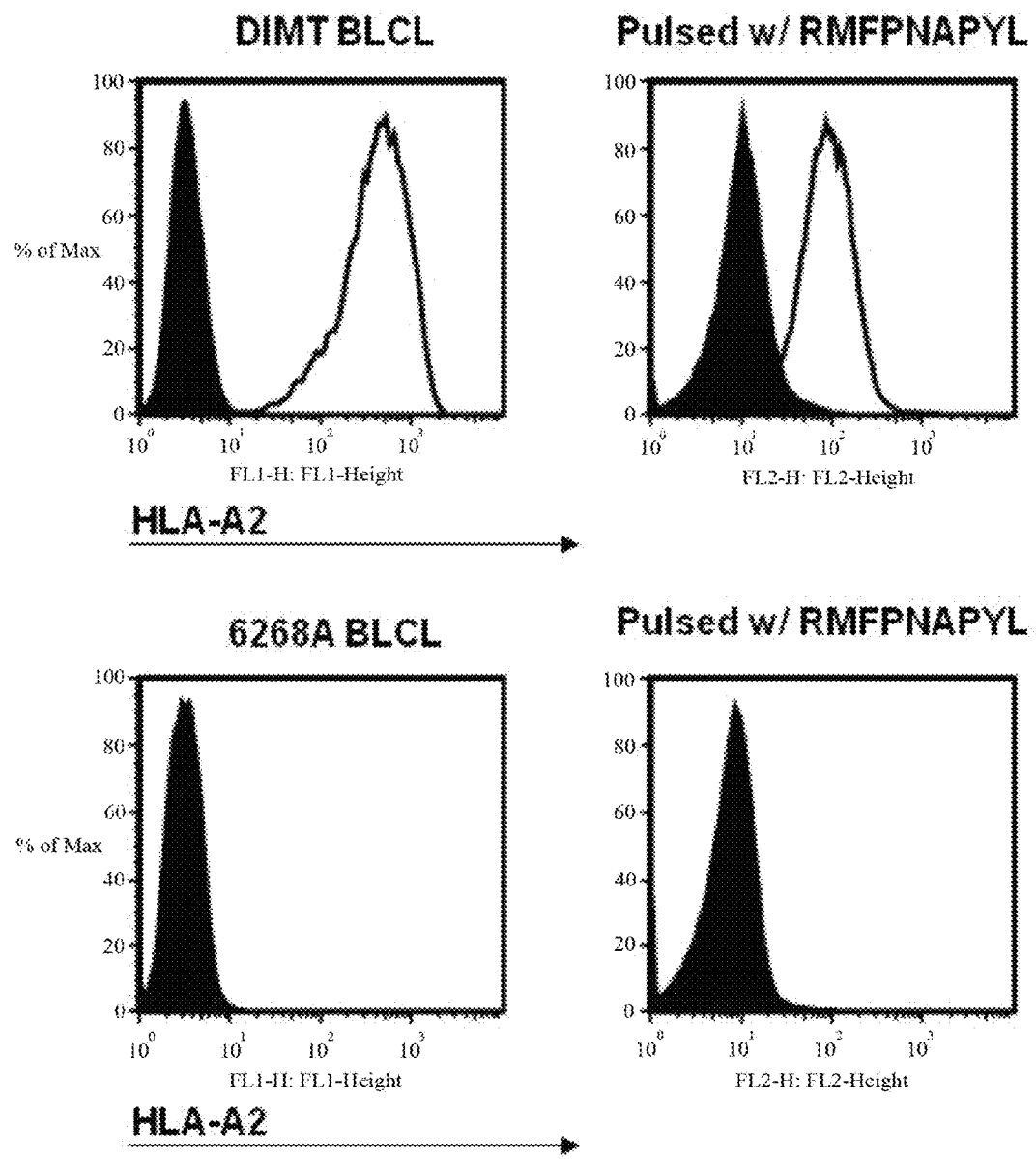
FIG. 12 shows that when DIMT (top) and 6268A (bottom) BLCLs were incubated with RMFPNAPYL (SEQ ID NO: 1) (right panel) and the peptide-pulsed BLCLs were stained with WT1 Clone 315 scFv-Fc (unfilled lines) or a control scFv (filled lines), only the HLA-A2-positive RMFPNAPYL (SEQ ID NO: 1) peptide-pulsed DIMT BLCLs could be stained.

Subsequently, we decided to test whether the binding of the RMFPNAPYL (SEQ ID NO: 1) peptide and scFv-Fc fusion protein were restricted to HLA-A2. HLA-A2$^+$ and HLA-A2$^-$ BLCLs (DIMT and 6268A, respectively) were pulsed with the RMFPNAPYL (SEQ ID NO: 1) peptide in serum-free media at 37° C. for 5 hours. Similarly to EBNA Clone 315, the WT1 Clone 45 scFv-Fc fusion protein was only able to recognize the peptide pulsed DIMT and not the HLA-A2$^-$ 6268A BLCL (FIG. 12). These results demonstrate that the RMFPNAPYL (SEQ ID NO: 1) peptide is restricted to HLA-A2 and WT1 Clone 45 is only able to recognize it in the context of this complex.

Example 24

Antibody-Dependent Cellular Cytotoxicity (ADCC) of EBNA Clone 315 scFv-Fc on Peptide-Pulsed Cells In addition to using the scFv-Fc for antigen presentation studies, we tested whether the truncated human $IgG_1$ Fc region is capable of inducing antibody-dependent cellular cytotoxicity (ADCC). In order to avoid variability amongst human donor lymphocytes, and in an effort to increase the chances of observing cytotoxicity, Hong-fen Guo in our laboratory generated a CD16(V)-transduced NK92MI cell line. This NK92 cell variant is transduced with both IL-2 and the human CD16 activating Fc receptor (FcγRIIIA) containing a high affinity polymorphism (valine instead of phenylalanine at position 158 on CD16) responsible for an enhancement in ADCC and clinical response to antibody-based immunotherapy (87, 88).

Figure 13:
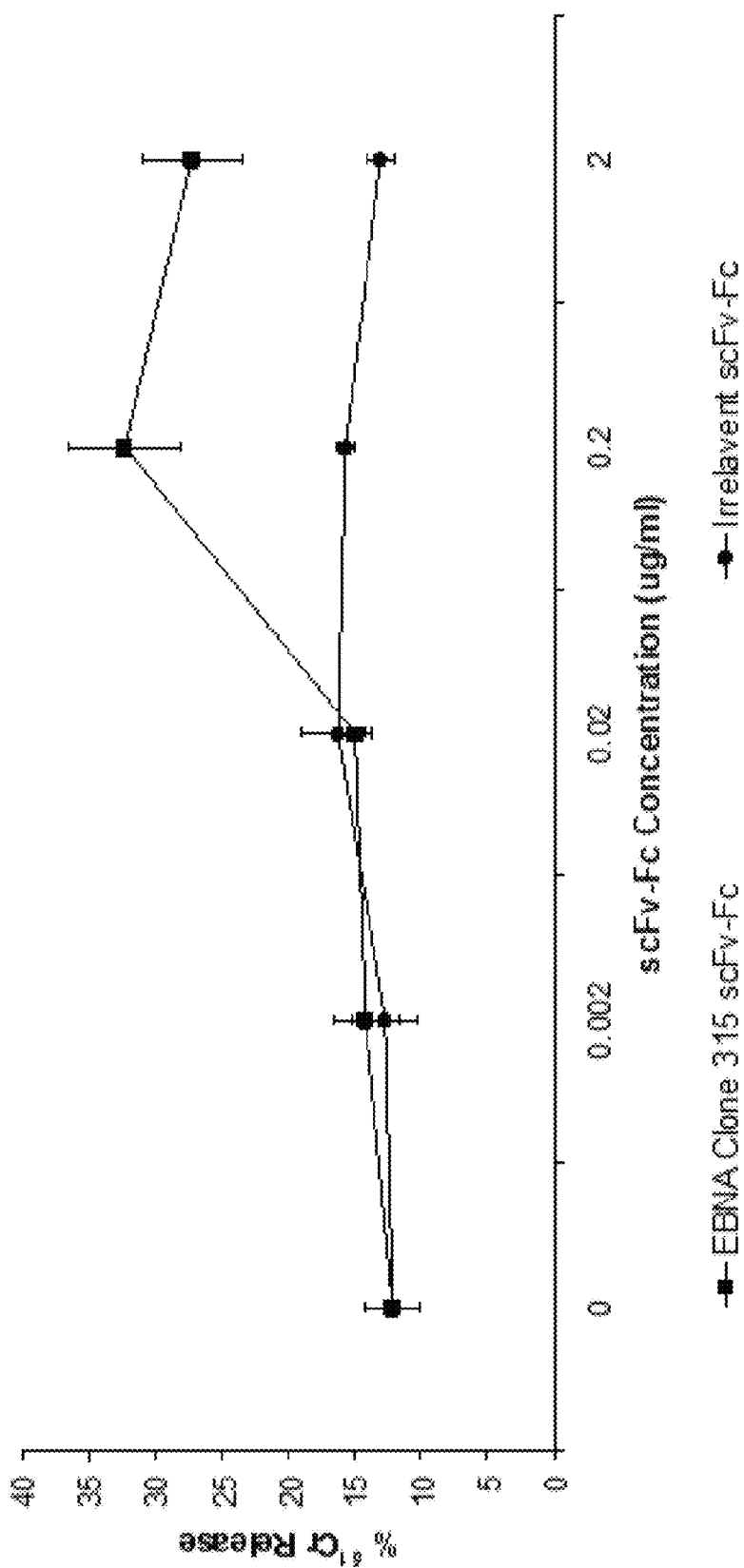
FIG. 13 shows EBNA Clone 315 scFv-Fc mediated ADCC (measured using $^{51}$Cr release) of LLDFVRFMGV (SEQ ID NO: 4) peptide-pulsed cells.

We used this cell line in combination with the EBNA Clone 315 scFv-Fc or an irrelevant, isotype-matched scFv-Fc to test whether the fusion protein can induce NK92MI-mediated ADCC against LLDFVRFMGV (SEQ ID NO: 4)-pulsed LUY (HLA-A2$^+$) BLCL. At an E:T ratio of 42:1, EBNA Clone 315 scFv-Fc led to greater killing over background (with or without an irrelevant scFv-Fc) at the two highest concentrations tested (27-32% versus 13-15%) (FIG. 13). A similar magnitude of killing (over background) was also observed with other peptide-pulsed, HLA-A2$^+$ target BLCLs (DIMT and JG19). These results show that these truncated scFv-Fc fusion proteins maintain their Fc-mediated effector functions, despite being about 33% smaller than a full immunoglobulin.

Example 25

Construction and Retroviral Transduction of an HLA-A2-RMFPNAPYL (SEQ ID NO: 1)-Specific Chimeric Antigen Receptor into NK92MI Cells In order to generate a CAR specific for the HLA-A2-RMFPNAPYL (SEQ ID NO: 1) complex, the WT1 Clone 45 scFv would typically be fused to intracellular signaling domains of immune-modulatory proteins found in immune effector cells. A CAR expression vector (St. Jude CAR) in which a CD19-specific scFv is fused to the CD8a hinge/transmembrane region, 4-1 BB and CD3 chain was obtained and modified so that the anti-CD19 scFv was replaced with a WT1 Clone 45 scFv. However, due to restriction enzyme incompatibility issues between the St. Jude CAR vector and the Tomlinson library vector used for PCR, the entire CAR gene, containing the WT1 Clone 45 scFv, was commercially synthesized by Genescript. The resulting WT1 pUC57 vector contained the desired WT1 Clone 45 CAR sequence flanked by EcoRI and XhoI.

An additional feature to the St. Jude CAR vector is an IRES-GFP sequence downstream of the CAR sequence. This allows for direct correlation of CAR expression with GFP without having to fuse both proteins together. In order to take advantage of this feature, we digested the WT1 pUC57 vector and St. Jude CAR vector using EcoRI and XhoI. Afterwards, the digested and undigested plasmids were run on a 1% agarose gel along with the lambda HindIII and 100 bp markers. The highlighted bands corresponded to the anticipated sizes of the St. Jude plasmid lacking the CAR sequence (~6500 bp) and the WT1 Clone 45 CAR sequence lacking the pUC57 plasmid (~1500 bp). These bands were excised from the gel, and after DNA purification, the two were ligated together. After the ligation products were transformed into E. coli, 8 colonies were selected at random and their plasmids isolated. The isolated plasmids were then validated by sequencing to determine whether they contain the WT1 Clone 45 scFv sequence in the context of the CAR. In addition, the plasmids were also digested with EcoRI and XhoI and run on a 1% agarose gel along with lambda HindIII and 100 bp markers to validate their sizes. After demonstrating that both bands from each plasmid yielded the expected sizes, it was determined that the cloning was successful.

Figure 23:
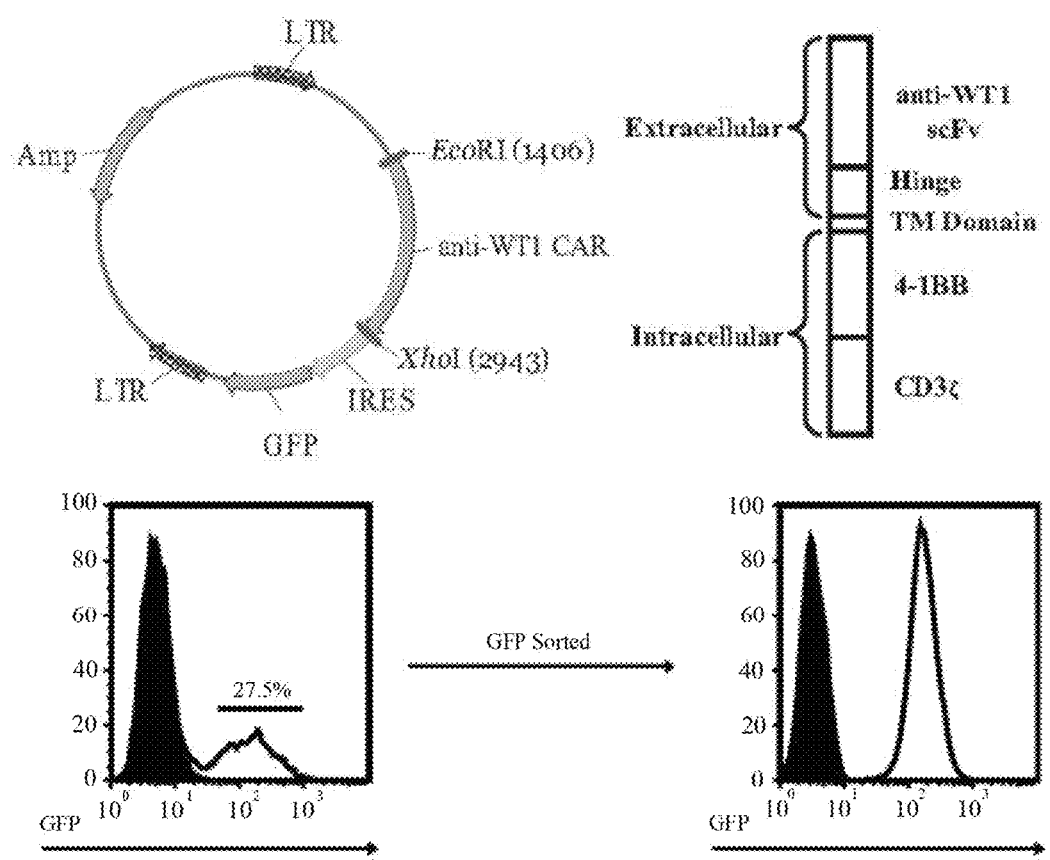
FIG. 23 shows the MSCV-based vector (top left panel) containing an IRES-GFP sequence along with ampicilin-resistance used for transduction and expression of anti-WT1 CAR in NK92MI cells. A. The WT1 Clone 45 scFv sequence was cloned into the CAR gene (anti-WT1 CAR) and further cloned into the MSCV-based vector. The resulting CAR (top right panel) is composed of the scFv and hinge region on the extracellular surface, a transmembrane domain, along with 4-1 BB and the CD3 chain present within the cell. B After retroviral packaging using 293T GP2 cells and transduction into NK92MI cells, approximately 27.5% of the NK92MI cells contained the construct based on GFP expression (bottom left panel; unfilled lines) when compared to mock transduced (empty retrovirus) NK92MI cells (bottom left panel; filled lines). Of the GFP-positive cells, the top 20% were flow cytometrically sorted and expanded to yield a population of stably transduced cells which were greater than 98% GFP positive (bottom right panel).

Once the WT1 Clone 45 CAR was generated (FIG. 23), the DNA was packaged into retrovirus using the 293T-based GP2 cell line. Once the retrovirus was generated in the culture media, it was recovered and concentrated. The concentrated virus was then used to infect 500,000 to 1,000,000 NK92MI cells in NK92MI growth media. After 3-4 days of culture, the NK92MI cells infected with the retrovirus were compared to mock-infected cells (infected with empty retrovirus) with regards to GFP expression using flow cytometry. While the infection efficiency was approximately 27.5%, flow assisted cytometric cell sorting (FACS) allowed us to enrich the GFP-positive population to more than 98% positive (FIG. 23).

Example 26

Construction and Retroviral Transduction of an HLA-A2-LLDFVRFMGV (SEQ ID NO: 4) -Specific Chimeric Antigen Receptor into NK92MI Cells Since the WT1 Clone 45 CAR required us to purchase the WT1 pUC57 vector, additional restriction sites were added to this construct for greater ease when swapping different scFvs. As a result, the EBNA Clone 315 scFv sequence could directly be cloned out of the Tomlinson vector from which it was derived.

The first cloning step involved the removal of the WT1 Clone 45 scFv from the WT1 pUC57 vector using SfiI and NotI. The same digestion was done to the Tomlinson vector containing the EBNA Clone 315 scFv sequence. Once digested, both plasmids were run on a 1% agarose gel along with lambda HindIII and 100 bp markers. The highlighted bands corresponded to the WT1 pUC57 vector without a scFv, and the EBNA Clone 315 scFv excised from the Tomlinson vector. These bands were excised from the gel, the DNA was purified, and ligated together to yield the EBNA pUC57 vector. The ligation products were subsequently transformed into E. coli, 10 colonies were selected at random, their plasmids were purified, and each DNA digested with EcoRI alone or EcoRI and XhoI. As anticipated, due to an inherent XhoI site within every scFv sequence derived from the Tomlison vector (with the exception of WT1 Clone 45 scFv in the context of pUC57 since the site was removed when purchased as a CAR from Genescript), the double digestion yielded three separate bands.

For the second cloning step, in which the EBNA Clone 315 CAR sequence was excised from the pUC57 vector and added to the St. Jude CAR vector, a partial digestion of the EBNA pUC57 vector using XhoI was necessary. The EBNA pUC57 plasmids isolated from the 10 colonies above were combined and digested with XhoI at room temperature for 1 minute. The reaction was quickly stopped by adding it to 4 separate wells of a 1% agarose gel and running the DNA along with uncut plasmid, lambda HindIII and 100 bp markers. The highlighted bands were determined to be the expected size of the linearized EBNA pUC57 plasmid (~4300 bp); this linearized plasmid is a result of a random cut at either of the two XhoI sites. Subsequently, to obtain the complete CAR sequence (~1500 bp), the linearized plasmid was isolated from the gel and digested completely with EcoRI. The resulting double and single digests were run on a 1% agarose gel along with the lambda HindIII and 100 bp markers. The highlighted band corresponded to the anticipated size of the EBNA Clone 315 CAR gene, and as a result was excised from the gel, DNA purified, and ligated to the predigested (EcoRI and XhoI) St. Jude CAR vector. After the ligation products were transformed into E. coli, 10 colonies were selected at random and their plasmids isolated. The isolated plasmids were then validated by sequencing to determine whether they contain the EBNA Clone 315 scFv sequence in the context of the CAR. In addition, the plasmids were also digested with EcoRI and run on a 1% agarose gel along with the lambda HindIII marker to validate their sizes. After demonstrating that the bands yielded the expected sizes, it was determined that the cloning was successful.

Figure 14:
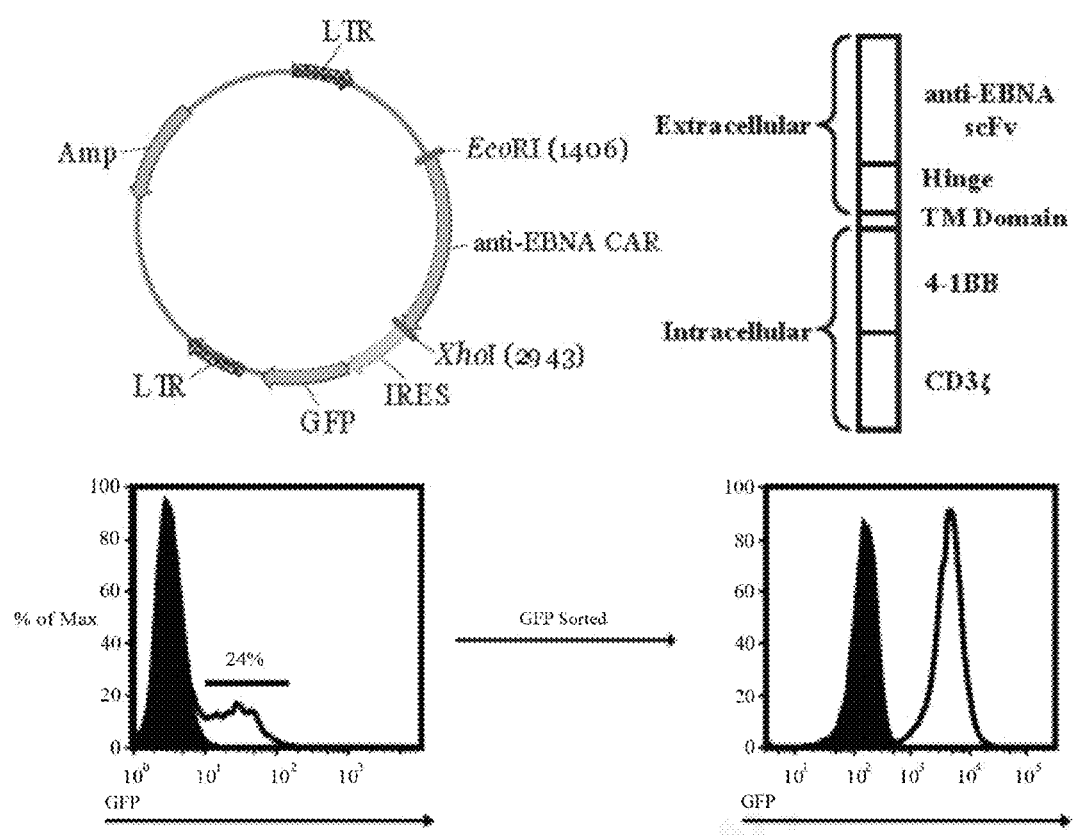
FIG. 14 shows the MSCV-based vector (top left panel) containing an IRES-GFP sequence along with ampicilin-resistance used for transduction and expression of anti-EBNA CAR in NK92MI cells. The EBNA Clone 315 scFv sequence was cloned into the CAR gene (EBNA CAR) and further cloned into an MSCV-based vector (top left panel) which contained an IRES-GFP sequence along with ampicilin-resistance. The resulting CAR (top right panel) is composed of the scFv and hinge region on the extracellular surface, a transmembrane domain, along with 4-1 BB and the CD3ζ chain present within the cell. After retroviral packaging using 293T GP2 cells and transduction into NK92MI cells, approximately 24% of the NK92MI cells contained the construct based on GFP expression (bottom left panel; unfilled lines) when compared to mock transduced (empty retrovirus) NK92MI cells (bottom left panel; filled lines). Of the GFP-positive cells, the top 20% were flow cytometrically sorted and expanded to yield a population of stably transduced cells which were greater than 90% GFP positive (bottom right panel). Retroviral transduction was done on three separate occasions, with 24% being the highest efficiency.
Figure 15:
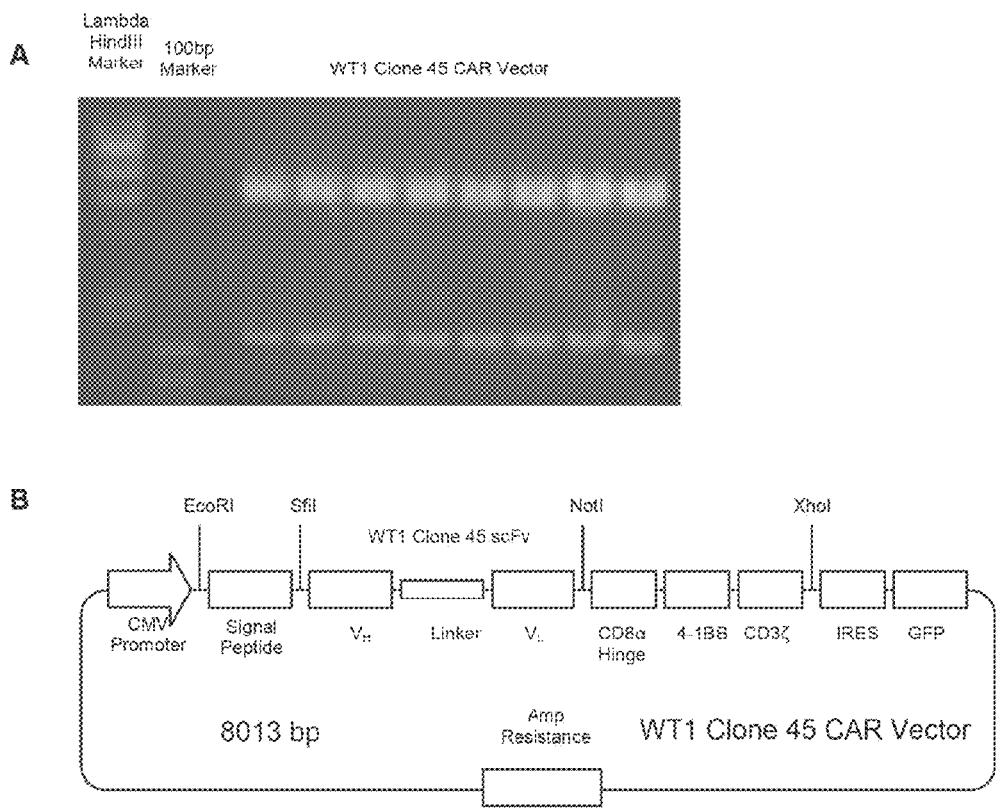
FIG. 15 shows EcoRI and XhoI digestion validation of the WT1 Clone 45 CAR vector.

After the EBNA Clone 315 CAR was generated (FIG. 14), the DNA was packaged into retrovirus and used to infect NK92MI cells in the same way as with the WT1 Clone 45 CAR. After 3-4 days of culture, the GFP expression level of the infected NK92MI cells were compared to mock-infected cells. The initial infection efficiency was approximately 24%, and after flow assisted cytometric cell sorting (FACS), the GFP-positive population was enriched to more than 90% positive (FIG. 14).

Example 27

Figure 16:
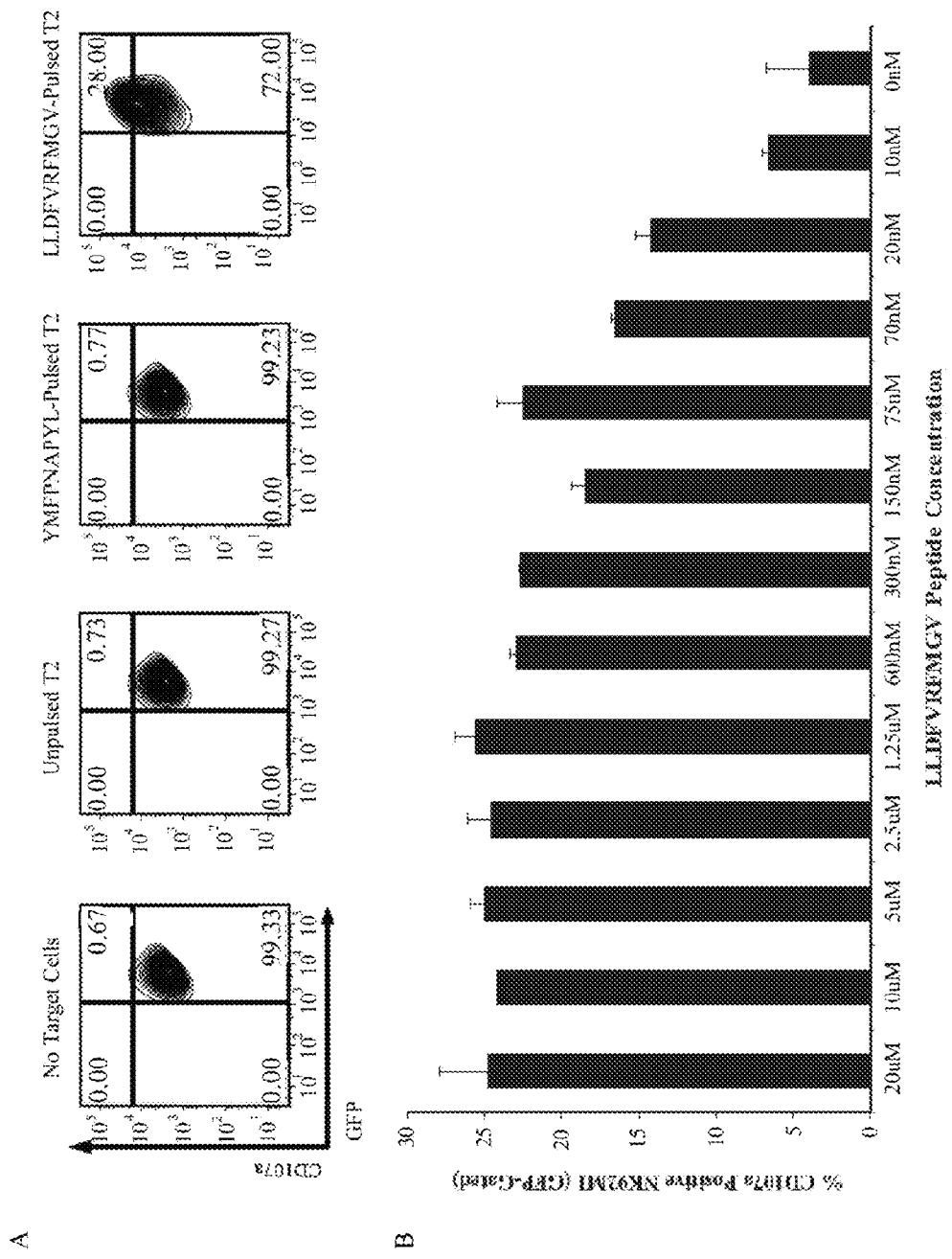
FIG. 16 shows that Clone 315 CAR-expressing NK92MI cells can specifically detect the HLA-A2-EBNA3C complex on peptide-pulsed T2 cells via CD107a expression. T2 cells were pulsed with or without LLDFVRFMGV (SEQ ID NO: 4) or YMFPNAPYL (SEQ ID NO: 76) peptides at 20 μM. CAR-equipped NK92MI cells were then cultured in media containing an anti-CD107a-PE conjugated antibody at 37° C. for 5 hours with or without peptide pulsed or unpulsed cells.

EBNA Clone 315 CAR-Equipped NK92MI Cells can Detect Cells Bearing the Specific HLA-A2-LLDFVRFMGV (SEQ ID NO: 4) Complex Via CD107a Expression Once the NK92MI cells were enriched for EBNA Clone 315 CAR expression, they were tested for their ability to recognize the targeted HLA-A2-EBNA3C complex. As an initial readout of NK92MI activation by target cells, we assayed for cell surface expression of CD107a, a marker of NK cell and T cell degranulation (90, 91). T2 cells were loaded with 20 μM of the targeted peptide (LLDFVRFMGV (SEQ ID NO: 4)), an irrelevant peptide (YMFPNAPYL (SEQ ID NO: 76)) or no peptide. Using a 1:1 E:T ratio, the T2 cells were cocultured with EBNA Clone 315 CAR-expressing NK92MI cells in the presence of an anti- CD107a-PE conjugated antibody at 37° C. for 5 hours. As shown in FIG. 16A, NK92MI cells equipped with the EBNA Clone 315 CAR did not react to unpulsed T2 cells or T2 cells pulsed with the irrelevant peptide, showing CD107a levels comparable to those of NK92MI cells cultured in the absence of targets. On the other hand, when the CAR-equipped NK92MI cells were cocultured with T2 cells that had been pulsed with the LLDFVRFMGV (SEQ ID NO: 4) peptide, 27% of GFP$^+$ cells expressed CD107a above background levels. These results show that after scFv engineering, the CAR is able to maintain its specificity towards the targeted HLA-A2-peptide complex.

Next, in order to get a quantitative measurement of how sensitive this CAR is at activating NK92MI cells, we titrated down the LLDFVRFMGV (SEQ ID NO: 4) peptide concentration used to pulse T2 cells and measured their ability to activate the CAR-equipped NK92MI cells. As can be seen in FIG. 16B, the lower limit of response by the CAR-equipped NK92MI was at a peptide concentration of 10 nM, with a clear dose response curve beginning at the 600 nM concentration. Based on our earlier quantitation studies, this peptide concentration corresponds to approximately 25 complexes on the cell surface. Compared to the levels necessary for epitope detection using the EBNA Clone 315 scFv or scFv-Fc (200-20 nM), the CAR seems to be a more sensitive approach at detecting low levels of MHC-peptide complex on the surface of APCs using flow cytometric analysis.

Figure 17:
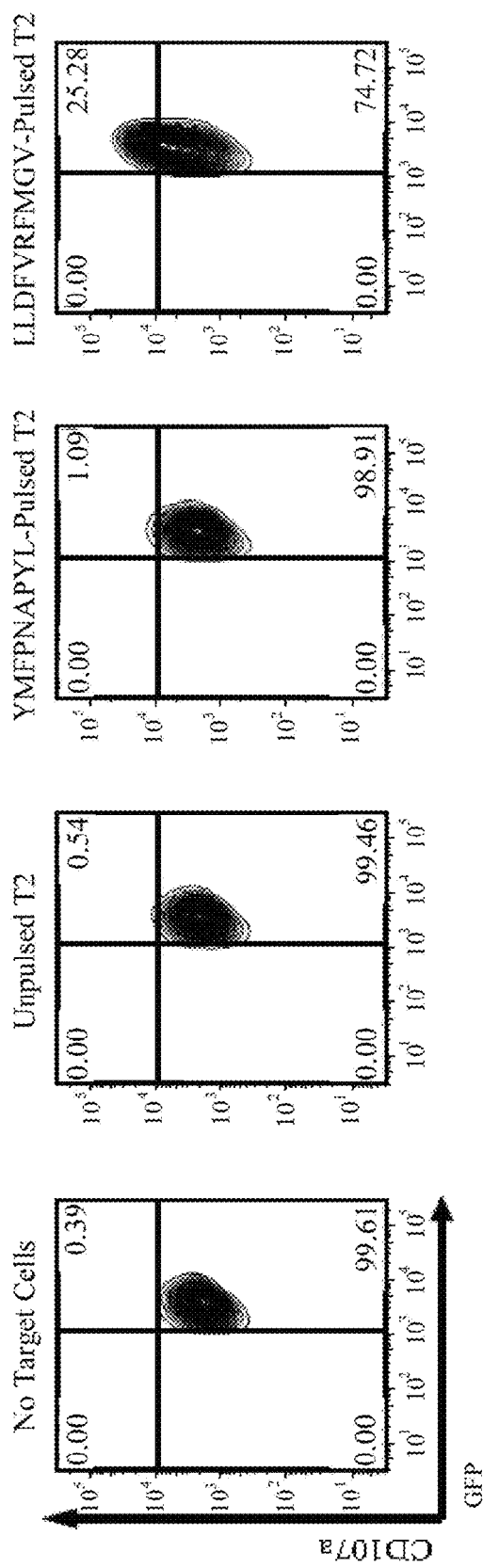
FIG. 17 shows the results of flow cytometry in which HLA-A2$^+$ (DIMT) and HLA-A2$^-$ (6268A) BLCLs were pulsed with LLDFVRFMGV (SEQ ID NO: 4) and CAR-equipped NK92MI cells were then cultured in media containing an anti-CD107a-PE conjugated antibody with or without peptide pulsed or unpulsed cells. CAR-equipped NK92MI cells were gated based on GFP fluorescence and analyzed for CD107a expression. NK92MI cells which were cultured without any BLCL or those which were cocultured with LLDFVRFMGV (SEQ ID NO: 4)-pulsed 6268A BLCL were unreactive while NK92MI cells which were cocultured with unpulsed DIMT BLCL or LLDFVRFMGV (SEQ ID NO: 4)-pulsed DIMT BLCL led to a 0.5% and 25% increase in CD107a expression above background levels (pulsed 6268A) showing that EBNA Clone 315 CAR-expressing NK92MI cells can specifically detect the HLA-A2-EBNA3C complex on peptide-pulsed BLCLs via CD107a expression.

While T2 cells can present any peptide of interest, BLCLs naturally present their own peptides on their MHC Class I molecules. Similarly to T2, these endogenous peptides can be replaced by simple incubation with a substitute peptide of high enough affinity. Using a 1:1 E:T ratio, HLA-A2$^+$ (DIMT) and HLA-A2$^-$ (6268A) BLCLs were pulsed with serum-free IMDM medium or medium containing the LLD-FVRFMGV (SEQ ID NO: 4), cocultured with EBNA Clone 315 CAR-expressing NK92MI cells as discussed above, and assayed for CD107a expression using flow cytometry. Peptide pulsed DIMT (HLA-A2$^+$) induced 25% of GFP$^+$ NK92MI cells to express CD107a (FIG. 17), in contrast to 0.54% for peptide pulsed 6268A (HLA-A2$^-$) and 1.09% for unpulsed DIMT. This data further demonstrates both peptide specificity and HLA-A2 exclusivity of the EBNA Clone 315 CAR.

Example 28

Figure 18:
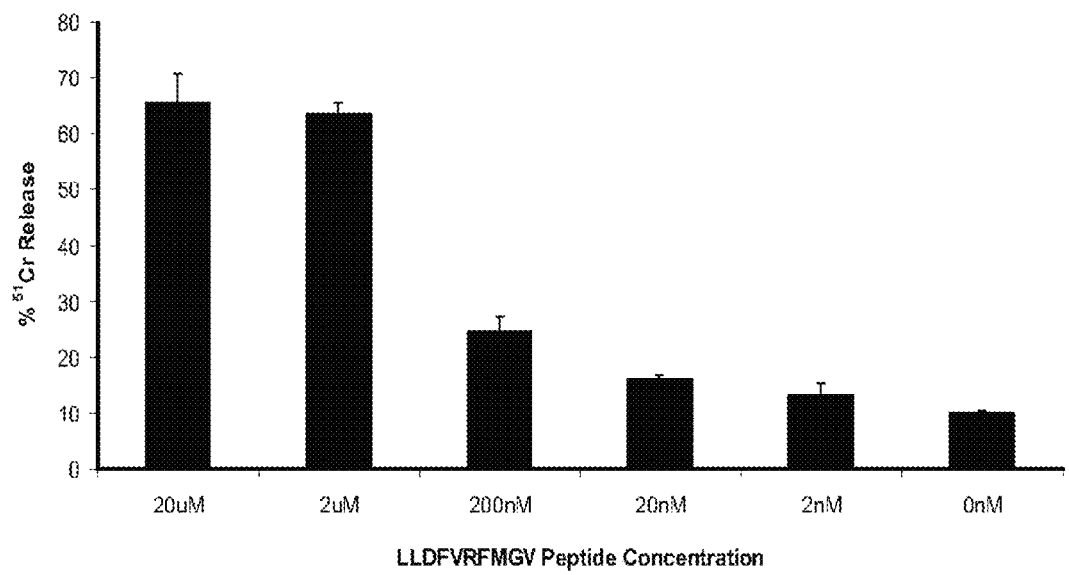
FIG. 18 shows the results of a $^{51}$Cr release assay in which T2 cells were pulsed with or without decreasing concentrations of LLDFVRFMGV (SEQ ID NO: 4). CAR-equipped NK92MI cells were cocultured with $^{51}$Cr-labeled T2 cells at a 3:1 E:T ratio demonstrating that EBNA Clone 315 CAR-expressing NK92MI cells can specifically detect the HLA-A2-EBNA3C complex on peptide-pulsed T2 cells. Even with 2 nM of peptide, peptide-specific cytotoxicity could be observed when compared to unpulsed T2 cells.

EBNA Clone 315 CAR-Equipped NK92MI Cells can Destroy Cells Bearing the Specific HLA-A2-LLDFVRFMGV (SEQ ID NO: 4) Complex Via $^{51}$Cr Release While CD107a expression on NK cells and T cells reflect their activation, target cell lysis can also be measured using a conventional $^{51}$Cr cytotoxicity assay. First, to get an idea of how sensitive the $^{51}$Cr cytotoxicity assay is with regards to killing HLA-A2-EBNA3C expressing targets, T2 cells were pulsed with decreasing concentrations of the LLD-FVRFMGV (SEQ ID NO: 4) peptide at 37° C. for 3 hours and subsequently labeled with $^{51}$Cr as described in the Materials and Methods. The labeled T2 cells were then cocultured with EBNA Clone 315 CAR-expressing NK92MI cells at 37° C. for 2 hours at a 3:1 E:T ratio. Similar to the results seen in the CD107a assay (FIG. 16B), EBNA Clone 315 CAR expressing NK92MI cells were able kill T2 cells in a peptide-dependent manner, with 13.2% of 2 nM peptide-pulsed T2 cells being killed compared to 10.1% with unpulsed T2 cells (FIG. 18). Relative to that which can be detected using flow cytometric antibody staining, the level of sensitivity is in the order of 10-100 fold greater in favor of the CAR using two separate assays (CD107a and $^{51}$Cr).

Figure 19:
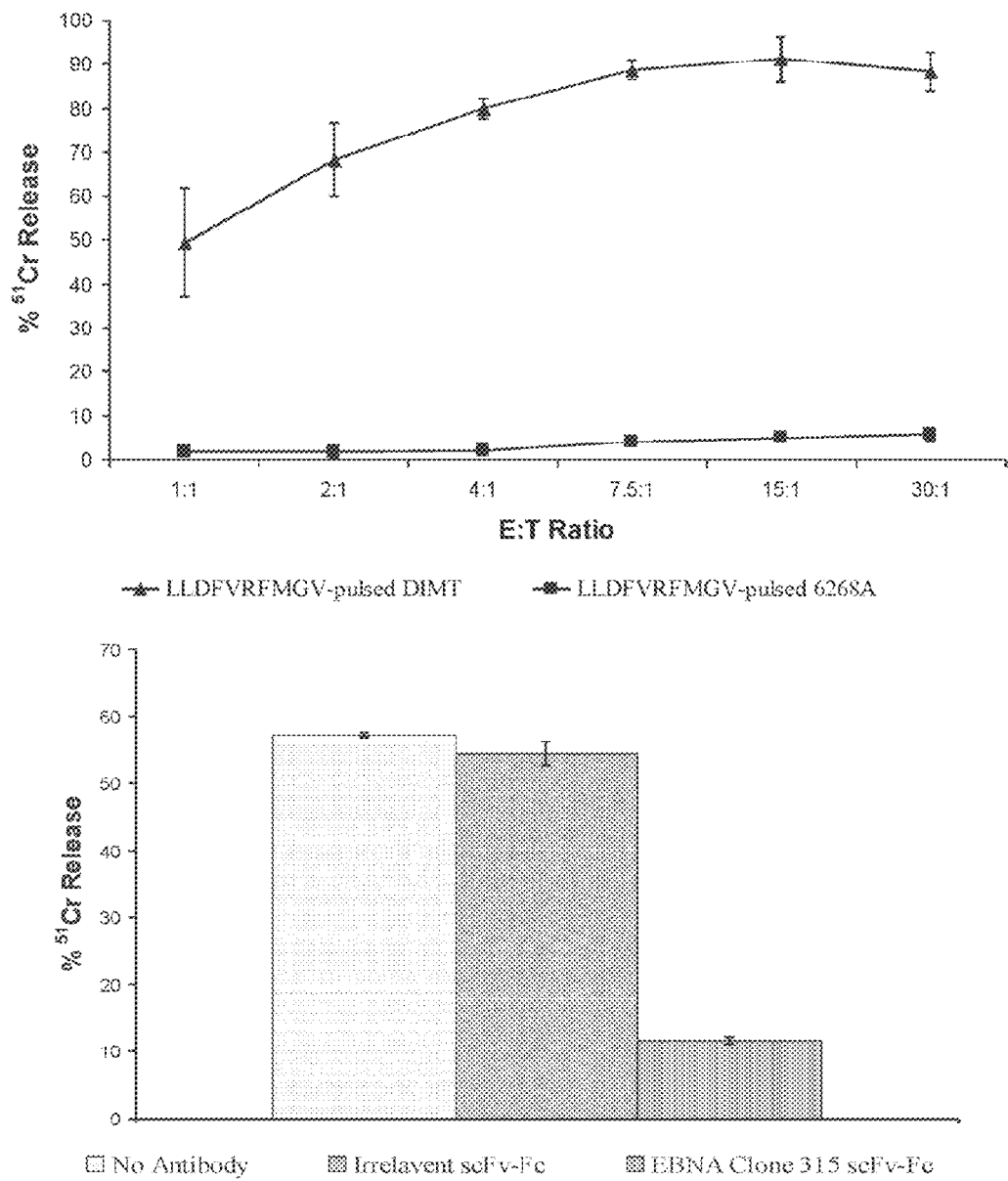
FIG. 19 shows EBNA Clone 315 CAR-expressing NK92MI cells can specifically detect the HLA-A2-EBNA3C complex on peptide-pulsed BLCLs via $^{51}$Cr release. BLCLs were pulsed with LLDFVRFMGV (SEQ ID NO: 4). CAR-equipped NK92MI cells were then cultured with $^{51}$Cr labeled target cells.

Next, DIMT and 6268A BLCLs pulsed with the LLD-FVRFMGV (SEQ ID NO: 4) peptide (20 µM) in serum-free IMDM (FIGS. 19A and B) were used as targets in the $^{51}$Cr release assay. Similar to the results from the CD107a assay (FIG. 17), only the HLA-A2$^+$ DIMT BLCL were lysed by the CAR-equipped NK92MI cells (FIG. 19A), which could be blocked using the purified EBNA Clone 315 scFv-Fc (FIG. 19B). In addition, the ability to block cytotoxicity was not restricted to the scFv-Fc protein since a commercial anti-HLA-A2 (BB7.2) antibody also possessed blocking ability (data not shown). This blocking data recapitulates results seen with other MHC-restricted, peptide-specific antibodies on antigen-specific cytolytic T cells.

Figure 20:
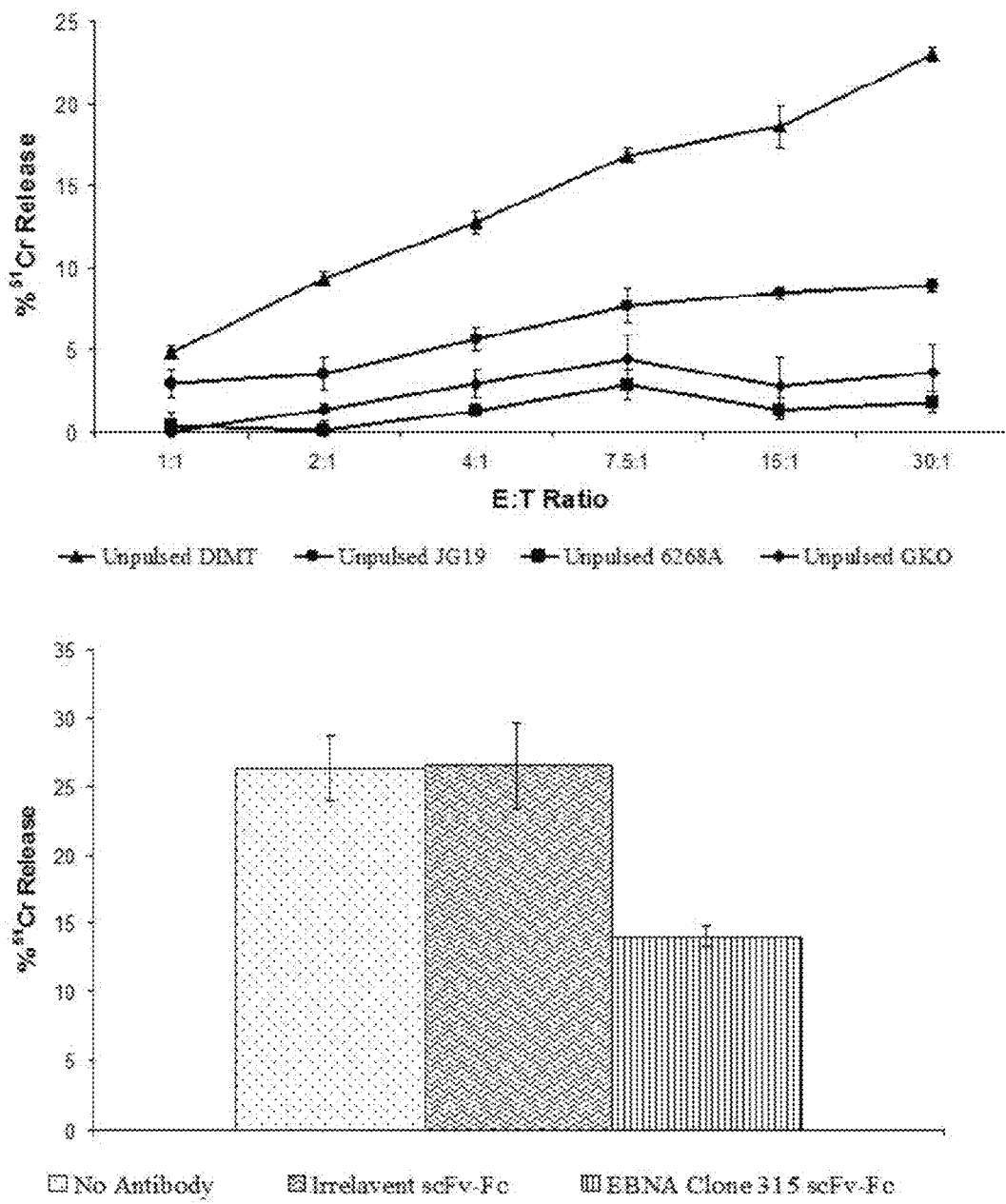
FIG. 20 shows the results of a $^{51}$Cr release assay in which CAR-equipped NK92MI cells were cultured with $^{51}$Cr labeled, unpulsed BLCLs.

Although the lytic potential of the CAR-equipped NK92MI cells was clearly evident when targets were artificially pulsed with the relevant peptide, cytotoxicity against naturally processed HLA-A2-peptide complexes is of clinical relevance. Here, CAR-equipped NK92MI cells were tested against a panel of HLA-A2$^+$ (DIMT and JG19) and HLA-A2$^-$ (6268A and GKO) unpulsed BLCLs. While the level of cytotoxicity was low, 23.0% for DIMT and 8.9% for JG19 (30:1 E:T ratio), this was highly significant when compared to 3.6% for GKO and 1.8% for 6268A (FIG. 20A). In addition, when the cytotoxicity assay was performed in the presence of EBNA Clone 315 scFv-Fc, the killing capacity could be reduced by approximately 46% when compared to that with an irrelevant scFv-Fc or in the absence of antibody (FIG. 20B). These findings demonstrate the utility and specificity of TCR-like CARs in reprogramming effector immune cells to engage antigen whose expression is below the detection limit using conventional flow cytometry.

Figure 21:
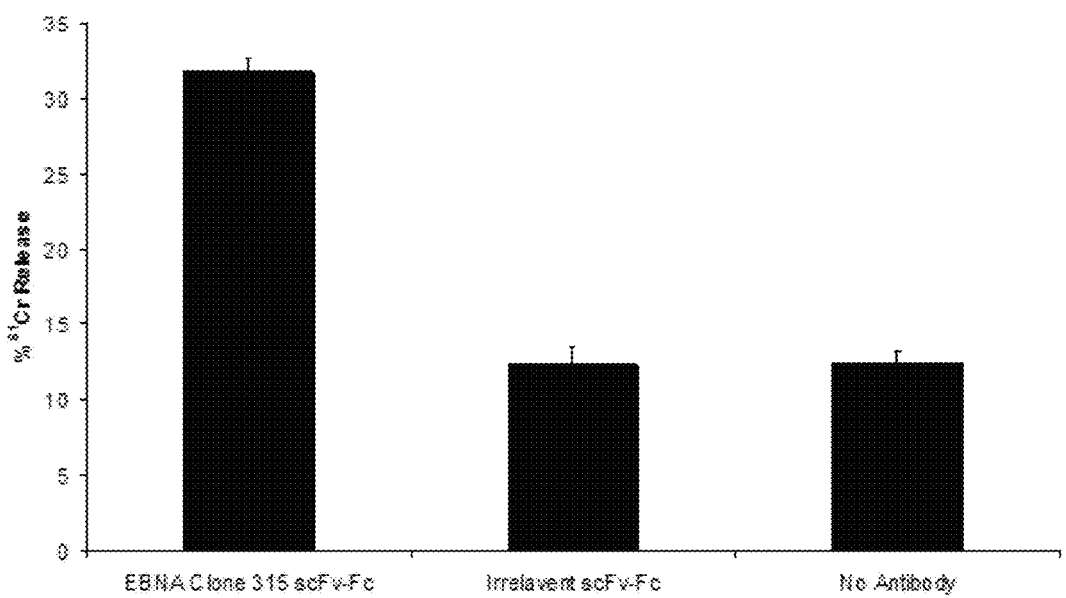
FIG. 21 shows the results of a $^{51}$Cr release assay of EBNA in which CD16(V)-expressing NK92MI cells were cultured with $^{51}$Cr labeled, LLDFVRFMGV- (SEQ ID NO: 4) pulsed DIMT BLCL and either EBNA Clone 315 or an irrelevant scFv-Fc. At an E:T ratio of 15:1, EBNA Clone 315 scFv-Fc was able to kill 30-35% of target cells.
Figure 22:
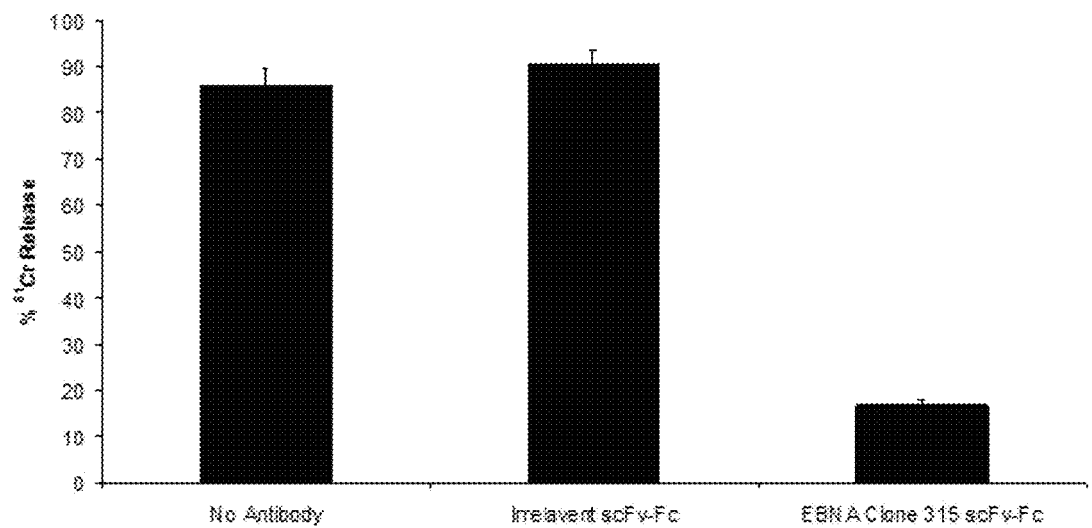
FIG. 22 shows the results of a $^{51}$Cr release assay of EBNA in which Clone 315 CAR-expressing NK92MI cells were cultured with LLDFVRFMGV (SEQ ID NO: 4) -pulsed DIMT BLCL as above and either EBNA Clone 315 or an irrelevant scFv-Fc. At the same E:T ratio as in FIG. 21, the CAR-equipped cells were able to kill 80-90% of target cells, with specific inhibition using EBNA Clone scFv-Fc demonstrating that CAR-mediated killing is more potent than scFv-Fc-mediated ADCC on peptide-pulsed DIMT BLCL.

Lastly, since both the EBNA Clone 315 CAR and scFv-Fc fusion protein have the same variable sequences used for detecting the HLA-A2-LLDFVRFMGV (SEQ ID NO: 4) complex, we decided to directly compare CAR-mediated cytotoxicity with ADCC since both approaches are currently being used independently for the treatment of cancer patients. First, the DIMT BLCL was pulsed with the LLD-FVRFMGV (SEQ ID NO: 4) peptide at 20 µM in serum-free IMDM media at 37° C. for 2 hours. The pulsed BLCL was then labeled with $^{51}$Cr and cocultured with either EBNA Clone 315 CAR or CD16(V)-expressing NK92MI cells along with EBNA Clone 315 scFv-Fc or an irrelevant scFv-Fc at an E:T ratio of 15:1 for 3 hours at 37° C. At a EBNA Clone 315 scFv-Fc concentration of 0.5 µg/ml, CD16(V) NK92MI cells were able to kill about 30-35% of cells, compared to 10-15% with an irrelevant scFv-Fc or no antibody at all (FIG. 21). When the ADCC experiment was carried out using higher scFv-Fc concentrations, the cytotoxicity percentage did not change (data not shown). On the other hand, at the same E:T ratio, EBNA Clone 315 CAR-equipped NK92MI cells were able to kill 80-90% of the same peptide-pulsed target cells; and the EBNA Clone 315 scFv-Fc was included as a blocking control (FIG. 22). These results demonstrate that the CAR-mediated killing involving NK92MI cells is a far more potent means of target cell lysis compared to ADCC in our setting.

Example 29

Figure 24:
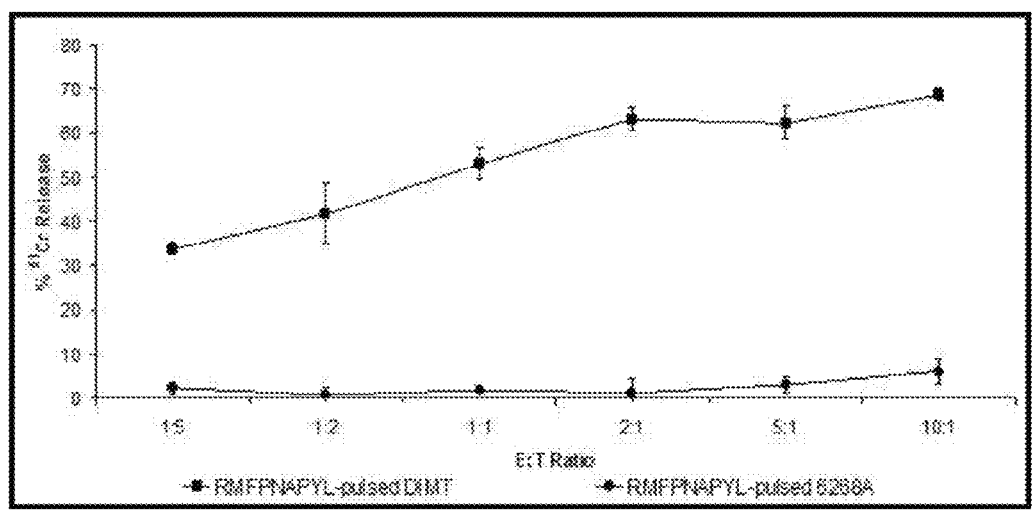
FIG. 24 shows the results of a $^{51}$Cr release assay in which CAR-equipped NK92MI cells were able to specifically differentiate between peptide pulsed DIMT (■) and 6268A BLCL (●), with a clear difference in cytotoxicity between the two different targets demonstrating that NK92MI cells expressing WT1 Clone 45 CAR can specifically detect the HLA-A2-RMFPNAPYL (SEQ ID NO: 1) complex on peptide-pulsed BLCLs.
Figure 25:
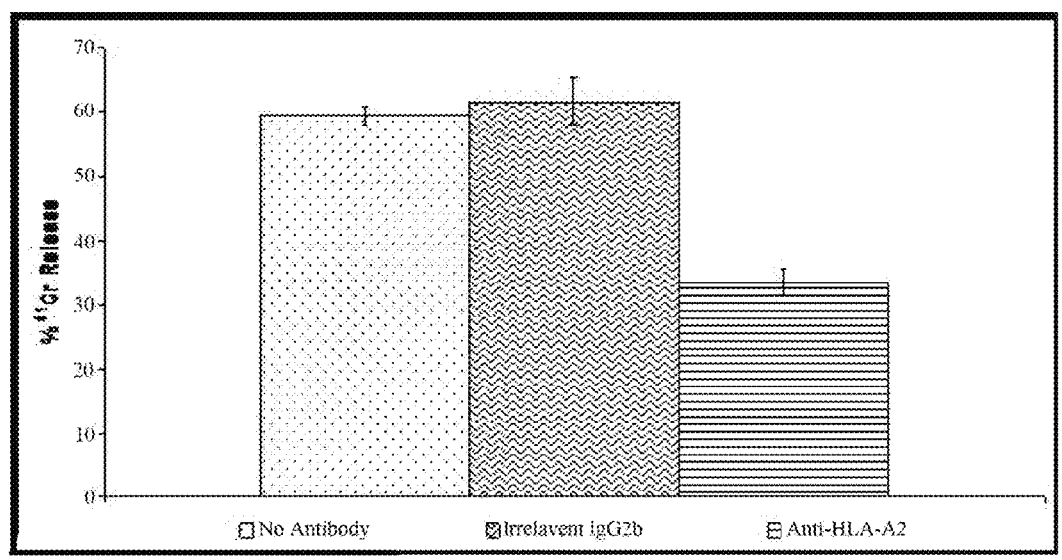
FIG. 25 shows that CAR-mediated killing of peptide-pulsed DIMT BLCL could be blocked using a commercial anti-HLA-A2 antibody (5 µg/ml), but not by an irrelevant, isotype-matched antibody (5 µg/ml), at a 9:1 E:T ratio.

WT1 Clone 45 CAR-Equipped NK92MI Cells can Destroy Cells Bearing the Specific HLA-A2-RMFPNAPYL (SEQ ID NO: 1) Complex Via $^{51}$Cr Release Along with the EBNA Clone 315 CAR, we decided to test the cytolytic ability of the WT1 Clone 45 CAR in the context of NK92MI cells. First, DIMT and 6268A BLCLs were pulsed with the RMFPNAPYL (SEQ ID NO: 1) peptide (40 μg/ml) in serum-free IMDM at 37° C. for 3-5 hours. Subsequently, the target cells were labeled with $^{51}$Cr and cocultured with the CAR-equipped NK92MI cells at 37° C. for 4 hours. Of the two peptide-pulsed BLCLs, only the HLA-A2$^+$ DIMT could be lysed (~70% versus ~5% with 6268A) at a 10:1 E:T ratio (FIG. 24). In addition, CAR-mediated cytotoxicity could be blocked using a commercial anti-HLA-A2 antibody by approximately 45% (FIG. 25), further demonstrating specificity.

Figure 26:
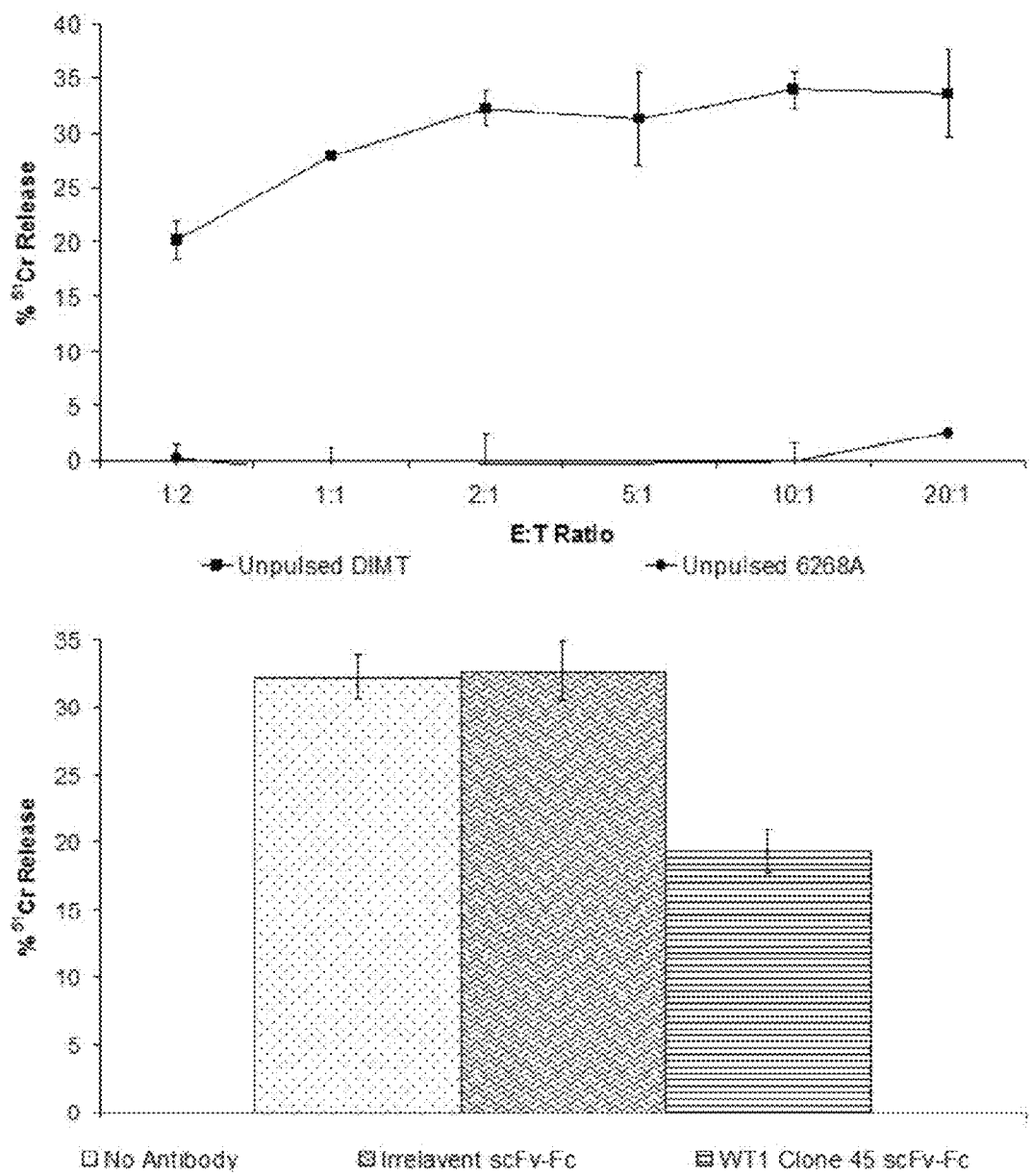
FIG. 26 shows that NK92MI cells expressing WT1 Clone 45 CAR can specifically detect the HLA-A2-RMFPNAPYL (SEQ ID NO: 1) complex on DIMT BLCL via $^{51}$Cr release.
Figure 27:
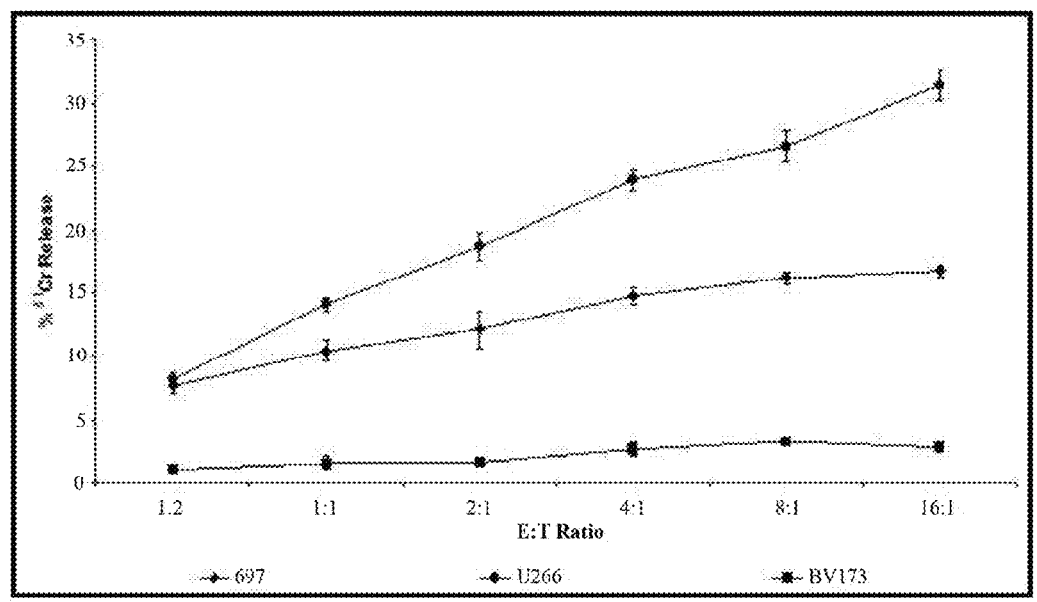
FIG. 27 shows that NK92MI cells expressing WT1 Clone 45 CAR can specifically detect the HLA-A2-RMFPNAPYL (SEQ ID NO: 1) complex on peptide-pulsed BLCLs via $^{51}$Cr release. A CAR-equipped NK92MI cells were able to specifically differentiate between peptide pulsed DIMT and 6268A BLCL, with a clear difference in cytotoxicity between the two different targets.
Figure 28:
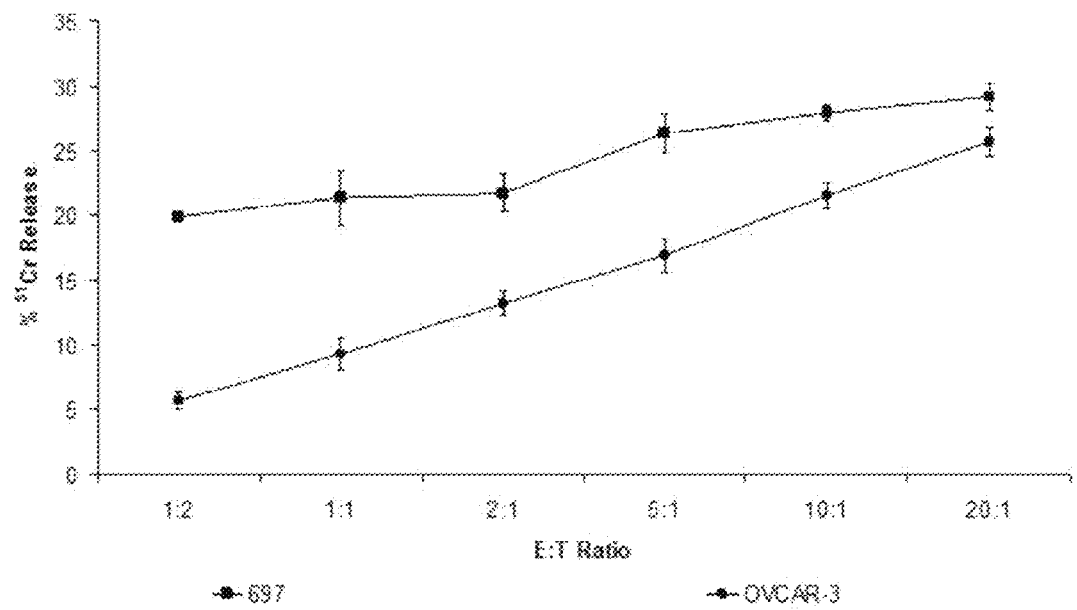
FIG. 28 shows that NK92MI cells expressing WT1 Clone 45 CAR can specifically detect the HLA-A2-RMFPNAPYL (SEQ ID NO: 4) complex on 697 and OVCAR-3 cells via $^{51}$Cr release.

Next, we decided to tested the cytolytic capacity of WT1 Clone 45 CAR-equipped NK92MI cells against cell lines which might natively express the HLA-A2-RMFPNAPYL (SEQ ID NO: 1) complex. Due to previously published data (92), and conversations with Dr. Richard O'Reilly's laboratory here at MSKCC, researchers have demonstrated that WT1 can be constitutively activated in all BLCLs derived from EBV immortalization. More specifically, O'Reilly's group was able to show WT1 transcript in the DIMT BLCL (data not shown). As a result, we first decided to test WT1 Clone 45 CAR-mediated killing against unpulsed HLA-A2$^+$ DIMT and HLA-A2$^-$ 6268A BLCL. Similarly to what was seen with the EBNA Clone 315 CAR, WT1 Clone 45 CAR-equipped NK92MI cells were able to kill unpulsed DIMT at a lower capacity than peptide-pulsed DIMT. While the level of cytotoxicity was lower, ~35% for DIMT at a 20:1 E:T ratio, it was far greater when compared to 6268A (~5%) (FIG. 26A). In addition, when the cytotoxicity assay was performed in the presence of the WT1 Clone 45 scFv-Fc, the killing capacity could be reduced by approximately 43% relative to an irrelevant scFv-Fc or in the absence of antibody (FIG. 26B). These findings correspond well with what was seen using the EBNA Clone 315 CAR and further demonstrate the utility and specificity of TCR-like CARs in reprogramming effector immune cells to engage antigen.

Lastly, CAR-mediated cytotoxicity against two cell lines which are HLA-A2-positive and previously shown to express WT1 was tested. OVCAR-3 is a cell line established from malignant ascites of a patient with progressive adenocarcinoma of the ovary (93) and later shown to contain WT1 mRNA (94). In addition, 697 is a human pre-B cell leukemia established from bone marrow cells obtained from a child with relapsed acute lymphocytic leukemia (ALL) (95). Since then, several groups have shown that this cell line also expresses high levels of both WT1 transcript and protein (96, 97). WT1 Clone 45 CAR-expressing NK92MI cells were cocultured with $^{51}$Cr labeled OVCAR-3 and 697 cells at 37° C. for 4 hours. CAR-equipped NK92MI cells were able to lyse approximately 20-30% of 697 and OVCAR-3 cells at a 20:1 E:T ratio, which decreased with the number of effector cells used in the assay. This data demonstrates that these two cell types are sensitive to WT1 Clone 45 CAR-equipped NK92MI cells and provides further evidence for their utility in the treatment of HLA-A2$^+$/WT1$^+$ malignancies.

EQUIVALENTS

The foregoing written specification is considered to be sufficient to enable one skilled in the art to practice the invention. The foregoing description and Examples detail certain embodiments of the invention and describes the best mode contemplated by the inventors. It will be appreciated, however, that no matter how detailed the foregoing may appear, the invention may be practiced in many ways and the invention should be construed in accordance with the appended claims and any equivalents thereof.

REFERENCES

1. Kohler, G., and C. Milstein. 1975. Continuous cultures of fused cells secreting antibody of predefined specificity. *Nature* 256:495-497.
2. Oldham, R. K., and R. O. Dillman. 2008. Monoclonal antibodies in cancer therapy: 25 years of progress. *J Clin Oncol* 26:1774-1777.
3. Tassev, D. V., and N. K. Cheung. 2009. Monoclonal antibody therapies for solid tumors. *Expert opinion on biological therapy* 9:341-353.
4. Fridman, W. H. 1991. Fc receptors and immunoglobulin binding factors. *Faseb J* 5:2684-2690.
5. Kratz, F., I. A. Muller, C. Ryppa, and A. Warnecke. 2008. Prodrug strategies in anticancer chemotherapy. *ChemMedChem* 3:20-53.
6. Magdelaine-Beuzelin, C., Q. Kaas, V. Wehbi, M. Ohresser, R. Jefferis, M. P. Lefranc, and H. Watier. 2007. Structure-function relationships of the variable domains of monoclonal antibodies approved for cancer treatment. *Critical reviews in oncology/hematology* 64:210-225.
7. Schmidt, M. M., and K. D. Wittrup. 2009. A modeling analysis of the effects of molecular size and binding affinity on tumor targeting. *Molecular cancer therapeutics* 8:2861-2871.
8. Kloetzel, P. M., and F. Ossendorp. 2004. Proteasome and peptidase function in MHC-class-I-mediated antigen presentation. *Current opinion in immunology* 16:76-81.
9. Donaldson, J. G., and D. B. Williams. 2009. Intracellular assembly and trafficking of MHC class I molecules. *Traffic (Copenhagen, Denmark)* 10:1745-1752.
10. Hunt, D. F., R. A. Henderson, J. Shabanowitz, K. Sakaguchi, H. Michel, N. Sevilir, A. L. Cox, E. Appella, and V. H. Engelhard. 1992. Characterization of peptides bound to the class I MHC molecule HLA-A2.1 by mass spectrometry. *Science* (New York, N.Y. 255:1261-1263.
11. Hofmann, S., M. Gluckmann, S. Kausche, A. Schmidt, C. Corvey, R. Lichtenfels, C. Huber, C. Albrecht, M. Karas, and W. Herr. 2005. Rapid and sensitive identification of major histocompatibility complex class I-associated tumor peptides by Nano-LC MALDI MS/MS. *Mol Cell Proteomics* 4:1888-1897.
12. Smith, G. P. 1985. Filamentous fusion phage: novel expression vectors that display cloned antigens on the virion surface. *Science* (New York, N.Y. 228:1315-1317.
13. Carmen, S., and L. Jermutus. 2002. Concepts in antibody phage display. *Briefings in functional genomics & proteomics* 1:189-203.
14. Baeuerle, P. A., and C. Reinhardt. 2009. Bispecific T-cell engaging antibodies for cancer therapy. *Cancer research* 69:4941-4944.
15. Bratkovic, T. 2010. Progress in phage display: evolution of the technique and its application. *Cell Mol Life Sci* 67:749-767.
16. Kourilov, V., and M. Steinitz. 2002. Magnetic-bead enzyme-linked immunosorbent assay verifies adsorption of ligand and epitope accessibility. *Analytical biochemistry* 311:166-170.
17. Andersen, P. S., A. Stryhn, B. E. Hansen, L. Fugger, J. Engberg, and S. Buus. 1996. A recombinant antibody with the antigen-specific, major histocompatibility complex-restricted specificity of T cells. *Proceedings of the National Academy of Sciences of the United States of America* 93:1820-1824.

18. Porgador, A., J. W. Yewdell, Y. Deng, J. R. Bennink, and R. N. Germain. 1997. Localization, quantitation, and in situ detection of specific peptide-MHC class I complexes using a monoclonal antibody. *Immunity* 6:715-726.
19. Zhong, G., C. Reis e Sousa, and R. N. Germain. 1997. Production, specificity, and functionality of monoclonal antibodies to specific peptide-major histocompatibility complex class II complexes formed by processing of exogenous protein. *Proceedings of the National Academy of Sciences of the United States of America* 94:13856-13861.
20. Dadaglio, G., C. A. Nelson, M. B. Deck, S. J. Petzold, and E. R. Unanue. 1997. Characterization and quantitation of peptide-MHC complexes produced from hen egg lysozyme using a monoclonal antibody. *Immunity* 6:727-738.
21. Lev, A., G. Denkberg, C. J. Cohen, M. Tzukerman, K. L. Skorecki, P. Chames, H. R. Hoogenboom, and Y. Reiter. 2002. Isolation and characterization of human recombinant antibodies endowed with the antigen-specific, major histocompatibility complex-restricted specificity of T cells directed toward the widely expressed tumor T-cell epitopes of the telomerase catalytic subunit. *Cancer research* 62:3184-3194.
22. Chames, P., S. E. Hufton, P. G. Coulie, B. Uchanska-Ziegler, and H. R. Hoogenboom. 2000. Direct selection of a human antibody fragment directed against the tumor T-cell epitope HLA-A1-MAGE-A1 from a nonimmunized phage-Fab library. *Proceedings of the National Academy of Sciences of the United States of America* 97:7969-7974.
23. Denkberg, G., C. J. Cohen, A. Lev, P. Chames, H. R. Hoogenboom, and Y. Reiter. 2002. Direct visualization of distinct T cell epitopes derived from a melanoma tumor-associated antigen by using human recombinant antibodies with MHC-restricted T cell receptor-like specificity. *Proceedings of the National Academy of Sciences of the United States of America* 99:9421-9426.
24. Held, G., M. Matsuo, M. Epel, S. Gnjatic, G. Ritter, S. Y. Lee, T. Y. Tai, C. J. Cohen, L. J. Old, M. Pfreundschuh, Y. Reiter, H. R. Hoogenboom, and C. Renner. 2004. Dissecting cytotoxic T cell responses towards the NY-ESO-1 protein by peptide/MHC-specific antibody fragments. *European journal of immunology* 34:2919-2929.
25. Held, G., A. Wadle, N. Dauth, G. Stewart-Jones, S. Sturm, M. Thiel, C. Zwick, D. Dieckmann, G. Schuler, H. R. Hoogenboom, F. Levy, V. Cerundolo, M. Pfreundschuh, and C. Renner. 2007. MHC-peptide-specific antibodies reveal inefficient presentation of an HLA-A*0201-restricted, Melan-A-derived peptide after active intracellular processing. *European journal of immunology* 37:2008-2017.
26. Klechevsky, E., M. Gallegos, G. Denkberg, K. Palucka, J. Banchereau, C. Cohen, and Y. Reiter. 2008. Antitumor activity of immunotoxins with T-cell receptor-like specificity against human melanoma xenografts. *Cancer research* 68:6360-6367.
27. Cohen, C. J., O. Sarig, Y. Yamano, U. Tomaru, S. Jacobson, and Y. Reiter. 2003. Direct phenotypic analysis of human MHC class I antigen presentation: visualization, quantitation, and in situ detection of human viral epitopes using peptide-specific, MHC-restricted human recombinant antibodies. *J Immunol* 170:4349-4361.
28. Cohen, C. J., N. Hoffmann, M. Farago, H. R. Hoogenboom, L. Eisenbach, and Y. Reiter. 2002. Direct detection and quantitation of a distinct T-cell epitope derived from tumor-specific epithelial cell-associated mucin using human recombinant antibodies endowed with the antigen-specific, major histocompatibility complex-restricted specificity of T cells. *Cancer research* 62:5835-5844.
29. Epel, M., I. Carmi, S. Soueid-Baumgarten, S. K. Oh, T. Bera, I. Pastan, J. Berzofsky, and Y. Reiter. 2008. Targeting TARP, a novel breast and prostate tumor-associated antigen, with T cell receptor-like human recombinant antibodies. *European journal of immunology* 38:1706-1720.
30. Neumann, F., C. Sturm, M. Hulsmeyer, N. Dauth, P. Guillaume, I. F. Luescher, M. Pfreundschuh, and G. Held. 2009. Fab antibodies capable of blocking T cells by competitive binding have the identical specificity but a higher affinity to the MHC-peptide-complex than the T cell receptor. *Immunology letters* 125:86-92.
31. Makler, O., K. Oved, N. Netzer, D. Wolf, and Y. Reiter. 2010. Direct visualization of the dynamics of antigen presentation in human cells infected with cytomegalovirus revealed by antibodies mimicking TCR specificity. *European journal of immunology* 40:1552-1565.
32. Michaeli, Y., G. Denkberg, K. Sinik, L. Lantzy, C. Chih-Sheng, C. Beauverd, T. Ziv, P. Romero, and Y. Reiter. 2009. Expression hierarchy of T cell epitopes from melanoma differentiation antigens: unexpected high level presentation of tyrosinase-HLA-A2 Complexes revealed by peptide-specific, MHC-restricted, TCR-like antibodies. *J Immunol* 182:6328-6341.
33. Weidanz, J. A., P. Piazza, H. Hickman-Miller, D. Woodburn, T. Nguyen, A. Wahl, F. Neethling, M. Chiriva-Internati, C. R. Rinaldo, and W. H. Hildebrand. 2007. Development and implementation of a direct detection, quantitation and validation system for class I MHC self-peptide epitopes. *Journal of immunological methods* 318:47-58.
34. Verma, B., O. E. Hawkins, F. A. Neethling, S. L. Caseltine, S. R. Largo, W. H. Hildebrand, and J. A. Weidanz. 2009. Direct discovery and validation of a peptide/MHC epitope expressed in primary human breast cancer cells using a TCRm monoclonal antibody with profound antitumor properties. *Cancer Immunol Immunother* 59:563-573.
35. Verma, B., F. A. Neethling, S. Caseltine, G. Fabrizio, S. Largo, J. A. Duty, P. Tabaczewski, and J. A. Weidanz. 2010. TCR mimic monoclonal antibody targets a specific peptide/HLA class I complex and significantly impedes tumor growth in vivo using breast cancer models. *J Immunol* 184:2156-2165.
36. Wittman, V. P., D. Woodburn, T. Nguyen, F. A. Neethling, S. Wright, and J. A. Weidanz. 2006. Antibody targeting to a class I MHC-peptide epitope promotes tumor cell death. *J Immunol* 177:4187-4195.
37. Reiter, Y., A. Di Carlo, L. Fugger, J. Engberg, and I. Pastan. 1997. Peptide-specific killing of antigen-presenting cells by a recombinant antibody-toxin fusion protein targeted to major histocompatibility complex/peptide class I complexes with T cell receptor-like specificity. *Proceedings of the National Academy of Sciences of the United States of America* 94:4631-4636.
38. Stewart-Jones, G., A. Wadle, A. Hombach, E. Shenderov, G. Held, E. Fischer, S. Kleber, N. Nuber, F. Stenner-Liewen, S. Bauer, A. McMichael, A. Knuth, H. Abken, A. A. Hombach, V. Cerundolo, E. Y. Jones, and C. Renner. 2009. Rational development of high-affinity T-cell receptor-like antibodies. *Proceedings of the National Academy of Sciences of the United States of America* 106:5784-5788.

39. Willemsen, R. A., R. Debets, E. Hart, H. R. Hoogenboom, R. L. Bolhuis, and P. Chames. 2001. A phage display selected fab fragment with MHC class I-restricted specificity for MAGE-A1 allows for retargeting of primary human T lymphocytes. *Gene therapy* 8:1601-1608.
40. Chames, P., R. A. Willemsen, G. Rojas, D. Dieckmann, L. Rem, G. Schuler, R. L. Bolhuis, and H. R. Hoogenboom. 2002. TCR-like human antibodies expressed on human CTLs mediate antibody affinity-dependent cytolytic activity. *J Immunol* 169:1110-1118.
41. Willemsen, R. A., C. Ronteltap, P. Chames, R. Debets, and R. L. Bolhuis. 2005. T cell retargeting with MHC class I-restricted antibodies: the CD28 costimulatory domain enhances antigen-specific cytotoxicity and cytokine production. *J Immunol* 174:7853-7858.
42. Doubrovina, E. S., M. M. Doubrovin, S. Lee, J. H. Shieh, G. Heller, E. Pamer, and R. J. O'Reilly. 2004. In vitro stimulation with WT1 peptide-loaded Epstein-Barr virus-positive B cells elicits high frequencies of WT1 peptide-specific T cells with in vitro and in vivo tumoricidal activity. *Clin Cancer Res* 10:7207-7219.
43. Hiasa, A., H. Nishikawa, M. Hirayama, S. Kitano, S. Okamoto, H. Chono, S. S. Yu, J. Mineno, Y. Tanaka, N. Minato, I. Kato, and H. Shiku. 2009. Rapid alphabeta TCR-mediated responses in gammadelta T cells transduced with cancer-specific TCR genes. *Gene therapy* 16:620-628.
44. Ochi, T., H. Fujiwara, and M. Yasukawa. 2010. Application of adoptive T-cell therapy using tumor antigen-specific T-cell receptor gene transfer for the treatment of human leukemia. *Journal of biomedicine & biotechnology* 2010: 521248.
45. Davies, D. M., and J. Maher. 2010. Adoptive T-cell immunotherapy of cancer using chimeric antigen receptor-grafted T cells. *Archivum immunologiae et therapiae experimentalis* 58:165-178.
46. Yee, C. 2010. Adoptive therapy using antigen-specific T-cell clones. *Cancer journal* (Sudbury, Mass. 16:367-373.
47. Bucks, C. M., J. A. Norton, A. C. Boesteanu, Y. M. Mueller, and P. D. Katsikis. 2009. Chronic antigen stimulation alone is sufficient to drive CD8+ T cell exhaustion. *J Immunol* 182:6697-6708.
48. Okamoto, S., J. Mineno, H. Ikeda, H. Fujiwara, M. Yasukawa, H. Shiku, and I. Kato. 2009. Improved expression and reactivity of transduced tumor-specific TCRs in human lymphocytes by specific silencing of endogenous TCR. *Cancer research* 69:9003-9011.
49. Cartellieri, M., M. Bachmann, A. Feldmann, C. Bippes, S. Stamova, R. Wehner, A. Temme, and M. Schmitz. 2010. Chimeric antigen receptor-engineered T cells for immunotherapy of cancer. *Journal of biomedicine & biotechnology* 2010: 956304.
50. Eshhar, Z., T. Waks, G. Gross, and D. G. Schindler. 1993. Specific activation and targeting of cytotoxic lymphocytes through chimeric single chains consisting of antibody-binding domains and the gamma or zeta subunits of the immunoglobulin and T-cell receptors. *Proceedings of the National Academy of Sciences of the United States of America* 90:720-724.
51. Weijtens, M. E., R. A. Willemsen, D. Valerio, K. Stam, and R. L. Bolhuis. 1996. Single chain Ig/gamma gene-redirected human T lymphocytes produce cytokines, specifically lyse tumor cells, and recycle lytic capacity. *J Immunol* 157:836-843.
52. Lamers, C. H., S. C. Langeveld, C. M. Groot-van Ruijven, R. Debets, S. Sleijfer, and J. W. Gratama. 2007. Gene-modified T cells for adoptive immunotherapy of renal cell cancer maintain transgene-specific immune functions in vivo. *Cancer Immunol Immunother* 56:1875-1883.
53. Lamers, C. H., S. Sleijfer, A. G. Vulto, W. H. Kruit, M. Kliffen, R. Debets, J. W. Gratama, G. Stoter, and E. Oosterwijk. 2006. Treatment of metastatic renal cell carcinoma with autologous T-lymphocytes genetically retargeted against carbonic anhydrase IX: first clinical experience. *J Clin Oncol* 24:e20-22.
54. Kershaw, M. H., J. A. Westwood, L. L. Parker, G. Wang, Z. Eshhar, S. A. Mavroukakis, D. E. White, J. R. Wunderlich, S. Canevari, L. Rogers-Freezer, C. C. Chen, J. C. Yang, S. A. Rosenberg, and P. Hwu. 2006. A phase I study on adoptive immunotherapy using gene-modified T cells for ovarian cancer. *Clin Cancer Res* 12:6106-6115.
55. Till, B. G., M. C. Jensen, J. Wang, E. Y. Chen, B. L. Wood, H. A. Greisman, X. Qian, S. E. James, A. Raubitschek, S. J. Forman, A. K. Gopal, J. M. Pagel, C. G. Lindgren, P. D. Greenberg, S. R. Riddell, and O. W. Press. 2008. Adoptive immunotherapy for indolent non-Hodgkin lymphoma and mantle cell lymphoma using genetically modified autologous CD20-specific T cells. *Blood* 112:2261-2271.
56. Pule, M. A., B. Savoldo, G. D. Myers, C. Rossig, H. V. Russell, G. Dotti, M. H. Huls, E. Liu, A. P. Gee, Z. Mei, E. Yvon, H. L. Weiss, H. Liu, C. M. Rooney, H. E. Heslop, and M. K. Brenner. 2008. Virus-specific T cells engineered to coexpress tumor-specific receptors: persistence and antitumor activity in individuals with neuroblastoma. *Nature medicine* 14:1264-1270.
57. Subramanian, C., S. Hasan, M. Rowe, M. Hottiger, R. Orre, and E. S. Robertson. 2002. Epstein-Barr virus nuclear antigen 3C and prothymosin alpha interact with the p300 transcriptional coactivator at the CH1 and CH3/HAT domains and cooperate in regulation of transcription and histone acetylation. *Journal of virology* 76:4699-4708.
58. Epstein, M. A., G. Henle, B. G. Achong, and Y. M. Barr. 1965. Morphological and Biological Studies on a Virus in Cultured Lymphoblasts from Burkitt's Lymphoma. *The Journal of experimental medicine* 121:761-770.
59. Cohen, J. I. 2000. Epstein-Barr virus infection. *The New England journal of medicine* 343:481-492.
60. Garrido, J. L., S. Maruo, K. Takada, and A. Rosendorff. 2009. EBNA3C interacts with Gadd34 and counteracts the unfolded protein response. *Virology journal* 6:231.
61. Kerr, B. M., N. Kienzle, J. M. Burrows, S. Cross, S. L. Silins, M. Buck, E. M. Benson, B. Coupar, D. J. Moss, and T. B. Sculley. 1996. Identification of type B-specific and cross-reactive cytotoxic T-lymphocyte responses to Epstein-Barr virus. *Journal of virology* 70:8858-8864.
62. Yang, L., Y. Han, F. Suarez Saiz, and M. D. Minden. 2007. A tumor suppressor and oncogene: the WT1 story. *Leukemia* 21:868-876.
63. Sugiyama, H. 2010. WT1 (Wilms' tumor gene 1): biology and cancer immunotherapy. *Japanese journal of clinical oncology* 40:377-387.
64. Coppes, M. J., C. E. Campbell, and B. R. Williams. 1993. The role of WT1 in Wilms tumorigenesis. *Faseb J* 7:886-895.
65. O'Reilly, R. J., T. Dao, G. Koehne, D. Scheinberg, and E. Doubrovina. 2010. Adoptive transfer of unselected or leukemia-reactive T-cells in the treatment of relapse following allogeneic hematopoietic cell transplantation. *Seminars in immunology* 22:162-172.

66. Rezvani, K., J. M. Brenchley, D. A. Price, Y. Kilical, E. Gostick, A. K. Sewell, J. Li, S. Mielke, D. C. Douek, and A. J. Barrett. 2005. T-cell responses directed against multiple HLA-A*0201-restricted epitopes derived from Wilms' tumor 1 protein in patients with leukemia and healthy donors: identification, quantification, and characterization. *Clin Cancer Res* 11:8799-8807.

67. Borbulevych, O. Y., P. Do, and B. M. Baker. 2010. Structures of native and affinity-enhanced WT1 epitopes bound to HLA-A*0201: implications for WT1-based cancer therapeutics. *Molecular immunology* 47:2519-2524.

68. Gao, L., I. Bellantuono, A. Elsasser, S. B. Marley, M. Y. Gordon, J. M. Goldman, and H. J. Stauss. 2000. Selective elimination of leukemic CD34(+) progenitor cells by cytotoxic T lymphocytes specific for WT1. *Blood* 95:2198-2203.

69. Mailander, V., C. Scheibenbogen, E. Thiel, A. Letsch, I. W. Blau, and U. Keilholz. 2004. Complete remission in a patient with recurrent acute myeloid leukemia induced by vaccination with WT1 peptide in the absence of hematological or renal toxicity. *Leukemia* 18:165-166.

70. Keilholz, U., A. Letsch, A. Busse, A. M. Asemissen, S. Bauer, I. W. Blau, W. K. Hofmann, L. Uharek, E. Thiel, and C. Scheibenbogen. 2009. A clinical and immunologic phase 2 trial of Wilms tumor gene product 1 (WT1) peptide vaccination in patients with AML and MDS. *Blood* 113:6541-6548.

71. Garboczi, D. N., P. Ghosh, U. Utz, Q. R. Fan, W. E. Biddison, and D. C. Wiley. 1996. Structure of the complex between human T-cell receptor, viral peptide and HLA-A2. *Nature* 384:134-141.

72. Garboczi, D. N., U. Utz, P. Ghosh, A. Seth, J. Kim, E. A. VanTienhoven, W. E. Biddison, and D. C. Wiley. 1996. Assembly, specific binding, and crystallization of a human TCR-alphabeta with an antigenic Tax peptide from human T lymphotropic virus type 1 and the class I MHC molecule HLA-A2. *J Immunol* 157:5403-5410.

73. Altman, J. D., P. A. Moss, P. J. Goulder, D. H. Barouch, M. G. McHeyzer-Williams, J. I. Bell, A. J. McMichael, and M. M. Davis. 1996. Phenotypic analysis of antigen-specific T lymphocytes. *Science* (New York, N. Y 274:94-96.

74. Busch, D. H., I. M. Pilip, S. Vijh, and E. G. Pamer. 1998. Coordinate regulation of complex T cell populations responding to bacterial infection. *Immunity* 8:353-362.

75. Schatz, P. J. 1993. Use of peptide libraries to map the substrate specificity of a peptide-modifying enzyme: a 13 residue consensus peptide specifies biotinylation in *Escherichia coli*. *Bio/technology* (Nature Publishing Company) 11:1138-1143.

76. de Wildt, R. M., C. R. Mundy, B. D. Gorick, and I. M. Tomlinson. 2000. Antibody arrays for high-throughput screening of antibody-antigen interactions. *Nature biotechnology* 18:989-994.

77. Imai, C., K. Mihara, M. Andreansky, I. C. Nicholson, C. H. Pui, T. L. Geiger, and D. Campana. 2004. Chimeric receptors with 4-1BB signaling capacity provoke potent cytotoxicity against acute lymphoblastic leukemia. *Leukemia* 18:676-684.

78. Kim, Y. J., S. H. Kim, P. Mantel, and B. S. Kwon. 1998. Human 4-1BB regulates CD28 co-stimulation to promote Th1 cell responses. *European journal of immunology* 28:881-890.

79. Hurtado, J. C., Y. J. Kim, and B. S. Kwon. 1997. Signals through 4-1BB are costimulatory to previously activated splenic T cells and inhibit activation-induced cell death. *J Immunol* 158:2600-2609.

80. Jackson, R. J., M. T. Howell, and A. Kaminski. 1990. The novel mechanism of initiation of picornavirus RNA translation. *Trends in biochemical sciences* 15:477-483.

81. Baas, E. J., H. M. van Santen, M. J. Kleijmeer, H. J. Geuze, P. J. Peters, and H. L. Ploegh. 1992. Peptide-induced stabilization and intracellular localization of empty HLA class I complexes. *The Journal of experimental medicine* 176:147-156.

82. Koehne, G., K. M. Smith, T. L. Ferguson, R. Y. Williams, G. Heller, E. G. Pamer, B. Dupont, and R. J. O'Reilly. 2002. Quantitation, selection, and functional characterization of Epstein-Barr virus-specific and alloreactive T cells detected by intracellular interferon-gamma production and growth of cytotoxic precursors. *Blood* 99:1730-1740.

83. Gould, L. H., J. Sui, H. Foellmer, T. Oliphant, T. Wang, M. Ledizet, A. Murakami, K. Noonan, C. Lambeth, K. Kar, J. F. Anderson, A. M. de Silva, M. S. Diamond, R. A. Koski, W. A. Marasco, and E. Fikrig. 2005. Protective and therapeutic capacity of human single-chain Fv-Fc fusion proteins against West Nile virus. *Journal of virology* 79:14606-14613.

84. van der Merwe, P. A., and S. J. Davis. 2003. Molecular interactions mediating T cell antigen recognition. *Annual review of immunology* 21:659-684.

85. Sykulev, Y., R. J. Cohen, and H. N. Eisen. 1995. The law of mass action governs antigen-stimulated cytolytic activity of CD8+ cytotoxic T lymphocytes. *Proceedings of the National Academy of Sciences of the United States of America* 92:11990-11992.

86. Schodin, B. A., T. J. Tsomides, and D. M. Kranz. 1996. Correlation between the number of T cell receptors required for T cell activation and TCR-ligand affinity. *Immunity* 5:137-146.

87. Cartron, G., L. Dacheux, G. Salles, P. Solal-Celigny, P. Bardos, P. Colombat, and H. Watier. 2002. Therapeutic activity of humanized anti-CD20 monoclonal antibody and polymorphism in IgG Fc receptor FcgammaRIIIa gene. *Blood* 99:754-758.

88. Weng, W. K., R. S. Negrin, P. Lavori, and S. J. Horning. Immunoglobulin G Fc receptor FcgammaRIIIa 158 V/F polymorphism correlates with rituximab-induced neutropenia after autologous transplantation in patients with non-Hodgkin's lymphoma. *J Clin Oncol* 28:279-284.

89. George, A. J., J. Stark, and C. Chan. 2005. Understanding specificity and sensitivity of T-cell recognition. *Trends in immunology* 26:653-659.

90. Betts, M. R., J. M. Brenchley, D. A. Price, S. C. De Rosa, D. C. Douek, M. Roederer, and R. A. Koup. 2003. Sensitive and viable identification of antigen-specific CD8+ T cells by a flow cytometric assay for degranulation. *Journal of immunological methods* 281:65-78.

91. Alter, G., J. M. Malenfant, and M. Altfeld. 2004. CD107a as a functional marker for the identification of natural killer cell activity. *Journal of immunological methods* 294:15-22.

92. Spinsanti, P., U. de Grazia, A. Faggioni, L. Frati, A. Calogero, and G. Ragona. 2000. Wilms' tumor gene expression by normal and malignant human B lymphocytes. *Leukemia & lymphoma* 38:611-619.

93. Hamilton, T. C., R. C. Young, W. M. McKoy, K. R. Grotzinger, J. A. Green, E. W. Chu, J. Whang-Peng, A. M. Rogan, W. R. Green, and R. F. Ozols. 1983. Characterization of a human ovarian carcinoma cell line (NIH: OVCAR-3) with androgen and estrogen receptors. *Cancer research* 43:5379-5389.

94. Viel, A., F. Giannini, E. Capozzi, V. Canzonieri, C. Scarabelli, A. Gloghini, and M. Boiocchi. 1994. Molecular mechanisms possibly affecting WT1 function in human ovarian tumors. *International journal of cancer* 57:515-521.
95. Findley, H. W., Jr., M. D. Cooper, T. H. Kim, C. Alvarado, and A. H. Ragab. 1982. Two new acute lymphoblastic leukemia cell lines with early B-cell phenotypes. *Blood* 60:1305-1309.
96. Krug, L. M., T. Dao, A. B. Brown, P. Maslak, W. Travis, S. Bekele, T. Korontsvit, V. Zakhaleva, J. Wolchok, J. Yuan, H. Li, L. Tyson, and D. A. Scheinberg. 2010. WT1 peptide vaccinations induce CD4 and CD8 T cell immune responses in patients with mesothelioma and non-small cell lung cancer. *Cancer Immunol Immunother* 59:1467-1479.
97. Chaise, C., S. L. Buchan, J. Rice, J. Marquet, H. Rouard, M. Kuentz, G. E. Vittes, V. Molinier-Frenkel, J. P. Farcet, H. J. Stauss, M. H. Delfau-Larue, and F. K. Stevenson. 2008. DNA vaccination induces WT1-specific T-cell responses with potential clinical relevance. *Blood* 112:2956-2964.
98. Zhang, L., J. R. Conejo-Garcia, D. Katsaros, P. A. Gimotty, M. Massobrio, G. Regnani, A. Makrigiannakis, H. Gray, K. Schlienger, M. N. Liebman, S. C. Rubin, and G. Coukos. 2003. Intratumoral T cells, recurrence, and survival in epithelial ovarian cancer. *The New England journal of medicine* 348:203-213.
99. Odunsi, K., and L. J. Old. 2007. Tumor infiltrating lymphocytes: indicators of tumor-related immune responses. *Cancer Immun* 7:3.
100. Sun, J. C., J. N. Beilke, and L. L. Lanier. 2010. Immune memory redefined: characterizing the longevity of natural killer cells. *Immunological reviews* 236:83-94.
101. Tam, Y. K., B. Miyagawa, V. C. Ho, and H. G. Klingemann. 1999. Immunotherapy of malignant melanoma in a SCID mouse model using the highly cytotoxic natural killer cell line NK-92. *Journal of hematotherapy* 8:281-290.
102. Korbelik, M., and J. Sun. 2001. Cancer treatment by photodynamic therapy combined with adoptive immunotherapy using genetically altered natural killer cell line. *International journal of cancer* 93:269-274.
103. Arai, S., R. Meagher, M. Swearingen, H. Myint, E. Rich, J. Martinson, and H. Klingemann. 2008. Infusion of the allogeneic cell line NK-92 in patients with advanced renal cell cancer or melanoma: a phase I trial. *Cytotherapy* 10:625-632.
104. Yasukawa, M., H. Ohminami, S. Kaneko, Y. Yakushijin, Y. Nishimura, K. Inokuchi, T. Miyakuni, S. Nakao, K. Kishi, I. Kubonishi, K. Dan, and S. Fujita. 1998. CD4(+) cytotoxic T-cell clones specific for bcr-abl b3a2 fusion peptide augment colony formation by chronic myelogenous leukemia cells in a b3a2-specific and HLA-DR-restricted manner. *Blood* 92:3355-3361.
105. Chmielewski, M., A. Hombach, C. Heuser, G. P. Adams, and H. Abken. 2004. T cell activation by antibody-like immunoreceptors: increase in affinity of the single-chain fragment domain above threshold does not increase T cell activation against antigen-positive target cells but decreases selectivity. *J Immunol* 173:7647-7653.
106. Tomkinson, B., E. Robertson, and E. Kieff. 1993. Epstein-Barr virus nuclear proteins EBNA-3A and EBNA-3C are essential for B-lymphocyte growth transformation. *Journal of virology* 67:2014-2025.
107. Boissel, L. B., M. Van Etten, R A. and Klingemann, H G. 2009. Transfection of NK Cells with mRNA or Lentivirus Expressing Chimeric Antigen Receptors Results in Highly Efficient Killing of Lymphoid Malignancies and Compares Favorably with Monoclonal Antibody-Directed ADCC. In *51st ASH Annual Meeting and Exposition*, Ernest N. Morial Convention Center, New Orleans, La.
108. Mulder, A., C. Eijsink, M. J. Kardol, M. E. Franke-van Dijk, S. H. van der Burg, M. Kester, Doxiadis, I I, and F. H. Claas. 2003. Identification, isolation, and culture of HLA-A2-specific B lymphocytes using MHC class I tetramers. *J Immunol* 171:6599-6603.
109. Mulder, A., C. Eijsink, M. G. Kester, M. E. Franke, M. J. Kardol, M. H. Heemskerk, C. van Kooten, F. A. Verreck, J. W. Drijfhout, F. Koning, Doxiadis, I I, and F. H. Claas. 2005. Impact of peptides on the recognition of HLA class I molecules by human HLA antibodies. *J Immunol* 175:5950-5957.
110. Bansal, H., S. Bansal, M. Rao, K. P. Foley, J. Sang, D. A. Proia, R. K. Blackman, W. Ying, J. Barsoum, M. R. Baer, K. Kelly, R. Swords, G. E. Tomlinson, M. Battiwalla, F. J. Giles, K. P. Lee, and S. Padmanabhan. 2010. Heat shock protein 90 regulates the expression of Wilms tumor 1 protein in myeloid leukemias. *Blood* 116:4591-4599.
111. O'Reilly, R. J. 2008. Epstein-Barr virus sustains tumor killers. *Nature medicine* 14:1148-1150.
112. Milner, E., E. Barnea, I. Beer, and A. Admon. 2006. The turnover kinetics of major histocompatibility complex peptides of human cancer cells. *Mol Cell Proteomics* 5:357-365.
113. Vicent, S., R. Chen, L. C. Sayles, C. Lin, R. G. Walker, A. K. Gillespie, A. Subramanian, G. Hinkle, X. Yang, S. Saif, D. E. Root, V. Huff, W. C. Hahn, and E. A. Sweet-Cordero. 2010. Wilms tumor 1 (WT1) regulates KRAS-driven oncogenesis and senescence in mouse and human models. *The Journal of clinical investigation* 120:3940-3952.
114. Maruo, S., B. Zhao, E. Johannsen, E. Kieff, J. Zou, and K. Takada. 2011. Epstein-Barr virus nuclear antigens 3C and 3A maintain lymphoblastoid cell growth by repressing p16INK4A and p14ARF expression. *Proceedings of the National Academy of Sciences of the United States of America* 108:1919-1924.

The invention claimed is:

1. An antigen-binding protein comprising one of:
   (A) an antigen binding region having the amino acid sequence of SEQ ID NO: 5;
   (B) an antigen binding region comprising a $V_H$ and a $V_L$ respectively, with the amino acid sequences SEQ ID NOs: 24 and 25; or
   (C) (i)
      (a) a light chain (LC) complementarity determining region 1 (CDR1) comprising the amino acid sequence of SEQ ID NO: 56;
      (b) a LC CDR2 comprising the amino acid sequence of SEQ ID NO: 58; and
      (c) a LC CDR3 comprising the amino acid sequence of SEQ ID NO: 65; and
      (ii) (a) a heavy chain (HC) complementarity determining region 1 (CDR1) comprising the amino acid sequence of SEQ ID NO: 39;
         (b) a HC CDR2 comprising the amino acid sequence of SEQ ID NO: 41; and
         (c) a HC CDR3 comprising the amino acid sequence of SEQ ID NO: 49.

2. The antigen-binding protein of claim 1, wherein the antigen-binding protein is an antibody.

3. The antigen-binding protein of claim 2, wherein the antibody is a full-length antibody, an intact antibody, a Fab fragment, a F(ab')₂ fragment or a single chain variable fragment (scFv).

4. The antigen-binding protein of claim 1, wherein the antigen-binding protein is a chimeric antigen receptor (CAR).

5. The antigen-binding protein of claim 1, wherein the antigen-binding protein specifically binds to an epitope on an human leukocyte antigen (HLA)/peptide complex.

6. The isolated antigen-binding protein of claim 5, wherein the peptide of the HLA/peptide complex has the amino acid sequence LLDFVRFMGV (SEQ ID NO:4).

7. The isolated antigen-binding protein of claim 1, wherein the HLA of the HLA/peptide complex is HLA-A2.

8. A fusion protein comprising an antigen-binding protein of claim 1.

9. A single-chain variable fragment (scFv) comprising the amino acid sequences set forth in SEQ ID NO: 5.

10. A scFv comprising a $V_H$ and a $V_L$ linked by an amino acid spacer, wherein the $V_H$ and $V_L$ respectively comprise the amino acid sequences set forth in SEQ ID NOS: 24 and 25.

11. An immunoconjugate comprising a first component which is an antigen-binding protein or fragment thereof of claim 1.

12. The immunoconjugate of claim 11, comprising a second component having a second amino acid sequence.

13. The immunoconjugate of claim 12, further comprising a cytotoxin.

14. The immunoconjugate of claim 12, wherein the second component is a binding protein or antibody having a binding specificity for a target that is different from the HLA-peptide complex.

15. A bispecific antibody comprising an antigen-binding protein of claim 1.

16. A pharmaceutical composition comprising an antibody binding protein of claim 1.

* * * * *

SEQUENCE LISTING

<160> NUMBER OF SEQ ID NOS: 86

<210> SEQ ID NO 1
<211> LENGTH: 9
<212> TYPE: PRT
<213> ORGANISM: Homo sapiens

<400> SEQUENCE: 1

Arg Met Phe Pro Asn Ala Pro Tyr Leu
1               5

<210> SEQ ID NO 2
<211> LENGTH: 241
<212> TYPE: PRT
<213> ORGANISM: Homo sapiens

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gln Ile Asp Pro Trp Gly Gln Glu Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Thr Gly Arg Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ser Ala Ser Gln Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Gly Pro
    210                 215                 220

Gly Thr Pro Asn Thr Phe Gly Gln Gly Thr Lys Val Glu Ile Lys Arg
225                 230                 235                 240

Ala

<210> SEQ ID NO 3
<211> LENGTH: 723
<212> TYPE: DNA
<213> ORGANISM: Homo sapiens

<400> SEQUENCE: 3
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg gtctcacag attgatcctt ggggtcagga gacattgtac     180
gcagactccg tgaagggccg gttcaccatc tccagagaca attccaagaa cacgctgtat     240
ctgcaaatga acagcctgag agccgaggac acggccgtat attactgtgc gaaacttact     300
ggtcggtttg actactgggg ccagggaacc ctggtcaccg tctcaagcgg tggaggcggt     360

```
tcaggcggag gtggcagcgg cggtggcggg tcgacggaca tccagatgac ccagtctcca      420 tcctcccctgt ctgcatctgt aggagacaga gtcaccatca cttgccgggc aagtcagagc     480
attagcagct atttaaattg gtatcagcag aaaccaggga aagcccctaa gctcctgatc     540
tattcggcat cccagttgca aagtggggtc ccatcaaggt tcagtggcag tggatctggg     600
acagatttca ctctcaccat cagcagtctg caacctgaag attttgcaac ttactactgt    660
caacagggtc cggggactcc taatacgttc ggccaaggga ccaaggtgga aatcaaacgg    720
gcc                                                                  723
```

<210> SEQ ID NO 4
<211> LENGTH: 10
<212> TYPE: PRT
<213> ORGANISM: Homo sapiens

<400> SEQUENCE: 4

Leu Leu Asp Phe Val Arg Phe Met Gly Val
1               5                   10

<210> SEQ ID NO 5
<211> LENGTH: 241
<212> TYPE: PRT
<213> ORGANISM: Homo sapiens

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Met Ser Trp Val Arg Gln Ala Pro Gly Lys Gly Leu Glu Trp Val
        35                  40                  45

Ser Glu Ile Ala Pro Pro Gly Leu Asn Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Asp Thr Ala Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Leu Ala Ser Asn Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ala Glu
    210                 215                 220

Tyr Met Pro Leu Thr Phe Gly Gln Gly Thr Lys Val Glu Ile Lys Arg
225                 230                 235                 240

Ala

<210> SEQ ID NO 6
<211> LENGTH: 723
<212> TYPE: DNA
<213> ORGANISM: Homo sapiens

<400> SEQUENCE: 6

```
gaggtgcagc tgttggagtc tgggggaggc ttggtacagc ctgggggqtc cctgagactc      60
tcctgtgcag cctctggatt cacctttagc ggctatgcca tgagctgggt ccgccaggct     120
ccagggaagg ggctggagtg ggtctcagag attgcgccgc tggtttgaa tacacgttac      180
gcagactccg tgaagggccg gttcactatc tccagagaca attccaagaa cacgctgtat     240
ctgcaaatga acagcctgag agccgaggac acggccgtat attactgtgc gaaatcggat     300
actgcttttg actactgggg ccagggaacc ctggtcaccg tctcgagcgg tggaggcggt     360
tcaggcggag gtggcagcgg cggtggcggg tcgacggaca tccagatgac ccagtctcca     420
tcctcccctgt ctgcatctgt aggagacaga gtcaccatca cttgccgggc aagtcagagc    480
attagcagct atttaaattg gtatcagcag aaaccaggga aagcccctaa gctcctgatc     540
tatctggcat ccaatttgca aagtggggtc ccatcaaggt tcagtggcag tggatctggg     600
acagatttca ctctcaccat cagcagtctg caacctgaag attttgcaac ttactactgt     660
caacaggcgg agtatatgcc tctgacgttc ggccaaggga ccaaggtgga aatcaaacgg     720
gcc                                                                   723
```

<210> SEQ ID NO 7
<211> LENGTH: 9
<212> TYPE: PRT
<213> ORGANISM: Homo sapiens

<400> SEQUENCE: 7

Arg Leu Thr Arg Phe Leu Ser Arg Val
1               5

<210> SEQ ID NO 8
<211> LENGTH: 241
<212> TYPE: PRT
<213> ORGANISM: Homo sapiens

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Thr Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Asp Ser Asp Ala Thr Asp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Thr Thr Asp Tyr Phe Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Thr Asp Ile Gln Met Thr Gln Ser Pro Ser Ser Leu Ser Ala

-continued

```
                130                 135                 140
Ser Val Gly Asp Arg Val Thr Ile Thr Cys Arg Ala Ser Gln Ser Ile
145                 150                 155                 160

Ser Ser Tyr Leu Asn Trp Tyr Gln Gln Lys Pro Gly Lys Ala Pro Lys
                165                 170                 175

Leu Leu Ile Tyr Tyr Ala Ser Tyr Leu Gln Ser Gly Val Pro Ser Arg
                180                 185                 190

Phe Ser Gly Ser Gly Ser Gly Thr Asp Phe Thr Leu Thr Ile Ser Ser
                195                 200                 205

Leu Gln Pro Glu Asp Phe Ala Thr Tyr Tyr Cys Gln Gln Ser Ser Ser
                210                 215                 220

Ser Pro Asp Thr Phe Gly Gln Gly Thr Lys Val Glu Ile Lys Arg Ala
225                 230                 235                 240

Ala
```

<210> SEQ ID NO 9
<211> LENGTH: 723
<212> TYPE: DNA
<213> ORGANISM: Homo sapiens

<400> SEQUENCE: 9

```
gaggtgcagc tgttggagtc tgggggaggc ttggtacagc ctggggggtc cctgagactc     60
tcctgtgcaa cctctggatt cacctttagc agctatgcca tgagctgggt ccgccaggct    120
ccagggaagg gcctggagtg ggtctcaact atttctgata gtgatgctac agattacgca    180
gactccgtga agggcaggtt caccatctcc agagacaatt ccaagaacac gctgtatctg    240
caaatgaaca gcctgagagc cgaggacacg gccgtatatt actgtgcgaa aactactgat    300
tattttgact actggggcca gggaaccctg gtcaccgtct cgagcggtgg aggcggttca    360
ggcggaggtg gcagcggcgg tggcgggtcg acggacatcc agatgaccca gtctccatcc    420
tccctgtctg catctgtagg agacagagtc accatcactt gccgggcaag tcagagcatt    480
agcagctatt taaattggta tcagcagaaa ccagggaaag cccctaagct cctgatctat    540
tatgcatcct atttgcaaag tggggtccca tcaaggttca gtggcagtgg atctgggaca    600
gatttcactc tcaccatcag cagtctgcaa cctgaagatt ttgcaactta ctactgtcaa    660
cagtcttcta gttctcctga tacgttcggc caagggacca aggtggaaat caaacgggcg    720
gcc                                                                 723
```

<210> SEQ ID NO 10
<211> LENGTH: 242
<212> TYPE: PRT
<213> ORGANISM: Homo sapiens

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Asp Ile Ser Asp Asp Gly Asp Ala Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Lys Ser Ser Thr Thr Phe Asp Tyr Trp Gly Gln Gly Thr Leu Val
            100                 105                 110

Thr Val Ser Ser Gly Gly Gly Gly Ser Gly Gly Gly Gly Ser Gly Gly
            115                 120                 125

Gly Gly Ser Thr Asp Ile Gln Met Thr Gln Ser Pro Ser Ser Leu Ser
        130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ala Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Gly Thr
    210                 215                 220

Asp Ser Pro Ala Thr Phe Gly Gln Gly Thr Lys Val Glu Ile Lys Arg
225                 230                 235                 240

Ala Ala

<210> SEQ ID NO 11
<211> LENGTH: 726
<212> TYPE: DNA
<213> ORGANISM: Homo sapiens

<400> SEQUENCE: 11
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcagat atttctgatg atggtgatgc acatattac        180
gcagactccg tgaagggcag gttcaccatc tccagagaca attccaagaa cacgctgtat     240
ctgcaaatga acagcctgag agccgaggac acggccgtat attactgtgc gaaatcttct     300
actactttg actactgggg ccagggaacc ctggtcaccg tctcgagcgg tggaggcggt     360
tcaggcggag gtggcagcgg cggtggcggg tcgacggaca tccagatgac ccagtctcca     420
tcctccctgt ctgcatctgt aggagacaga gtcaccatca cttgccgggc aagtcagagc     480
attagcagct atttaaattg gtatcagcag aaaccaggga agcccctaa gctcctgatc     540
tatgctgcat ccgccttgca aagtggggtc ccatcaaggt tcagtggcag tggatctggg     600
acagatttca ctctcaccat cagcagtctg caacctgaag attttgcaac ttactactgt     660
caacagggta ctgatagtcc tgctacgttc ggccaaggga ccaaggtgga aatcaaacgg     720
gcggcc                                                                726

<210> SEQ ID NO 12
<211> LENGTH: 9
<212> TYPE: PRT
<213> ORGANISM: Homo sapiens

<400> SEQUENCE: 12

Arg Ile Ile Thr Ser Thr Ile Leu Val
1               5

<210> SEQ ID NO 13
```

```
<211> LENGTH: 240
<212> TYPE: PRT
<213> ORGANISM: Homo sapiens

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ala Ser Thr Gly Tyr Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Asn Ala Ser Phe Asp Tyr Trp Gly Gln Gly Thr Leu Val
            100                 105                 110

Thr Val Ser Ser Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Asp Ala Ser Thr Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Thr Asp
    210                 215                 220

Ser Tyr Pro Thr Thr Phe Gly Gln Gly Thr Lys Val Glu Ile Lys Arg
225                 230                 235                 240

<210> SEQ ID NO 14
<211> LENGTH: 240
<212> TYPE: PRT
<213> ORGANISM: Homo sapiens

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ser Ser Gly Ser Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ser Ser Phe Asp Tyr Trp Gly Gln Gly Thr Leu Val
            100                 105                 110
```

```
Thr Val Ser Ser Gly Gly Gly Ser Gly Gly Gly Ser Gly Gly
        115                 120                 125
Gly Gly Ser Thr Asp Ile Gln Met Thr Gln Ser Pro Ser Ser Leu Ser
130                 135                 140
Ala Ser Val Gly Asp Arg Val Thr Ile Thr Cys Arg Ala Ser Gln Ser
145                 150                 155                 160
Ile Ser Ser Tyr Leu Asn Trp Tyr Gln Gln Lys Pro Gly Lys Ala Pro
                165                 170                 175
Lys Leu Leu Ile Tyr Asp Ala Ser Thr Leu Gln Ser Gly Val Pro Ser
            180                 185                 190
Arg Phe Ser Gly Ser Gly Ser Gly Thr Asp Phe Thr Leu Thr Ile Ser
        195                 200                 205
Ser Leu Gln Pro Glu Asp Phe Ala Thr Tyr Tyr Cys Gln Gln Asp Asp
    210                 215                 220
Ala Tyr Pro Thr Thr Phe Gly Gln Gly Thr Lys Val Glu Ile Lys Arg
225                 230                 235                 240
```

<210> SEQ ID NO 15
<211> LENGTH: 720
<212> TYPE: DNA
<213> ORGANISM: Homo sapiens

<400> SEQUENCE: 15

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcggat attgcttcta ctggttatta tacagattac     180
gcagactccg tgaagggccg gttcaccatc tccagagaca attccaagaa cacgctgtat     240
ctgcaaatga acagcctgag agccgaggac acggccgtat attactgtgc gaaaaataat     300
gctagttttg actactgggg ccagggaacc ctggtcaccg tctcgagcgg tggaggcggt     360
tcaggcggag gtggcagcgg cggtggcggg tcgacggaca tccagatgac ccagtctcca     420
tcctccctgt ctgcatctgt aggagacaga gtcaccatca cttgccgggc aagtcagagc     480
attagcagct atttaaattg gtatcagcag aaaccaggga agcccctaa gctcctgatc      540
tatgatgcat ccactttgca agtggggtc ccatcaaggt tcagtggcag tggatctggg      600
acagatttca ctctcaccat cagcagtctg caacctgaag attttgcaac ttactactgt     660
caacagactg attcttatcc tactacgttc ggccaaggga ccaaggtgga aatcaaacgg     720
```

<210> SEQ ID NO 16
<211> LENGTH: 720
<212> TYPE: DNA
<213> ORGANISM: Homo sapiens

<400> SEQUENCE: 16

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcatct attagtagtt ctggtagtta tacagattac     180
gcagactccg tgaagggccg gttcaccatc tccagagaca attccaagaa cacgctgtat     240
ctgcaaatga acagcctgag agccgaggac acggccgtat attactgtgc gaaatctgct     300
tcttcttttg actactgggg ccagggaacc ctggtcaccg tctcgagcgg tggaggcggt     360
tcaggcggag gtggcagcgg cggtggcggg tcgacggaca tccagatgac ccagtctcca     420
```

```
tcctccctgt ctgcatctgt aggagacaga gtcaccatca cttgccgggc aagtcagagc      480
attagcagct atttaaattg gtatcagcag aaaccaggga aagcccctaa gctcctgatc      540
tatgatgcat ccactttgca aagtggggtc ccatcaaggt tcagtggcag tggatctggg      600
acagatttca ctctcaccat cagcagtctg caacctgaag attttgcaac ttactactgt      660
caacaggatg atgcttatcc tactacgttc ggccaaggga ccaaggtgga aatcaaacgg      720
```

<210> SEQ ID NO 17
<211> LENGTH: 240
<212> TYPE: PRT
<213> ORGANISM: Homo sapiens

<400> SEQUENCE: 17

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ser Asp Gly Ser Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr Asp Ala Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Tyr Leu Gln Ser Gly Val Pro Ser
            180                 185                 190

Arg Phe Ser Gly Ser Gly Ser Gly Thr Asp Phe Ser Leu Thr Ile Ser
        195                 200                 205

Ser Leu Gln Pro Glu Asp Phe Ala Thr Tyr Tyr Cys Gln Gln Asp Asn
    210                 215                 220

Asn Tyr Pro Thr Thr Phe Gly Gln Gly Thr Lys Val Glu Ile Lys Arg
225                 230                 235                 240
```

<210> SEQ ID NO 18
<211> LENGTH: 720
<212> TYPE: DNA
<213> ORGANISM: Homo sapiens

<400> SEQUENCE: 18

```
gaggtgcagc tgttggagtc tgggggaggc ttggtacagc ctggggggtc cctgagactc       60
tcctgtgcag cctctggatt cacctttagc agctatgcca tgagctgggt ccgccaggct      120
ccagggaagg ggctggagtg ggtctcaagt atttcttctg atggtagtta tacagattac      180
gcagactccg tgaagggccg gttcaccatc tccagagaca attccaagaa cacgctgtat      240
```

-continued

```
ctgcaaatga acagcctgag agccgaggac acggccgtat attactgtgc gaaatctact    300
gatgcttttg actactgggg ccagggaacc ctggtcaccg tctcgagcgg tggaggcggt    360
tcaggcggag gtggcagcgg cggtggcggg tcgacggaca tccagatgac ccagtctcca    420
tcctccctgt ctgcatctgt aggagacaga gtcaccatca cttgccgggc aagtcagagc    480
attagcagct atttaaattg gtatcagcag aaaccaggga agcccctaa gctcctgatc    540
tatgctgcat cctatttgca aagtggggtc ccatcaaggt tcagtggcag tggatctggg    600
acagatttct ctctcaccat cagcagtctg caacctgaag attttgcaac ttactactgt    660
caacaggata taattatcc tactacgttc ggccaaggga ccaaggtgga aatcaaacgg    720
```

<210> SEQ ID NO 19
<211> LENGTH: 9
<212> TYPE: PRT
<213> ORGANISM: Homo sapiens

<400> SEQUENCE: 19

Leu Leu Glu Glu Met Phe Leu Thr Val
1               5

<210> SEQ ID NO 20
<211> LENGTH: 240
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Asn Tyr Ser Gly Ser Gly Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ala Ala Tyr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Gly Ala Ser Gly Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Ala
    210                 215                 220

Asn Ala Pro Thr Thr Phe Gly Gln Gly Thr Lys Val Glu Ile Lys Arg
225                 230                 235                 240

<210> SEQ ID NO 21
<211> LENGTH: 720
<212> TYPE: DNA
<213> ORGANISM: Homo sapiens

<400> SEQUENCE: 21

```
gaggtgcagc tgttggagtc tgggggaggc ttggtacagc ctgggggdtc cctgagactc      60
tcctgtgcag cctctggatt cacctttagc agctatgcca tgagctgggt ccgccaggct     120
ccagggaagg ggctggagtg ggtctcaact attaattatt ctggttctgg tacaacttac     180
gcagactccg tgaagggcag gttcaccatc tccagagaca attccaagaa cacgctgtat     240
ctgcaaatga acagcctgag agccgaggac acggccgtat attactgtgc gaaaatgct      300
gcttattttg actactgggg ccagggaacc ctggtcaccg tctcgagcgg tggaggcggt     360
tcaggcggag gtggcagcgg cggtggcggg tcgacggaca tccagatgac ccagtctcca     420
tcctcccctgt ctgcatctgt aggagacaga gtcaccatca cttgccgggc aagtcagagc     480
attagcagct atttaaattg gtatcagcag aaaccaggga agcccctaa gctcctgatc      540
tatggtgcat ccggtttgca agtgggggtc ccatcaaggt tcagtggcag tggatctggg     600
acagatttca ctctcaccat cagcagtctg caacctgaag attttgcaac ttactactgt     660
caacagtctg ctaatgctcc tactacgttc ggccaaggga ccaaggtgga aatcaaacgg     720
```

<210> SEQ ID NO 22
<211> LENGTH: 115
<212> TYPE: PRT
<213> ORGANISM: Homo sapiens

<400> SEQUENCE: 22

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gln Ile Asp Pro Trp Gly Gln Glu Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Thr Gly Arg Phe Asp Tyr Trp Gly Gln Gly Thr Leu Val
            100                 105                 110

Thr Val Ser
        115
```

<210> SEQ ID NO 23
<211> LENGTH: 111
<212> TYPE: PRT
<213> ORGANISM: Homo sapiens

<400> SEQUENCE: 23

```
Ser Thr Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
            20                  25                  30
```

```
Ser Tyr Leu Asn Trp Tyr Gln Gln Lys Pro Gly Lys Ala Pro Lys Leu
        35                  40                  45

Leu Ile Tyr Ser Ala Ser Gln Leu Gln Ser Gly Val Pro Ser Arg Phe
 50                  55                  60

Ser Gly Ser Gly Ser Gly Thr Asp Phe Thr Leu Thr Ile Ser Ser Leu
 65                  70                  75                  80

Gln Pro Glu Asp Phe Ala Thr Tyr Tyr Cys Gln Gln Gly Pro Gly Thr
                 85                  90                  95

Pro Asn Thr Phe Gly Gln Gly Thr Lys Val Glu Ile Lys Arg Ala
                100                 105                 110
```

<210> SEQ ID NO 24
<211> LENGTH: 115
<212> TYPE: PRT
<213> ORGANISM: Homo sapiens

<400> SEQUENCE: 24

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Gly Tyr
                 20                  25                  30

Ala Met Ser Trp Val Arg Gln Ala Pro Gly Lys Gly Leu Glu Trp Val
        35                  40                  45

Ser Glu Ile Ala Pro Pro Gly Leu Asn Thr Arg Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Asp Thr Ala Phe Asp Tyr Trp Gly Gln Gly Thr Leu Val
                100                 105                 110

Thr Val Ser
        115
```

<210> SEQ ID NO 25
<211> LENGTH: 111
<212> TYPE: PRT
<213> ORGANISM: Homo sapiens

<400> SEQUENCE: 25

```
Ser Thr Asp Ile Gln Met Thr Gln Ser Pro Ser Ser Leu Ser Ala Ser
  1               5                  10                  15

Val Gly Asp Arg Val Thr Ile Thr Cys Arg Ala Ser Gln Ser Ile Ser
                 20                  25                  30

Ser Tyr Leu Asn Trp Tyr Gln Gln Lys Pro Gly Lys Ala Pro Lys Leu
        35                  40                  45

Leu Ile Tyr Leu Ala Ser Asn Leu Gln Ser Gly Val Pro Ser Arg Phe
 50                  55                  60

Ser Gly Ser Gly Ser Gly Thr Asp Phe Thr Leu Thr Ile Ser Ser Leu
 65                  70                  75                  80

Gln Pro Glu Asp Phe Ala Thr Tyr Tyr Cys Gln Gln Ala Glu Tyr Met
                 85                  90                  95

Pro Leu Thr Phe Gly Gln Gly Thr Lys Val Glu Ile Lys Arg Ala
                100                 105                 110
```

<210> SEQ ID NO 26
<211> LENGTH: 114

<212> TYPE: PRT
<213> ORGANISM: Homo sapiens

<400> SEQUENCE: 26

```
Glu Val Gln Leu Leu Glu Ser Gly Gly Gly Leu Val Gln Pro Gly Gly
1               5                   10                  15

Ser Leu Arg Leu Ser Cys Ala Thr Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Asp Ser Asp Ala Thr Asp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Thr Thr Asp Tyr Phe Asp Tyr Trp Gly Gln Gly Thr Leu Val Thr
            100                 105                 110

Val Ser
```

<210> SEQ ID NO 27
<211> LENGTH: 112
<212> TYPE: PRT
<213> ORGANISM: Homo sapiens

<400> SEQUENCE: 27

```
Ser Thr Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Tyr Ala Ser Tyr Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Ser Ser Ser
                85                  90                  95

Pro Asp Thr Phe Gly Gln Gly Thr Lys Val Glu Ile Lys Arg Ala Ala
            100                 105                 110
```

<210> SEQ ID NO 28
<211> LENGTH: 115
<212> TYPE: PRT
<213> ORGANISM: Homo sapiens

<400> SEQUENCE: 28

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ser Asp Asp Gly Asp Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Ser Ser Thr Thr Phe Asp Tyr Trp Gly Gln Gly Thr Leu Val
            100                 105                 110

Thr Val Ser
        115

<210> SEQ ID NO 29
<211> LENGTH: 112
<212> TYPE: PRT
<213> ORGANISM: Homo sapiens

<400> SEQUENCE: 29

Ser Thr Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Ala Ala Ser Ala Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Thr Tyr Asp Ser
                85                  90                  95

Pro Ala Thr Phe Gly Gln Gly Thr Lys Val Glu Ile Lys Arg Ala Ala
            100                 105                 110

<210> SEQ ID NO 30
<211> LENGTH: 115
<212> TYPE: PRT
<213> ORGANISM: Homo sapiens

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ala Ser Thr Gly Tyr Tyr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Asn Ala Ser Phe Asp Tyr Trp Gly Gln Gly Thr Leu Val
            100                 105                 110

Thr Val Ser
        115

<210> SEQ ID NO 31
<211> LENGTH: 110
<212> TYPE: PRT
<213> ORGANISM: Homo sapiens

<400> SEQUENCE: 31
```

```
Ser Thr Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Asp Ala Ser Thr Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Thr Asp Ser Tyr
                85                  90                  95

Pro Thr Thr Phe Gly Gln Gly Thr Lys Val Glu Ile Lys Arg
            100                 105                 110

<210> SEQ ID NO 32
<211> LENGTH: 115
<212> TYPE: PRT
<213> ORGANISM: Homo sapiens

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ser Ser Gly Ser Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ser Ser Phe Asp Tyr Trp Gly Gln Gly Thr Leu Val
            100                 105                 110

Thr Val Ser
    115

<210> SEQ ID NO 33
<211> LENGTH: 110
<212> TYPE: PRT
<213> ORGANISM: Homo sapiens

<400> SEQUENCE: 33

Ser Thr Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Asp Ala Ser Thr Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Asp Asp Ala Tyr
                85                  90                  95
```

-continued

Pro Thr Thr Phe Gly Gln Gly Thr Lys Val Glu Ile Lys Arg
            100                 105                 110

<210> SEQ ID NO 34
<211> LENGTH: 115
<212> TYPE: PRT
<213> ORGANISM: Homo sapiens

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ser Asp Gly Ser Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr Asp Ala Phe Asp Tyr Trp Gly Gln Gly Thr Leu Val
            100                 105                 110

Thr Val Ser
        115

<210> SEQ ID NO 35
<211> LENGTH: 110
<212> TYPE: PRT
<213> ORGANISM: Homo sapiens

<400> SEQUENCE: 35

Ser Thr Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Ala Ala Ser Tyr Leu Gln Ser Gly Val Pro Ser Arg Phe
    50                  55                  60

Ser Gly Ser Gly Ser Gly Thr Asp Phe Ser Leu Thr Ile Ser Ser Leu
65                  70                  75                  80

Gln Pro Glu Asp Phe Ala Thr Tyr Tyr Cys Gln Gln Asp Asn Asn Tyr
                85                  90                  95

Pro Thr Thr Phe Gly Gln Gly Thr Lys Val Glu Ile Lys Arg
            100                 105                 110

<210> SEQ ID NO 36
<211> LENGTH: 115
<212> TYPE: PRT
<213> ORGANISM: Homo sapiens

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val

```
            35                  40                  45
Ser Thr Ile Asn Tyr Ser Gly Ser Gly Thr Thr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asn Ala Ala Tyr Phe Asp Tyr Trp Gly Gln Gly Thr Leu Val
            100                 105                 110
Thr Val Ser
        115

<210> SEQ ID NO 37
<211> LENGTH: 110
<212> TYPE: PRT
<213> ORGANISM: Homo sapiens

<400> SEQUENCE: 37

Ser Thr Asp Ile Gln Met Thr Gln Ser Pro Ser Ser Leu Ser Ala Ser
 1               5                  10                  15
Val Gly Asp Arg Val Thr Ile Thr Cys Arg Ala Ser Gln Ser Ile Ser
             20                  25                  30
Ser Tyr Leu Asn Trp Tyr Gln Gln Lys Pro Gly Lys Ala Pro Lys Leu
         35                  40                  45
Leu Ile Tyr Gly Ala Ser Gly Leu Gln Ser Gly Val Pro Ser Arg Phe
     50                  55                  60
Ser Gly Ser Gly Ser Gly Thr Asp Phe Thr Leu Thr Ile Ser Ser Leu
 65                  70                  75                  80
Gln Pro Glu Asp Phe Ala Thr Tyr Tyr Cys Gln Gln Ser Ala Asn Ala
                 85                  90                  95
Pro Thr Thr Phe Gly Gln Gly Thr Lys Val Glu Ile Lys Arg
            100                 105                 110

<210> SEQ ID NO 38
<211> LENGTH: 5
<212> TYPE: PRT
<213> ORGANISM: Homo sapiens

<400> SEQUENCE: 38

Ser Tyr Ala Met Ser
 1               5

<210> SEQ ID NO 39
<211> LENGTH: 5
<212> TYPE: PRT
<213> ORGANISM: Homo sapiens

<400> SEQUENCE: 39

Gly Tyr Ala Met Ser
 1               5

<210> SEQ ID NO 40
<211> LENGTH: 17
<212> TYPE: PRT
<213> ORGANISM: Homo sapiens

<400> SEQUENCE: 40

Gln Ile Asp Pro Trp Gly Gln Glu Thr Leu Tyr Ala Asp Ser Val Lys
 1               5                  10                  15
```

```
<210> SEQ ID NO 41
<211> LENGTH: 17
<212> TYPE: PRT
<213> ORGANISM: Homo sapiens

<400> SEQUENCE: 41

Glu Ile Ala Pro Pro Gly Leu Asn Thr Arg Tyr Ala Asp Ser Val Lys
1               5                   10                  15

Gly

<210> SEQ ID NO 42
<211> LENGTH: 16
<212> TYPE: PRT
<213> ORGANISM: Homo sapiens

<400> SEQUENCE: 42

Thr Ile Ser Asp Ser Asp Ala Thr Asp Tyr Ala Asp Ser Val Lys Gly
1               5                   10                  15

<210> SEQ ID NO 43
<211> LENGTH: 17
<212> TYPE: PRT
<213> ORGANISM: Homo sapiens

<400> SEQUENCE: 43

Asp Ile Ser Asp Asp Gly Asp Ala Thr Tyr Tyr Ala Asp Ser Val Lys
1               5                   10                  15

Gly

<210> SEQ ID NO 44
<211> LENGTH: 17
<212> TYPE: PRT
<213> ORGANISM: Homo sapiens

<400> SEQUENCE: 44

Asp Ile Ala Ser Thr Gly Tyr Tyr Thr Asp Tyr Ala Asp Ser Val Lys
1               5                   10                  15

Gly

<210> SEQ ID NO 45
<211> LENGTH: 17
<212> TYPE: PRT
<213> ORGANISM: Homo sapiens

<400> SEQUENCE: 45

Ser Ile Ser Ser Ser Gly Tyr Tyr Thr Asp Tyr Ala Asp Ser Val Lys
1               5                   10                  15

Gly

<210> SEQ ID NO 46
<211> LENGTH: 17
<212> TYPE: PRT
<213> ORGANISM: Homo sapiens

<400> SEQUENCE: 46

Ser Ile Ser Ser Asp Gly Ser Tyr Thr Asp Tyr Ala Asp Ser Val Lys
1               5                   10                  15

Gly
```

```
<210> SEQ ID NO 47
<211> LENGTH: 17
<212> TYPE: PRT
<213> ORGANISM: Homo sapiens

<400> SEQUENCE: 47

Thr Ile Asn Tyr Ser Gly Ser Gly Thr Thr Tyr Ala Asp Ser Val Lys
1               5                   10                  15
Gly

<210> SEQ ID NO 48
<211> LENGTH: 7
<212> TYPE: PRT
<213> ORGANISM: Homo sapiens

<400> SEQUENCE: 48

Leu Thr Gly Arg Phe Asp Tyr
1               5

<210> SEQ ID NO 49
<211> LENGTH: 7
<212> TYPE: PRT
<213> ORGANISM: Homo sapiens

<400> SEQUENCE: 49

Ser Asp Thr Ala Phe Asp Tyr
1               5

<210> SEQ ID NO 50
<211> LENGTH: 7
<212> TYPE: PRT
<213> ORGANISM: Homo sapiens

<400> SEQUENCE: 50

Thr Thr Asp Tyr Phe Asp Tyr
1               5

<210> SEQ ID NO 51
<211> LENGTH: 7
<212> TYPE: PRT
<213> ORGANISM: Homo sapiens

<400> SEQUENCE: 51

Ser Ser Thr Thr Phe Asp Tyr
1               5

<210> SEQ ID NO 52
<211> LENGTH: 7
<212> TYPE: PRT
<213> ORGANISM: Homo sapiens

<400> SEQUENCE: 52

Asn Asn Ala Ser Phe Asp Tyr
1               5

<210> SEQ ID NO 53
<211> LENGTH: 7
<212> TYPE: PRT
<213> ORGANISM: Homo sapiens

<400> SEQUENCE: 53

Ser Ala Ser Ser Phe Asp Tyr
1               5
```

```
<210> SEQ ID NO 54
<211> LENGTH: 7
<212> TYPE: PRT
<213> ORGANISM: Homo sapiens

<400> SEQUENCE: 54

Ser Thr Asp Ala Phe Asp Tyr
1               5

<210> SEQ ID NO 55
<211> LENGTH: 7
<212> TYPE: PRT
<213> ORGANISM: Homo sapiens

<400> SEQUENCE: 55

Asn Ala Ala Tyr Phe Asp Tyr
1               5

<210> SEQ ID NO 56
<211> LENGTH: 11
<212> TYPE: PRT
<213> ORGANISM: Homo sapiens

<400> SEQUENCE: 56

Arg Ala Ser Gln Ser Ile Ser Ser Tyr Leu Asn
1               5                   10

<210> SEQ ID NO 57
<211> LENGTH: 7
<212> TYPE: PRT
<213> ORGANISM: Homo sapiens

<400> SEQUENCE: 57

Ser Ala Ser Gln Leu Gln Ser
1               5

<210> SEQ ID NO 58
<211> LENGTH: 7
<212> TYPE: PRT
<213> ORGANISM: Homo sapiens

<400> SEQUENCE: 58

Leu Ala Ser Asn Leu Gln Ser
1               5

<210> SEQ ID NO 59
<211> LENGTH: 7
<212> TYPE: PRT
<213> ORGANISM: Homo sapiens

<400> SEQUENCE: 59

Tyr Ala Ser Tyr Leu Gln Ser
1               5

<210> SEQ ID NO 60
<211> LENGTH: 7
<212> TYPE: PRT
<213> ORGANISM: Homo sapiens

<400> SEQUENCE: 60

Ala Ala Ser Ala Leu Gln Ser
1               5

<210> SEQ ID NO 61
<211> LENGTH: 7
```

<212> TYPE: PRT
<213> ORGANISM: Homo sapiens

<400> SEQUENCE: 61

Asp Ala Ser Thr Leu Gln Ser
1               5

<210> SEQ ID NO 62
<211> LENGTH: 7
<212> TYPE: PRT
<213> ORGANISM: Homo sapiens

<400> SEQUENCE: 62

Ala Ala Ser Tyr Leu Gln Ser
1               5

<210> SEQ ID NO 63
<211> LENGTH: 7
<212> TYPE: PRT
<213> ORGANISM: Homo sapiens

<400> SEQUENCE: 63

Gly Ala Ser Gly Leu Gln Ser
1               5

<210> SEQ ID NO 64
<211> LENGTH: 9
<212> TYPE: PRT
<213> ORGANISM: Homo sapiens

<400> SEQUENCE: 64

Gln Gln Gly Pro Gly Thr Pro Asn Thr
1               5

<210> SEQ ID NO 65
<211> LENGTH: 9
<212> TYPE: PRT
<213> ORGANISM: Homo sapiens

<400> SEQUENCE: 65

Gln Gln Ala Glu Tyr Met Pro Leu Thr
1               5

<210> SEQ ID NO 66
<211> LENGTH: 9
<212> TYPE: PRT
<213> ORGANISM: Homo sapiens

<400> SEQUENCE: 66

Gln Gln Ser Ser Ser Ser Pro Asp Thr
1               5

<210> SEQ ID NO 67
<211> LENGTH: 9
<212> TYPE: PRT
<213> ORGANISM: Homo sapiens

<400> SEQUENCE: 67

Gln Gln Gly Thr Asp Ser Pro Ala Thr
1               5

<210> SEQ ID NO 68
<211> LENGTH: 9
<212> TYPE: PRT
<213> ORGANISM: Homo sapiens

<400> SEQUENCE: 68

Gln Gln Thr Asp Ser Tyr Pro Thr Thr
1               5

<210> SEQ ID NO 69
<211> LENGTH: 9
<212> TYPE: PRT
<213> ORGANISM: Homo sapiens

<400> SEQUENCE: 69

Gln Gln Asp Asp Ala Tyr Pro Thr Thr
1               5

<210> SEQ ID NO 70
<211> LENGTH: 9
<212> TYPE: PRT
<213> ORGANISM: Homo sapiens

<400> SEQUENCE: 70

Gln Gln Asp Asn Asn Tyr Pro Thr Thr
1               5

<210> SEQ ID NO 71
<211> LENGTH: 9
<212> TYPE: PRT
<213> ORGANISM: Homo sapiens

<400> SEQUENCE: 71

Gln Gln Ser Ala Asn Ala Pro Thr Thr
1               5

<210> SEQ ID NO 72
<211> LENGTH: 23
<212> TYPE: DNA
<213> ORGANISM: Artificial Sequence
<220> FEATURE:
<223> OTHER INFORMATION: reverse primer

<400> SEQUENCE: 72
cccttgaacc tcctcgttcg acc                                              23

<210> SEQ ID NO 73
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 73

Asn Leu Val Pro Met Val Ala Thr Val
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 74

Lys Leu Gln Cys Val Asp Leu His Val
1               5

<210> SEQ ID NO 75

```
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 75

Tyr Val Asp Pro Val Ile Thr Ser Ile
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 76

Tyr Met Phe Pro Asn Ala Pro Tyr Leu
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 77

Cys Met Thr Trp Asn Gln Met Asn Leu
1               5

<210> SEQ ID NO 78
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 78

Thr Leu Pro Pro Ala Trp Gln Pro Phe Leu
1               5                   10

<210> SEQ ID NO 79
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 79

Ser Leu Gly Glu Gln Gln Tyr Ser Val
1               5

<210> SEQ ID NO 80
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 80

Glu Leu Met Leu Gly Glu Phe Leu Lys Leu
1               5                   10

<210> SEQ ID NO 81
<211> LENGTH: 10
```

```
<212> TYPE: PRT
<213> ORGANISM: Artificial Sequence
<220> FEATURE:
<223> OTHER INFORMATION: Synthetic Peptide

<400> SEQUENCE: 81

Val Ile Ser Asn Asp Val Cys Ala Gln Val
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 82

Phe Leu Thr Pro Lys Lys Leu Gln Cys Val
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 83

Val Ile Leu Lys Lys Ala Thr Glu Tyr Val
1               5                   10

<210> SEQ ID NO 84
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 84

Ala Leu Leu Met Ala Gly Leu Ala Leu
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 85

Ala Leu Phe Asp Ile Glu Ser Lys Val
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 86

Leu Met Leu Gly Glu Phe Leu Lys Leu
1               5
```